United States Patent [19]
Meagher et al.

[11] Patent Number: 5,668,294
[45] Date of Patent: Sep. 16, 1997

[54] METAL RESISTANCE SEQUENCES AND TRANSGENIC PLANTS

[75] Inventors: Richard B. Meagher; Anne O. Summers, both of Athens, Ga.

[73] Assignee: University of Georgia Research Foundation Inc., Athens, Ga.

[21] Appl. No.: 427,097

[22] Filed: Apr. 21, 1995

[51] Int. Cl.$^6$ .................... C12N 15/31; C12N 15/82; C12N 15/29; A01H 5/00

[52] U.S. Cl. .................... 800/205; 800/DIG. 40; 800/DIG. 48; 800/DIG. 49; 800/DIG. 52; 800/DIG. 15; 435/69.1; 435/172.3; 435/320.1; 536/23.2; 536/23.7; 536/24.1

[58] Field of Search .................... 800/205, DIG. 9, 800/DIG. 15, DIG. 40, DIG. 52, DIG. 48, DIG. 49; 435/172.3, 240.4, 69.1, 320.1; 536/23.2, 23.7, 24.1

[56] References Cited

U.S. PATENT DOCUMENTS

| | | | |
|---|---|---|---|
| 4,849,355 | 7/1989 | Wong | 435/172.3 |
| 5,364,451 | 11/1994 | Raskin et al. | 75/710 |
| 5,380,381 | 1/1995 | Adang et al. | 536/23.71 |

OTHER PUBLICATIONS

Stack, N.M. (1992) "The Reconstruction of the Bacterial Gene merA", *BS Thesis*, University of Georgia.
Meagher, R.B. (1994) "Phyto–remediation of heavy metal ion toxicity: A highly modified bacterial MerA gene confers mercuric ion resistance to transgenic Arabidopsis plants," Abstract of presentation to Dept. of Energy Phyto–remediation Research Workshop, Santa Rosa, California, Jul. 25–26, 1994.
Wilde et al. (1994) *In vitro Cellular & Developmental Biology Animal* 30A (3 Part 2), p. 60.
Rugh et al. (1994) "Ionic Mercury Detoxification by Transgenic Plants," poster abstract presented at American Society of Plant Physiology Annual Meeting, Portland, Oregon, Jul. 30–Aug. 3, 1994.
Thompson, D.M. (1990) *Transcripitional and Post–transcriptional Regulation of the Genes Encoding the Small Subunit of Ribulose–1,5–Bisphosphate Carboxylase*, Ph.D. Thesis, University of Georgia, Athens, Georgia.
Grill et al. (1987) *Proc. Natl. Acad. Sci. USA* 84:439–443.
Lefebvre et al. (1987) *Biotechnology* 5:1053–1056.
Gilbert and Summers (1988) *Plasmid* 20:127–136.
Begley et al. (1986) *Biochemistry* 25;7186–7192.
Begley et al. (1986) *Biochemistry* 25:7192–7200.
Summers, A.O. (1986) *Ann. Rev. Microbiology* 40:607–634.
Summers and Sugarman (1974) *Journal of Bacteriology* 119:242–249.
Rinderle et al. (1983) *Biochemistry* 22:869–876.
Barrineau et al. (1984) *Journal of Molecular and Applied Genetics* 2:601–619.
McClelland and Ivarie (1982) *Nucleic Acids Research* 10:7865–7877.
Murray et al. (1989) *Nucleic Acids Research* 17:477–494.
Brown et al. (1983) *Biochemistry* 22:4089–4095.
Misra et al. (1985) *Gene* 34:253–262.
Stormo et al. (1982) *Nucleic Acids Res.* 10:2971–2996.
Heidecker and Messing (1986) *Ann. Rev. Plant Physiol.* 37:439–466.
Foster, T.J. (1983) *Microbiol. Rev.* 47:361–409.
Rensing et al. (1992) *Journal of Bacteriology* 174:1288–1292.
Scheller et al. (1987) *Plant Physiology* 85:1031–1035.

*Primary Examiner*—David T. Fox
*Assistant Examiner*—Thomas Haas
*Attorney, Agent, or Firm*—Greenlee, Winner and Sullivan P.C.

[57] ABSTRACT

The present invention provides nucleic acid sequences encoding a metal ion resistance protein, which are expressible in plant cells. The metal resistance protein provides for the enzymatic reduction of metal ions including by not limited to divalent Cu, divalent mercury, trivalent gold, divalent cadmium, lead ions and monovalent silver ions. Transgenic plants which express these coding sequences exhibit increased resistance to metal ions in the environment as compared with plants which have not been so genetically modified. Transgenic plants which are resistant to organomercurials including alkylmercury compounds, among others, are provided by the further inclusion of plant-expressible organomercurial lyase coding sequences. Furthermore, these transgenic plants which have been genetically modified to express the metal resistance coding sequences of the present invention can participate in the bioremediation of metal contamination via the enzymatic reduction of metal ions. Transgenic plants resistant to organomercurials can further mediate remediation of alkylmercury compounds in the environment by causing the freeing of mercuric ions and the reduction of the ionic mercury to the less toxic elemental mercury.

28 Claims, 6 Drawing Sheets

```
5'S
          10        20         30        40        50      59
CTAGAACTAG TGGATCCCTA GATCTAAGAA GGAACCACA ATG AGC ACT CTC AAA ATC AC-3'
           BamHI      BglII  S.D.         MET  merA
                      STOP       P.T.
```

```
3'A
          10        20         30    36
TATCGAATTC CTGCAGCCTC ACCCGGCGCA GCAGGA 3'

EcoRI   PstI        merA homology
```

282-312A & 307-339S

```
              285                           290                           295                       300
    Leu Glu Leu Ala Gln Ala Phe Ala Arg Leu Gly Ala Lys Val Thr Ile Leu Ala Arg
5'-ctt gaa ctt gcc cag gcc ttt gca cgt ctt ggt gct aaa gtg acc att ctt gca cgc
5'-             G   C   C   A   C   A   G   G             G   C   G   T
3'-GAA CTT GAA CGG GTC CGG AAA CGT GCA GAA CCA CGA TTT CAC TGG TAA GAA CGT GCG
    merA homology
              305                           310                           315                       320
Ser Thr Leu Phe Phe Arg Glu Asp Pro Ala Ile Gly Glu Ala Val Thr Ala Ala Phe Arg
tcc act ctc ttc ttt cgt GAA GAC CCA GCT ATA GGT GAA GCT GTT ACT GCT GCA TTT CGC
AG   G   G       C   C       overlap region          C       C   G           C
AGG TGA GAG AAG AAA GCA CTT CTG GGT CGA TAT CC-5'

325                           330                           335                   339
Met Glu Gly Ile Glu Val Arg Glu His Thr Gln Ala Ser Gln Val Ala Tyr Ile Asn
ATG GAA GGC ATT GAA GTG CGT GAG CAT ACT CAA GCA AGC CAA GTT GCC TAT ATC AAT-3'
     G       C   G       A G   A   C   C   G   C       G   C   G                -3'
                                                                    merA homology
```

FIG. 1C

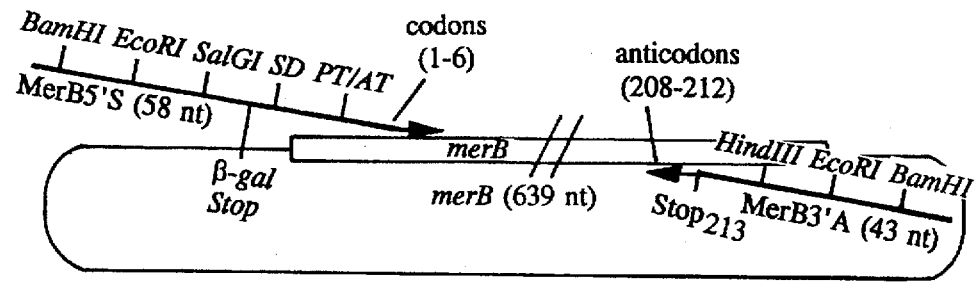

pCT12 contains a 1.5 kb *EcoRI* fragment from *S. typh.* broad spectrum resistance plasmid 1. PCR amplify 639 bp merB coding sequence with MerB5'S and MerB3'A primers.
2. *BamHI* cloning into pBS-SK

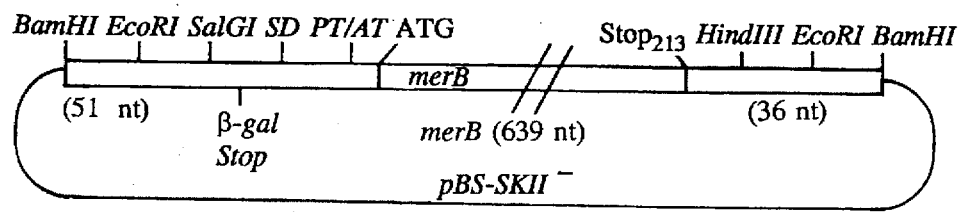

Test several clones for resistance to organomercurials using PCMB in a strain also containing pDU202 plasmid) ($Hg^{++}$ resistance) and use most active clones.

Plant expression: *BamHI/PstI* (pBS-SK site) cloning between *35Sp* and *NOS3'* in binary vector.

Animal Expression: *BamHI - HindIII* cloning into pBC-CMV for fish experiments.

*SD - Shine Delgarno, PT/AT synthetic plant and animal translation signals

FIG. 4

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 1728 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 14..1708

( x i ) SEQUENCE DESCRIPTION: SEQ ID NO:1:

```
AAGGAACGAT GGT ATG AGC ACT CTC AAA ATC ACC GGC ATG ACT TGC GAC          49
            Met Ser Thr Leu Lys Ile Thr Gly Met Thr Cys Asp
             1               5                  10

TCG TGC GCA GTG CAT GTC AAG GAC GCC CTG GAG AAA GTG CCC GGC GTG         97
Ser Cys Ala Val His Val Lys Asp Ala Leu Glu Lys Val Pro Gly Val
            15                  20                  25

CAA TCA GCG GAT GTC TCC TAC GCC AAG GGC AGC GCC AAG CTC GCC ATT        145
Gln Ser Ala Asp Val Ser Tyr Ala Lys Gly Ser Ala Lys Leu Ala Ile
         30                  35                  40

GAG GTC GGC ACG TCA CCC GAC GCG CTG ACG GCC GCT GTA GCT GGA CTC        193
Glu Val Gly Thr Ser Pro Asp Ala Leu Thr Ala Ala Val Ala Gly Leu
 45                  50                  55                  60

GGT TAT CGG GCC ACG CTG GCC GAT GCC CCC TCA GTT TCG ACG CCG GGC        241
Gly Tyr Arg Ala Thr Leu Ala Asp Ala Pro Ser Val Ser Thr Pro Gly
```

```
GGA TTG CTC GAC AAG ATG CGC GAT CTG CTG GGC AGA AAC GAC AAG ACG      289
Gly Leu Leu Asp Lys Met Arg Asp Leu Leu Gly Arg Asn Asp Lys Thr
            80              85                  90

GGT AGC AGC GGC GCA TTG CAT ATC GCC GTC ATC GGC AGC GGC GGG GCC      337
Gly Ser Ser Gly Ala Leu His Ile Ala Val Ile Gly Ser Gly Gly Ala
        95              100             105

GCG ATG GCA GCG GCG CTG AAG GCC GTC GAG CAA GGC GCA CCT GTC ACG      385
Ala Met Ala Ala Ala Leu Lys Ala Val Glu Gln Gly Ala Pro Val Thr
    110             115                 120

CTG ATC GAG CGC GGC ACC ATC GGC GGC ACC TGC GTC AAT GTC GGT TGT      433
Leu Ile Glu Arg Gly Thr Ile Gly Gly Thr Cys Val Asn Val Gly Cys
125             130                 135                 140

GTG CCG TCC AAG ATC ATG ATC CGC GCC GCC CAT ATC GCC CAT CTG CGC      481
Val Pro Ser Lys Ile Met Ile Arg Ala Ala His Ile Ala His Leu Arg
                145                 150                 155

CGG GAA AGC CCG TTC GAT GGC GGC ATC GCC GCT ACC ACG CCG ACC ATC      529
Arg Glu Ser Pro Phe Asp Gly Gly Ile Ala Ala Thr Thr Pro Thr Ile
                160                 165                 170

CAG CGC ACG GCG CTG CTG GCC CAG CAG CAG GCC CGC GTC GAT GAA CTG      577
Gln Arg Thr Ala Leu Leu Ala Gln Gln Gln Ala Arg Val Asp Glu Leu
        175                 180                 185

CGC CAC GCC AAG TAC GAA GGC ATC TTG GAG GGC AAT CCG GCG ATC ACT      625
Arg His Ala Lys Tyr Glu Gly Ile Leu Glu Gly Asn Pro Ala Ile Thr
    190                 195                 200

GTG CTG CAC GGC TCC GCC CGC TTT AAG GAC AAT CGC AAC CTG ATC GTG      673
Val Leu His Gly Ser Ala Arg Phe Lys Asp Asn Arg Asn Leu Ile Val
205             210                 215                 220

CAA CTC AAC GAC GGC GGC GAG CGC GTG GTG GCA TTC GAC CGC TGC CTG      721
Gln Leu Asn Asp Gly Gly Glu Arg Val Val Ala Phe Asp Arg Cys Leu
                225                 230                 235

ATC GCC ACC GGC GCG AGC CCG GCC GTG CCG CCG ATT CCC GGC CTG AAA      769
Ile Ala Thr Gly Ala Ser Pro Ala Val Pro Pro Ile Pro Gly Leu Lys
            240                 245                 250

GAC ACT CCG TAC TGG ACT TCC ACT GAA GCG CTG GTC AGC GAG ACG ATT      817
Asp Thr Pro Tyr Trp Thr Ser Thr Glu Ala Leu Val Ser Glu Thr Ile
        255                 260                 265

CCT AAG CGC CTG GCC GTG ATT GGC TCA TCA GTG CTG GCG CTG GAG CTG      865
Pro Lys Arg Leu Ala Val Ile Gly Ser Ser Val Leu Ala Leu Glu Leu
    270                 275                 280

GCG CAG GCG TTC GCC CGA CTC GGA GCG AAG GTG ACG ATC CTG GCT CGC      913
Ala Gln Ala Phe Ala Arg Leu Gly Ala Lys Val Thr Ile Leu Ala Arg
285             290                 295                 300

AGC ACG CTG TTC TTC CGC GAA GAC CCA GCT ATA GGC GAA GCT GTC ACG      961
Ser Thr Leu Phe Phe Arg Glu Asp Pro Ala Ile Gly Glu Ala Val Thr
                305                 310                 315

GCC GCA TTC CGG ATG GAG GGC ATC GAG GTG AGG GAA CAC ACC CAG GCC     1009
Ala Ala Phe Arg Met Glu Gly Ile Glu Val Arg Glu His Thr Gln Ala
            320                 325                 330

AGC CAG GTC GCG TAT ATC AAT GGT GAA GGG GAC GGC GAA TTC GTG CTC     1057
Ser Gln Val Ala Tyr Ile Asn Gly Glu Gly Asp Gly Glu Phe Val Leu
        335                 340                 345

ACC ACG GCG CAC GGC GAA CTG CGC GCC GAC AAG CTG CTG GTC GCC ACC     1105
Thr Thr Ala His Gly Glu Leu Arg Ala Asp Lys Leu Leu Val Ala Thr
    350                 355                 360

GGC CGC GCG CCC AAC ACA CGC AAG CTG GCA CTG GAT GCG ACG GGC GTC     1153
Gly Arg Ala Pro Asn Thr Arg Lys Leu Ala Leu Asp Ala Thr Gly Val
365             370                 375                 380

ACG CTC ACC CCC CAA GGC GCT ATC GTC ATC GAC CCC GGC ATG CGT ACA     1201
Thr Leu Thr Pro Gln Gly Ala Ile Val Ile Asp Pro Gly Met Arg Thr
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 385 |     |     |     |     |     | 390 |     |     |     |     |     | 395 |      |
| AGC | GTG | GAA | CAC | ATC | TAC | GCC | GCA | GGC | GAC | TGC | ACC | GAC | CAG | CCG | CAG | 1249 |
| Ser | Val | Glu | His | Ile | Tyr | Ala | Ala | Gly | Asp | Cys | Thr | Asp | Gln | Pro | Gln |      |
|     |     |     | 400 |     |     |     | 405 |     |     |     |     |     | 410 |     |     |      |
| TTC | GTC | TAT | GTG | GCG | GCA | GCG | GCC | GGC | ACT | CGC | GCC | GCG | ATC | AAC | ATG | 1297 |
| Phe | Val | Tyr | Val | Ala | Ala | Ala | Ala | Gly | Thr | Arg | Ala | Ala | Ile | Asn | Met |      |
|     |     | 415 |     |     |     |     | 420 |     |     |     |     | 425 |     |     |     |      |
| ACC | GGC | GGT | GAC | GCC | GCC | CTG | AAC | CTG | ACC | GCG | ATG | CCG | GCC | GTG | GTG | 1345 |
| Thr | Gly | Gly | Asp | Ala | Ala | Leu | Asn | Leu | Thr | Ala | Met | Pro | Ala | Val | Val |      |
|     | 430 |     |     |     |     | 435 |     |     |     |     | 440 |     |     |     |     |      |
| TTC | ACC | GAC | CCG | CAA | GTG | GCG | ACC | GTA | GGC | TAC | AGC | GAG | GCG | GAA | GCG | 1393 |
| Phe | Thr | Asp | Pro | Gln | Val | Ala | Thr | Val | Gly | Tyr | Ser | Glu | Ala | Glu | Ala |      |
| 445 |     |     |     |     | 450 |     |     |     |     | 455 |     |     |     |     | 460 |      |
| CAC | CAT | GAC | GGC | ATC | AAA | ACT | GAT | AGT | CGC | ACG | CTA | ACG | CTG | GAC | AAC | 1441 |
| His | His | Asp | Gly | Ile | Lys | Thr | Asp | Ser | Arg | Thr | Leu | Thr | Leu | Asp | Asn |      |
|     |     |     |     | 465 |     |     |     |     | 470 |     |     |     |     | 475 |     |      |
| GTG | CCG | CGC | GCG | CTC | GCC | AAC | TTC | GAC | ACG | CGC | GGC | TTC | ATC | AAA | CTG | 1489 |
| Val | Pro | Arg | Ala | Leu | Ala | Asn | Phe | Asp | Thr | Arg | Gly | Phe | Ile | Lys | Leu |      |
|     |     |     | 480 |     |     |     |     | 485 |     |     |     |     | 490 |     |     |      |
| GTG | GTT | GAA | GAA | GGG | AGC | GGA | CGA | CTG | ATC | GGC | GTC | CAG | GCA | GTG | GCC | 1537 |
| Val | Val | Glu | Glu | Gly | Ser | Gly | Arg | Leu | Ile | Gly | Val | Gln | Ala | Val | Ala |      |
|     |     | 495 |     |     |     |     | 500 |     |     |     |     | 505 |     |     |     |      |
| CCG | GAA | GCG | GGC | GAA | CTG | ATC | CAG | ACG | GCC | GCA | CTG | GCG | ATT | CGC | AAC | 1585 |
| Pro | Glu | Ala | Gly | Glu | Leu | Ile | Gln | Thr | Ala | Ala | Leu | Ala | Ile | Arg | Asn |      |
| 510 |     |     |     |     | 515 |     |     |     |     | 520 |     |     |     |     |     |      |
| CGG | ATG | ACG | GTG | CAG | GAA | CTG | GCC | GAC | CAG | TTG | TTC | CCC | TAC | CTG | ACG | 1633 |
| Arg | Met | Thr | Val | Gln | Glu | Leu | Ala | Asp | Gln | Leu | Phe | Pro | Tyr | Leu | Thr |      |
| 525 |     |     |     |     | 530 |     |     |     |     | 535 |     |     |     |     | 540 |      |
| ATG | GTC | GAA | GGG | TTG | AAG | CTC | GCG | GCG | CAG | ACC | TTC | AAC | AAG | GAT | GTG | 1681 |
| Met | Val | Glu | Gly | Leu | Lys | Leu | Ala | Ala | Gln | Thr | Phe | Asn | Lys | Asp | Val |      |
|     |     |     |     | 545 |     |     |     |     | 550 |     |     |     |     | 555 |     |      |
| AAG | CAG | CTT | TCC | TGC | TGC | GCC | GGG | TGA | GGACAAGGAG | | | GTGTGCGATG | | | | 1728 |
| Lys | Gln | Leu | Ser | Cys | Cys | Ala | Gly | *   |     |     |     |     |     |     |     |      |
|     |     |     | 560 |     |     |     |     | 565 |     |     |     |     |     |     |     |      |

(2) INFORMATION FOR SEQ ID NO:2:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:2:

| Met | Ser | Thr | Leu | Lys | Ile | Thr | Gly | Met | Thr | Cys | Asp | Ser | Cys | Ala | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| His | Val | Lys | Asp | Ala | Leu | Glu | Lys | Val | Pro | Gly | Val | Gln | Ser | Ala | Asp |
|     |     |     | 20  |     |     |     |     | 25  |     |     |     |     | 30  |     |     |
| Val | Ser | Tyr | Ala | Lys | Gly | Ser | Ala | Lys | Leu | Ala | Ile | Glu | Val | Gly | Thr |
|     |     | 35  |     |     |     |     | 40  |     |     |     |     | 45  |     |     |     |
| Ser | Pro | Asp | Ala | Leu | Thr | Ala | Ala | Val | Ala | Gly | Leu | Gly | Tyr | Arg | Ala |
|     | 50  |     |     |     |     | 55  |     |     |     |     | 60  |     |     |     |     |
| Thr | Leu | Ala | Asp | Ala | Pro | Ser | Val | Ser | Thr | Pro | Gly | Gly | Leu | Leu | Asp |
| 65  |     |     |     |     | 70  |     |     |     |     | 75  |     |     |     |     | 80  |
| Lys | Met | Arg | Asp | Leu | Leu | Gly | Arg | Asn | Asp | Lys | Thr | Gly | Ser | Ser | Gly |
|     |     |     |     | 85  |     |     |     |     | 90  |     |     |     |     | 95  |     |
| Ala | Leu | His | Ile | Ala | Val | Ile | Gly | Ser | Gly | Gly | Ala | Ala | Met | Ala | Ala |
|     |     |     | 100 |     |     |     |     | 105 |     |     |     |     | 110 |     |     |
| Ala | Leu | Lys | Ala | Val | Glu | Gln | Gly | Ala | Pro | Val | Thr | Leu | Ile | Glu | Arg |

|     |     |     | 115 |     |     |     | 120 |     |     |     | 125 |     |     |     |
|-----|-----|-----|-----|-----|-----|-----|-----|-----|-----|-----|-----|-----|-----|-----|
| Gly | Thr | Ile | Gly | Gly | Thr | Cys | Val | Asn | Val | Gly | Cys | Val | Pro | Ser | Lys |
|     | 130 |     |     |     |     | 135 |     |     |     | 140 |     |     |     |     |
| Ile | Met | Ile | Arg | Ala | Ala | His | Ile | Ala | His | Leu | Arg | Arg | Glu | Ser | Pro |
| 145 |     |     |     |     | 150 |     |     |     | 155 |     |     |     |     |     | 160 |
| Phe | Asp | Gly | Gly | Ile | Ala | Ala | Thr | Thr | Pro | Thr | Ile | Gln | Arg | Thr | Ala |
|     |     |     |     | 165 |     |     |     |     | 170 |     |     |     |     | 175 |     |
| Leu | Leu | Ala | Gln | Gln | Ala | Arg | Val | Asp | Glu | Leu | Arg | His | Ala | Lys |
|     |     |     | 180 |     |     |     |     | 185 |     |     |     | 190 |     |     |
| Tyr | Glu | Gly | Ile | Leu | Glu | Gly | Asn | Pro | Ala | Ile | Thr | Val | Leu | His | Gly |
|     |     | 195 |     |     |     |     | 200 |     |     |     |     | 205 |     |     |     |
| Ser | Ala | Arg | Phe | Lys | Asp | Asn | Arg | Asn | Leu | Ile | Val | Gln | Leu | Asn | Asp |
|     | 210 |     |     |     |     | 215 |     |     |     |     | 220 |     |     |     |     |
| Gly | Gly | Glu | Arg | Val | Val | Ala | Phe | Asp | Arg | Cys | Leu | Ile | Ala | Thr | Gly |
| 225 |     |     |     |     | 230 |     |     |     |     | 235 |     |     |     |     | 240 |
| Ala | Ser | Pro | Ala | Val | Pro | Pro | Ile | Pro | Gly | Leu | Lys | Asp | Thr | Pro | Tyr |
|     |     |     |     | 245 |     |     |     |     | 250 |     |     |     |     | 255 |     |
| Trp | Thr | Ser | Thr | Glu | Ala | Leu | Val | Ser | Glu | Thr | Ile | Pro | Lys | Arg | Leu |
|     |     |     | 260 |     |     |     |     | 265 |     |     |     |     | 270 |     |     |
| Ala | Val | Ile | Gly | Ser | Ser | Val | Leu | Ala | Leu | Glu | Leu | Ala | Gln | Ala | Phe |
|     |     | 275 |     |     |     |     | 280 |     |     |     |     | 285 |     |     |     |
| Ala | Arg | Leu | Gly | Ala | Lys | Val | Thr | Ile | Leu | Ala | Arg | Ser | Thr | Leu | Phe |
|     | 290 |     |     |     |     | 295 |     |     |     |     | 300 |     |     |     |     |
| Phe | Arg | Glu | Asp | Pro | Ala | Ile | Gly | Glu | Ala | Val | Thr | Ala | Ala | Phe | Arg |
| 305 |     |     |     |     | 310 |     |     |     |     | 315 |     |     |     |     | 320 |
| Met | Glu | Gly | Ile | Glu | Val | Arg | Glu | His | Thr | Gln | Ala | Ser | Gln | Val | Ala |
|     |     |     |     | 325 |     |     |     |     | 330 |     |     |     |     | 335 |     |
| Tyr | Ile | Asn | Gly | Glu | Gly | Asp | Gly | Glu | Phe | Val | Leu | Thr | Thr | Ala | His |
|     |     |     | 340 |     |     |     |     | 345 |     |     |     |     | 350 |     |     |
| Gly | Glu | Leu | Arg | Ala | Asp | Lys | Leu | Leu | Val | Ala | Thr | Gly | Arg | Ala | Pro |
|     |     |     | 355 |     |     |     |     | 360 |     |     |     |     | 365 |     |     |
| Asn | Thr | Arg | Lys | Leu | Ala | Leu | Asp | Ala | Thr | Gly | Val | Thr | Leu | Thr | Pro |
|     |     |     | 370 |     |     |     |     | 375 |     |     |     |     | 380 |     |     |
| Gln | Gly | Ala | Ile | Val | Ile | Asp | Pro | Gly | Met | Arg | Thr | Ser | Val | Glu | His |
| 385 |     |     |     |     | 390 |     |     |     |     | 395 |     |     |     |     | 400 |
| Ile | Tyr | Ala | Ala | Gly | Asp | Cys | Thr | Asp | Gln | Pro | Gln | Phe | Val | Tyr | Val |
|     |     |     |     | 405 |     |     |     |     | 410 |     |     |     |     | 415 |     |
| Ala | Ala | Ala | Ala | Gly | Thr | Arg | Ala | Ala | Ile | Asn | Met | Thr | Gly | Gly | Asp |
|     |     |     | 420 |     |     |     |     | 425 |     |     |     |     | 430 |     |     |
| Ala | Ala | Leu | Asn | Leu | Thr | Ala | Met | Pro | Ala | Val | Val | Phe | Thr | Asp | Pro |
|     |     |     | 435 |     |     |     |     | 440 |     |     |     |     | 445 |     |     |
| Gln | Val | Ala | Thr | Val | Gly | Tyr | Ser | Glu | Ala | Glu | Ala | His | His | Asp | Gly |
|     | 450 |     |     |     |     | 455 |     |     |     |     | 460 |     |     |     |     |
| Ile | Lys | Thr | Asp | Ser | Arg | Thr | Leu | Thr | Leu | Asp | Asn | Val | Pro | Arg | Ala |
| 465 |     |     |     |     | 470 |     |     |     |     | 475 |     |     |     |     | 480 |
| Leu | Ala | Asn | Phe | Asp | Thr | Arg | Gly | Phe | Ile | Lys | Leu | Val | Val | Glu | Glu |
|     |     |     |     | 485 |     |     |     |     | 490 |     |     |     |     | 495 |     |
| Gly | Ser | Gly | Arg | Leu | Ile | Gly | Val | Gln | Ala | Val | Ala | Pro | Glu | Ala | Gly |
|     |     |     | 500 |     |     |     |     | 505 |     |     |     |     | 510 |     |     |
| Glu | Leu | Ile | Gln | Thr | Ala | Ala | Leu | Ala | Ile | Arg | Asn | Arg | Met | Thr | Val |
|     |     |     | 515 |     |     |     |     | 520 |     |     |     |     | 525 |     |     |
| Gln | Glu | Leu | Ala | Asp | Gln | Leu | Phe | Pro | Tyr | Leu | Thr | Met | Val | Glu | Gly |
|     |     |     | 530 |     |     |     |     | 535 |     |     |     |     | 540 |     |     |

| Leu | Lys | Leu | Ala | Ala | Gln | Thr | Phe | Asn | Lys | Asp | Val | Lys | Gln | Leu | Ser |
|-----|-----|-----|-----|-----|-----|-----|-----|-----|-----|-----|-----|-----|-----|-----|-----|
| 545 |     |     |     |     | 550 |     |     |     |     | 555 |     |     |     |     | 560 |

| Cys | Cys | Ala | Gly |
|-----|-----|-----|-----|
|     |     |     | 565 |

( 2 ) INFORMATION FOR SEQ ID NO:3:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( i v ) ANTI-SENSE: NO ( x i ) SEQUENCE DESCRIPTION: SEQ ID NO:3:

CTAGAACTAG TGGATCCCTA GATCTAAGAA GGAACCACAA TGAGCACTCT CAAAATCAC    59

( 2 ) INFORMATION FOR SEQ ID NO:4:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( x i ) SEQUENCE DESCRIPTION: SEQ ID NO:4:

CCTATAGCTG GGTCTTCACG AAAGAAGAGA GTGGAGCGTG CAAGAATGGT CACTTTAGCA    60

CCAAGACGTG CAAAGGCCTG CGCCAGCTCC AG    92

( 2 ) INFORMATION FOR SEQ ID NO:5:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( i v ) ANTI-SENSE: NO ( x i ) SEQUENCE DESCRIPTION: SEQ ID NO:5:

GAAGACCCAG CTATAGGTGA AGCTGTTACT GCTGCATTTC GCATGGAAGG CATTGAAGTG    60

CGTGAGCATA CTCAAGCAAG CCAAGTTGCC TATATCAAT    99

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Olgionucleotide"

( i i i ) HYPOTHETICAL: NO ( x i ) SEQUENCE DESCRIPTION: SEQ ID NO:6:

TATCGAATTC CTGCAGCCTC ACCCGGCGCA GCAGGA    36

( 2 ) INFORMATION FOR SEQ ID NO:7:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( x i ) SEQUENCE DESCRIPTION: SEQ ID NO:7:

GCTTCAGTGG AAGTCCAGTA AGGAGTGTCC TTGAGACCAG GAATTGGTGG AACAGCTGGG    60

CTTGCACCAG TGGCAATGAG ACAGCGGTCG AATGCCACCA C    101

( 2 ) INFORMATION FOR SEQ ID NO:8:

( i ) SEQUENCE CHARACTERISTICS:
        ( A ) LENGTH: 109 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( i v ) ANTI-SENSE: NO ( x i ) SEQUENCE DESCRIPTION: SEQ ID NO:8:

TGGACTTCCA CTGAAGCACT AGTGTCTGAG ACCATTCCAA AGCGTCTTGC AGTCATTGGC    60

TCCTCTGTGG TGGCTCTTGA ACTTGCCCAG GCCTTTGCAC GTCTTGGTG    109

( 2 ) INFORMATION FOR SEQ ID NO:9:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( x i ) SEQUENCE DESCRIPTION: SEQ ID NO:9:

GTGCAGAGCC ATGAAGCACA GTGATGGCTG GGTTACCTTC TAGAATACCT TCATACTTTG    60

CATGACGAAG TTCATCAACA CGGGCCTGCT GCTGGGCCA    99

( 2 ) INFORMATION FOR SEQ ID NO:10:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Olgionucleotide"

(iii) HYPOTHETICAL: NO (iv) ANTI-SENSE: NO (xi) SEQUENCE DESCRIPTION: SEQ ID NO:10:

GCTTCATGGC TCTGCACGTT TCAAGGACAA CCGTAACCTC ATTGTTCAAC TTAATGATGG  60

TGGTGAACGT GTGGTGGCTT TTGACCGCTG TCTCATTGC  99

(2) INFORMATION FOR SEQ ID NO:11:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="Oligonucleotide"

(iii) HYPOTHETICAL: NO (xi) SEQUENCE DESCRIPTION: SEQ ID NO:11:

CACGACCAGT TGCAACAAGG AGTTTGTCTG CACGAAGTTC ACCATGAGCA GTGGTAAGGA  60

CGAATTCACC ATCACCTTCA CCATTGATAT AGGCAACTTG  100

(2) INFORMATION FOR SEQ ID NO:12:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="Oligonucleotide"

(iii) HYPOTHETICAL: NO (iv) ANTI-SENSE: NO (xi) SEQUENCE DESCRIPTION: SEQ ID NO:12:

TGTTGCAACT GGTCGTGCAC CAAACACTCG CAAACTGGCA CTTGATGCAA CTGGTGTGAC  60

CCTTACTCCA CAAGGTGCTA TTGTCATCGA CCCCGGCAT  99

(2) INFORMATION FOR SEQ ID NO:13:

(i) SEQUENCE CHARACTERISTICS:
        (A) LENGTH: 1752 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc ="Mutagenized merApe38"

(iii) HYPOTHETICAL: NO (ix) FEATURE:
        (A) NAME/KEY: CDS
        (B) LOCATION: 40..1734

(ix) FEATURE:
        (A) NAME/KEY: mat_peptide
        (B) LOCATION: 40..1731

(xi) SEQUENCE DESCRIPTION: SEQ ID NO:13:

CTAGAACTAG TGGATCCCTA GATCTAAGAA GGAACCACA ATG AGC ACT CTC AAA  54
                                                                                   Met Ser Thr Leu Lys
                                                                                     1               5

| | | | | | | | | | | | | | | | | |
|---|---|---|---|---|---|---|---|---|---|---|---|---|---|---|---|---|
| ATC | ACC | GGC | ATG | ACT | TGC | GAC | TCG | TGC | GCA | GTG | CAT | GTC | AAG | GAC | GCC | 102 |
| Ile | Thr | Gly | Met | Thr | Cys | Asp | Ser | Cys | Ala | Val | His | Val | Lys | Asp | Ala | |
| | | | | 10 | | | | | 15 | | | | | 20 | | |
| CTG | GAG | AAA | GTG | CCC | GGC | GTG | CAA | TCA | GCG | GAT | GTC | TCC | TAC | GCC | AAG | 150 |
| Leu | Glu | Lys | Val | Pro | Gly | Val | Gln | Ser | Ala | Asp | Val | Ser | Tyr | Ala | Lys | |
| | | | 25 | | | | | 30 | | | | | 35 | | | |
| GGC | AGC | GCC | AAG | CTC | GCC | ATT | GAG | GTC | GGC | ACG | TCA | CCC | GAC | GCG | CTG | 198 |
| Gly | Ser | Ala | Lys | Leu | Ala | Ile | Glu | Val | Gly | Thr | Ser | Pro | Asp | Ala | Leu | |
| | | | 40 | | | | | 45 | | | | | 50 | | | |
| ACG | GCC | GCT | GTA | GCT | GGA | CTC | GGT | TAT | CGG | GCC | ACG | CTG | GCC | GAT | GCC | 246 |
| Thr | Ala | Ala | Val | Ala | Gly | Leu | Gly | Tyr | Arg | Ala | Thr | Leu | Ala | Asp | Ala | |
| | | | 55 | | | | | 60 | | | | | 65 | | | |
| CCC | TCA | GTT | TCG | ACG | CCG | GGC | GGA | TTG | CTC | GAC | AAG | ATG | CGC | GAT | CTG | 294 |
| Pro | Ser | Val | Ser | Thr | Pro | Gly | Gly | Leu | Leu | Asp | Lys | Met | Arg | Asp | Leu | |
| | 70 | | | | | 75 | | | | | 80 | | | | | 85 |
| CTG | GGC | AGA | AAC | GAC | AAG | ACG | GGT | AGC | AGC | GGC | GCA | TTG | CAT | ATC | GCC | 342 |
| Leu | Gly | Arg | Asn | Asp | Lys | Thr | Gly | Ser | Ser | Gly | Ala | Leu | His | Ile | Ala | |
| | | | | 90 | | | | | 95 | | | | | 100 | | |
| GTC | ATC | GGC | AGC | GGC | GGG | GCC | GCG | ATG | GCA | GCG | GCG | CTG | AAG | GCC | GTC | 390 |
| Val | Ile | Gly | Ser | Gly | Gly | Ala | Ala | Met | Ala | Ala | Ala | Leu | Lys | Ala | Val | |
| | | | | 105 | | | | | 110 | | | | | 115 | | |
| GAG | CAA | GGC | GCA | CCT | GTC | ACG | CTG | ATC | GAG | CGC | GGC | ACC | ATC | GGC | GGC | 438 |
| Glu | Gln | Gly | Ala | Pro | Val | Thr | Leu | Ile | Glu | Arg | Gly | Thr | Ile | Gly | Gly | |
| | | | 120 | | | | | 125 | | | | | 130 | | | |
| ACC | TGC | GTC | AAT | GTC | GGT | TGT | GTG | CCG | TCC | AAG | ATC | ATG | ATC | CGC | GCC | 486 |
| Thr | Cys | Val | Asn | Val | Gly | Cys | Val | Pro | Ser | Lys | Ile | Met | Ile | Arg | Ala | |
| | | | 135 | | | | | 140 | | | | | 145 | | | |
| GCC | CAT | ATC | GCC | CAT | CTG | CGC | CGG | GAA | AGC | CCG | TTC | GAT | GGC | GGC | ATC | 534 |
| Ala | His | Ile | Ala | His | Leu | Arg | Arg | Glu | Ser | Pro | Phe | Asp | Gly | Gly | Ile | |
| 150 | | | | | 155 | | | | | 160 | | | | | 165 | |
| GCC | GCT | ACC | ACG | CCG | ACC | ATC | CAG | CGC | ACG | GCG | CTG | CTG | GCC | CAG | CAG | 582 |
| Ala | Ala | Thr | Thr | Pro | Thr | Ile | Gln | Arg | Thr | Ala | Leu | Leu | Ala | Gln | Gln | |
| | | | | 170 | | | | | 175 | | | | | 180 | | |
| CAG | GCC | CGC | GTC | GAT | GAA | CTG | CGT | CAT | GCA | AAG | TAT | GAA | GGT | ATT | CTA | 630 |
| Gln | Ala | Arg | Val | Asp | Glu | Leu | Arg | His | Ala | Lys | Tyr | Glu | Gly | Ile | Leu | |
| | | | 185 | | | | | 190 | | | | | 195 | | | |
| GAA | GGT | AAC | CCA | GCC | ATC | ACT | GTG | CTT | CAT | GGC | TCT | GCA | CGT | TTC | AAG | 678 |
| Glu | Gly | Asn | Pro | Ala | Ile | Thr | Val | Leu | His | Gly | Ser | Ala | Arg | Phe | Lys | |
| | | | 200 | | | | | 205 | | | | | 210 | | | |
| GAC | AAC | CGT | AAC | CTC | ATT | GTT | CAA | CTC | AAC | GAC | GGC | GGC | GAG | CGC | GTG | 726 |
| Asp | Asn | Arg | Asn | Leu | Ile | Val | Gln | Leu | Asn | Asp | Gly | Gly | Glu | Arg | Val | |
| | | | 215 | | | | | 220 | | | | | 225 | | | |
| GTG | GCA | TTC | GAC | CGC | TGT | CTC | ATT | GCC | ACT | GGT | GCA | AGC | CCA | GCT | GTT | 774 |
| Val | Ala | Phe | Asp | Arg | Cys | Leu | Ile | Ala | Thr | Gly | Ala | Ser | Pro | Ala | Val | |
| | 230 | | | | | 235 | | | | | 240 | | | | | 245 |
| CCA | CCA | ATT | CCT | GGT | CTC | AAG | GAC | ACT | CCT | TAC | TGG | ACT | TCC | ACT | GAA | 822 |
| Pro | Pro | Ile | Pro | Gly | Leu | Lys | Asp | Thr | Pro | Tyr | Trp | Thr | Ser | Thr | Glu | |
| | | | | 250 | | | | | 255 | | | | | 260 | | |
| GCA | CTA | GTG | TCT | GAG | ACC | ATT | CCA | AAG | CGT | CTT | GCA | GTC | ATT | GGC | TCC | 870 |
| Ala | Leu | Val | Ser | Glu | Thr | Ile | Pro | Lys | Arg | Leu | Ala | Val | Ile | Gly | Ser | |
| | | | 265 | | | | | 270 | | | | | 275 | | | |
| TCT | GTG | GTG | GCT | CTT | GAA | CTT | GCC | CAG | GCC | TTT | GCA | CGT | CTT | GGT | GCT | 918 |
| Ser | Val | Val | Ala | Leu | Glu | Leu | Ala | Gln | Ala | Phe | Ala | Arg | Leu | Gly | Ala | |
| | | | 280 | | | | | 285 | | | | | 290 | | | |
| AAA | GTG | ACC | ATT | CTT | GCA | CGC | TCC | ACT | CTC | TTC | TTT | CGT | GAA | GAC | CCA | 966 |
| Lys | Val | Thr | Ile | Leu | Ala | Arg | Ser | Thr | Leu | Phe | Phe | Arg | Glu | Asp | Pro | |
| | 295 | | | | | 300 | | | | | 305 | | | | | |
| GCT | ATA | GGT | GAA | GCT | GTT | ACT | GCT | GCA | TTT | CGC | ATG | GAA | GGC | ATT | GAA | 1014 |
| Ala | Ile | Gly | Glu | Ala | Val | Thr | Ala | Ala | Phe | Arg | Met | Glu | Gly | Ile | Glu | |
| 310 | | | | | 315 | | | | | 320 | | | | | 325 | |

```
GTG CGT GAG CAT ACT CAA GCA AGC CAA GTT GCC TAT ATC AAT GGT GAA         1062
Val Arg Glu His Thr Gln Ala Ser Gln Val Ala Tyr Ile Asn Gly Glu
            330                 335                 340

GGT GAC GGT GAA TTC GTC CTA ACC ACT GCT CAT GGT GAA CTT CGT GCA         1110
Gly Asp Gly Glu Phe Val Leu Thr Thr Ala His Gly Glu Leu Arg Ala
                345                 350                 355

GAC AAA CTC CTT GTT GCA ACT GGT CGT GCA CCA AAC ACT CGC AAA CTG         1158
Asp Lys Leu Leu Val Ala Thr Gly Arg Ala Pro Asn Thr Arg Lys Leu
        360                 365                 370

GCA CTT GAT GCA ACT GGT GTG ACC CTT ACT CCA CAA GGT GCT ATT GTC         1206
Ala Leu Asp Ala Thr Gly Val Thr Leu Thr Pro Gln Gly Ala Ile Val
    375                 380                 385

ATC GAC CCC GGC ATG CGT ACA AGC GTG GAA CAC ATC TAC GCC GCA GGC         1254
Ile Asp Pro Gly Met Arg Thr Ser Val Glu His Ile Tyr Ala Ala Gly
390                 395                 400                 405

GAC TGC ACC GAC CAG CCG CAG TTC GTC TAT GTG GCG GCA GCG GCC GGC         1302
Asp Cys Thr Asp Gln Pro Gln Phe Val Tyr Val Ala Ala Ala Ala Gly
                410                 415                 420

ACT CGC GCC GCG ATC AAC ATG ACC GGC GGT GAC GCC GCC CTG AAC CTG         1350
Thr Arg Ala Ala Ile Asn Met Thr Gly Gly Asp Ala Ala Leu Asn Leu
            425                 430                 435

ACC GCG ATG CCG GCC GTG GTG TTC ACC GAC CCG CAA GTG GCG ACC GTA         1398
Thr Ala Met Pro Ala Val Val Phe Thr Asp Pro Gln Val Ala Thr Val
        440                 445                 450

GGC TAC AGC GAG GCG GAA GCG CAC CAT GAC GGC ATC AAA ACT GAT AGT         1446
Gly Tyr Ser Glu Ala Glu Ala His His Asp Gly Ile Lys Thr Asp Ser
    455                 460                 465

CGC ACG CTA ACG CTG GAC AAC GTG CCG CGC GCG CTC GCC AAC TTC GAC         1494
Arg Thr Leu Thr Leu Asp Asn Val Pro Arg Ala Leu Ala Asn Phe Asp
470                 475                 480                 485

ACG CGC GGC TTC ATC AAA CTG GTG GTT GAA GAA GGG AGC GGA CGA CTG         1542
Thr Arg Gly Phe Ile Lys Leu Val Val Glu Glu Gly Ser Gly Arg Leu
                490                 495                 500

ATC GGC GTC CAG GCA GTG GCC CCG GAA GCG GGC GAA CTG ATC CAG ACG         1590
Ile Gly Val Gln Ala Val Ala Pro Glu Ala Gly Glu Leu Ile Gln Thr
            505                 510                 515

GCC GCA CTG GCG ATT CGC AAC CGG ATG ACG GTG CAG GAA CTG GCC GAC         1638
Ala Ala Leu Ala Ile Arg Asn Arg Met Thr Val Gln Glu Leu Ala Asp
        520                 525                 530

CAG TTG TTC CCC TAC CTG ACG ATG GTC GAA GGG TTG AAG CTC GCG GCG         1686
Gln Leu Phe Pro Tyr Leu Thr Met Val Glu Gly Leu Lys Leu Ala Ala
    535                 540                 545

CAG ACC TTC AAC AAG GAT GTG AAG CAG CTT TCC TGC TGC GCC GGG TGA         1734
Gln Thr Phe Asn Lys Asp Val Lys Gln Leu Ser Cys Cys Ala Gly *
550                 555                 560                 565

GGCTGCAGGA ATTCGATA                                                      1752
```

( 2 ) INFORMATION FOR SEQ ID NO:14:

( i ) SEQUENCE CHARACTERISTICS:
        ( A ) LENGTH: 564 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Ser Thr Leu Lys Ile Thr Gly Met Thr Cys Asp Ser Cys Ala Val
1               5                   10                  15

His Val Lys Asp Ala Leu Glu Lys Val Pro Gly Val Gln Ser Ala Asp
            20                  25                  30
```

```
Val Ser Tyr Ala Lys Gly Ser Ala Lys Leu Ala Ile Glu Val Gly Thr
        35                  40                  45
Ser Pro Asp Ala Leu Thr Ala Ala Val Ala Gly Leu Gly Tyr Arg Ala
        50                  55                  60
Thr Leu Ala Asp Ala Pro Ser Val Ser Thr Pro Gly Gly Leu Leu Asp
65                      70                  75                  80
Lys Met Arg Asp Leu Leu Gly Arg Asn Asp Lys Thr Gly Ser Ser Gly
                    85                  90                  95
Ala Leu His Ile Ala Val Ile Gly Ser Gly Ala Ala Met Ala Ala
                100                 105                 110
Ala Leu Lys Ala Val Glu Gln Gly Ala Pro Val Thr Leu Ile Glu Arg
            115                 120                 125
Gly Thr Ile Gly Gly Thr Cys Val Asn Val Gly Cys Val Pro Ser Lys
        130                 135                 140
Ile Met Ile Arg Ala Ala His Ile Ala His Leu Arg Arg Glu Ser Pro
145                 150                 155                 160
Phe Asp Gly Gly Ile Ala Ala Thr Thr Pro Thr Ile Gln Arg Thr Ala
                    165                 170                 175
Leu Leu Ala Gln Gln Gln Ala Arg Val Asp Glu Leu Arg His Ala Lys
                180                 185                 190
Tyr Glu Gly Ile Leu Glu Gly Asn Pro Ala Ile Thr Val Leu His Gly
            195                 200                 205
Ser Ala Arg Phe Lys Asp Asn Arg Asn Leu Ile Val Gln Leu Asn Asp
        210                 215                 220
Gly Gly Glu Arg Val Val Ala Phe Asp Arg Cys Leu Ile Ala Thr Gly
225                 230                 235                 240
Ala Ser Pro Ala Val Pro Pro Ile Pro Gly Leu Lys Asp Thr Pro Tyr
                    245                 250                 255
Trp Thr Ser Thr Glu Ala Leu Val Ser Glu Thr Ile Pro Lys Arg Leu
                260                 265                 270
Ala Val Ile Gly Ser Ser Val Val Ala Leu Glu Leu Ala Gln Ala Phe
            275                 280                 285
Ala Arg Leu Gly Ala Lys Val Thr Ile Leu Ala Arg Ser Thr Leu Phe
        290                 295                 300
Phe Arg Glu Asp Pro Ala Ile Gly Glu Ala Val Thr Ala Ala Phe Arg
305                 310                 315                 320
Met Glu Gly Ile Glu Val Arg Glu His Thr Gln Ala Ser Gln Val Ala
                    325                 330                 335
Tyr Ile Asn Gly Glu Gly Asp Gly Glu Phe Val Leu Thr Thr Ala His
                340                 345                 350
Gly Glu Leu Arg Ala Asp Lys Leu Leu Val Ala Thr Gly Arg Ala Pro
            355                 360                 365
Asn Thr Arg Lys Leu Ala Leu Asp Ala Thr Gly Val Thr Leu Thr Pro
        370                 375                 380
Gln Gly Ala Ile Val Ile Asp Pro Gly Met Arg Thr Ser Val Glu His
385                 390                 395                 400
Ile Tyr Ala Ala Gly Asp Cys Thr Asp Gln Pro Gln Phe Val Tyr Val
                    405                 410                 415
Ala Ala Ala Ala Gly Thr Arg Ala Ala Ile Asn Met Thr Gly Gly Asp
                420                 425                 430
Ala Ala Leu Asn Leu Thr Ala Met Pro Ala Val Val Phe Thr Asp Pro
            435                 440                 445
Gln Val Ala Thr Val Gly Tyr Ser Glu Ala Glu Ala His His Asp Gly
        450                 455                 460
```

```
Ile Lys Thr Asp Ser Arg Thr Leu Thr Leu Asp Asn Val Pro Arg Ala
465                 470                 475                 480

Leu Ala Asn Phe Asp Thr Arg Gly Phe Ile Lys Leu Val Val Glu Glu
                485                 490                 495

Gly Ser Gly Arg Leu Ile Gly Val Gln Ala Val Ala Pro Glu Ala Gly
            500                 505                 510

Glu Leu Ile Gln Thr Ala Ala Leu Ala Ile Arg Asn Arg Met Thr Val
            515                 520                 525

Gln Glu Leu Ala Asp Gln Leu Phe Pro Tyr Leu Thr Met Val Glu Gly
        530                 535                 540

Leu Lys Leu Ala Ala Gln Thr Phe Asn Lys Asp Val Lys Gln Leu Ser
545                 550                 555                 560

Cys Cys Ala Gly
            565
```

( 2 ) INFORMATION FOR SEQ ID NO:15:

( i ) SEQUENCE CHARACTERISTICS:
        ( A ) LENGTH: 1752 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="Mutagenized merApe9"

( i i i ) HYPOTHETICAL: NO ( i x ) FEATURE:
        ( A ) NAME/KEY: CDS
        ( B ) LOCATION: 40..1734

( i x ) FEATURE:
        ( A ) NAME/KEY: mat_peptide
        ( B ) LOCATION: 40..1731

( x i ) SEQUENCE DESCRIPTION: SEQ ID NO:15:

```
CTAGAACTAG TGGATCCCTA GATCTAAGAA GGAACCACA ATG AGC ACT CTC AAA         54
                                           Met Ser Thr Leu Lys
                                           1               5

ATC ACC GGC ATG ACT TGC GAC TCG TGC GCA GTG CAT GTC AAG GAC GCC       102
Ile Thr Gly Met Thr Cys Asp Ser Cys Ala Val His Val Lys Asp Ala
        10                  15                  20

CTG GAG AAA GTG CCC GGC GTG CAA TCA GCG GAT GTC TCC TAC GCC AAG       150
Leu Glu Lys Val Pro Gly Val Gln Ser Ala Asp Val Ser Tyr Ala Lys
            25                  30                  35

GGC AGC GCC AAG CTC GCC ATT GAG GTC GGC ACG TCA CCC GAC GCG CTG       198
Gly Ser Ala Lys Leu Ala Ile Glu Val Gly Thr Ser Pro Asp Ala Leu
        40                  45                  50

ACG GCC GCT GTA GCT GGA CTC GGT TAT CGG GCC ACG CTG GCC GAT GCC       246
Thr Ala Ala Val Ala Gly Leu Gly Tyr Arg Ala Thr Leu Ala Asp Ala
        55                  60                  65

CCC TCA GTT TCG ACG CCG GGC GGA TTG CTC GAC AAG ATG CGC GAT CTG       294
Pro Ser Val Ser Thr Pro Gly Gly Leu Leu Asp Lys Met Arg Asp Leu
70              75                  80                      85

CTG GGC AGA AAC GAC AAG ACG GGT AGC AGC GGC GCA TTG CAT ATC GCC       342
Leu Gly Arg Asn Asp Lys Thr Gly Ser Ser Gly Ala Leu His Ile Ala
                90                  95                  100

GTC ATC GGC AGC GGC GGG GCC GCG ATG GCA GCG GCG CTG AAG GCC GTC       390
Val Ile Gly Ser Gly Gly Ala Ala Met Ala Ala Ala Leu Lys Ala Val
            105                 110                 115

GAG CAA GGC GCA CCT GTC ACG CTG ATC GAG CGC GGC ACC ATC GGC GGC       438
```

| | | | | | | | | | | | | | | | | |
|---|---|---|---|---|---|---|---|---|---|---|---|---|---|---|---|---|
| | Glu | Gln | Gly | Ala | Pro | Val | Thr | Leu | Ile | Glu | Arg | Gly | Thr | Ile | Gly | Gly |
| | | | 120 | | | | | 125 | | | | | 130 | | | |

| | | | | | | | | | | | | | | | | | |
|---|---|---|---|---|---|---|---|---|---|---|---|---|---|---|---|---|---|
| ACC | TGC | GTC | AAT | GTC | GGT | TGT | GTG | CCG | TCC | AAG | ATC | ATG | ATC | CGC | GCC | | 486 |
| Thr | Cys | Val | Asn | Val | Gly | Cys | Val | Pro | Ser | Lys | Ile | Met | Ile | Arg | Ala | | |
| | 135 | | | | 140 | | | | | 145 | | | | | | | |

| | | | | | | | | | | | | | | | | | |
|---|---|---|---|---|---|---|---|---|---|---|---|---|---|---|---|---|---|
| GCC | CAT | ATC | GCC | CAT | CTG | CGC | CGG | GAA | AGC | CCG | TTC | GAT | GGC | GGC | ATC | | 534 |
| Ala | His | Ile | Ala | His | Leu | Arg | Arg | Glu | Ser | Pro | Phe | Asp | Gly | Gly | Ile | | |
| 150 | | | | | 155 | | | | | 160 | | | | | 165 | | |

| | | | | | | | | | | | | | | | | | |
|---|---|---|---|---|---|---|---|---|---|---|---|---|---|---|---|---|---|
| GCC | GCT | ACC | ACG | CCG | ACC | ATC | CAG | CGC | ACG | GCG | CTG | CTG | GCC | CAG | CAG | | 582 |
| Ala | Ala | Thr | Thr | Pro | Thr | Ile | Gln | Arg | Thr | Ala | Leu | Leu | Ala | Gln | Gln | | |
| | | | | 170 | | | | | 175 | | | | | 180 | | | |

| | | | | | | | | | | | | | | | | | |
|---|---|---|---|---|---|---|---|---|---|---|---|---|---|---|---|---|---|
| CAG | GCC | CGC | GTC | GAT | GAA | CTG | CGC | CAC | GCC | AAG | TAC | GAA | GGC | ATC | TTG | | 630 |
| Gln | Ala | Arg | Val | Asp | Glu | Leu | Arg | His | Ala | Lys | Tyr | Glu | Gly | Ile | Leu | | |
| | | | 185 | | | | | 190 | | | | | 195 | | | | |

| | | | | | | | | | | | | | | | | | |
|---|---|---|---|---|---|---|---|---|---|---|---|---|---|---|---|---|---|
| GAG | GGC | AAT | CCG | GCG | ATC | ACT | GTG | CTG | CAC | GGC | TCC | GCC | CGC | TTT | AAG | | 678 |
| Glu | Gly | Asn | Pro | Ala | Ile | Thr | Val | Leu | His | Gly | Ser | Ala | Arg | Phe | Lys | | |
| | | 200 | | | | | 205 | | | | | 210 | | | | | |

| | | | | | | | | | | | | | | | | | |
|---|---|---|---|---|---|---|---|---|---|---|---|---|---|---|---|---|---|
| GAC | AAT | CGC | AAC | CTG | ATC | GTG | CAA | CTC | AAC | GAC | GGC | GGC | GAG | CGC | GTG | | 726 |
| Asp | Asn | Arg | Asn | Leu | Ile | Val | Gln | Leu | Asn | Asp | Gly | Gly | Glu | Arg | Val | | |
| | 215 | | | | 220 | | | | | 225 | | | | | | | |

| | | | | | | | | | | | | | | | | | |
|---|---|---|---|---|---|---|---|---|---|---|---|---|---|---|---|---|---|
| GTG | GCA | TTC | GAC | CGC | TGC | CTG | ATC | GCC | ACC | GGC | GCG | AGC | CCG | GCC | GTG | | 774 |
| Val | Ala | Phe | Asp | Arg | Cys | Leu | Ile | Ala | Thr | Gly | Ala | Ser | Pro | Ala | Val | | |
| 230 | | | | | 235 | | | | | 240 | | | | | 245 | | |

| | | | | | | | | | | | | | | | | | |
|---|---|---|---|---|---|---|---|---|---|---|---|---|---|---|---|---|---|
| CCG | CCG | ATT | CCC | GGC | CTG | AAA | GAC | ACT | CCG | TAC | TGG | ACT | TCC | ACT | GAA | | 822 |
| Pro | Pro | Ile | Pro | Gly | Leu | Lys | Asp | Thr | Pro | Tyr | Trp | Thr | Ser | Thr | Glu | | |
| | | | | 250 | | | | | 255 | | | | | 260 | | | |

| | | | | | | | | | | | | | | | | | |
|---|---|---|---|---|---|---|---|---|---|---|---|---|---|---|---|---|---|
| GCG | CTG | GTC | AGC | GAG | ACG | ATT | CCT | AAG | CGC | CTG | GCC | GTG | ATT | GGC | TCA | | 870 |
| Ala | Leu | Val | Ser | Glu | Thr | Ile | Pro | Lys | Arg | Leu | Ala | Val | Ile | Gly | Ser | | |
| | | | 265 | | | | | 270 | | | | | 275 | | | | |

| | | | | | | | | | | | | | | | | | |
|---|---|---|---|---|---|---|---|---|---|---|---|---|---|---|---|---|---|
| TCA | GTG | CTG | GCG | CTT | GAA | CTT | GCC | CAG | GCC | TTT | GCA | CGT | CTT | GGT | GCT | | 918 |
| Ser | Val | Leu | Ala | Leu | Glu | Leu | Ala | Gln | Ala | Phe | Ala | Arg | Leu | Gly | Ala | | |
| | | 280 | | | | | 285 | | | | | 290 | | | | | |

| | | | | | | | | | | | | | | | | | |
|---|---|---|---|---|---|---|---|---|---|---|---|---|---|---|---|---|---|
| AAA | GTG | ACC | ATT | CTT | GCA | CGC | TCC | ACT | CTC | TTC | TTT | CGT | GAA | GAC | CCA | | 966 |
| Lys | Val | Thr | Ile | Leu | Ala | Arg | Ser | Thr | Leu | Phe | Phe | Arg | Glu | Asp | Pro | | |
| | 295 | | | | 300 | | | | | 305 | | | | | | | |

| | | | | | | | | | | | | | | | | | |
|---|---|---|---|---|---|---|---|---|---|---|---|---|---|---|---|---|---|
| GCT | ATA | GGT | GAA | GCT | GTT | ACT | GCT | GCA | TTT | CGC | ATG | GAA | GGC | ATT | GAA | | 1014 |
| Ala | Ile | Gly | Glu | Ala | Val | Thr | Ala | Ala | Phe | Arg | Met | Glu | Gly | Ile | Glu | | |
| 310 | | | | | 315 | | | | | 320 | | | | | 325 | | |

| | | | | | | | | | | | | | | | | | |
|---|---|---|---|---|---|---|---|---|---|---|---|---|---|---|---|---|---|
| GTG | CGT | GAG | CAT | ACT | CAA | GCA | AGC | CAA | GTT | GCC | TAT | ATC | AAT | GGT | GAA | | 1062 |
| Val | Arg | Glu | His | Thr | Gln | Ala | Ser | Gln | Val | Ala | Tyr | Ile | Asn | Gly | Glu | | |
| | | | | 330 | | | | | 335 | | | | | 340 | | | |

| | | | | | | | | | | | | | | | | | |
|---|---|---|---|---|---|---|---|---|---|---|---|---|---|---|---|---|---|
| GGG | GAC | GGC | GAA | TTC | GTG | CTC | ACC | ACG | GCG | CAC | GGC | GAA | CTG | CGC | GCC | | 1110 |
| Gly | Asp | Gly | Glu | Phe | Val | Leu | Thr | Thr | Ala | His | Gly | Glu | Leu | Arg | Ala | | |
| | | | 345 | | | | | 350 | | | | | 355 | | | | |

| | | | | | | | | | | | | | | | | | |
|---|---|---|---|---|---|---|---|---|---|---|---|---|---|---|---|---|---|
| GAC | AAG | CTG | CTG | GTC | GCC | ACC | GGC | CGC | GCG | CCC | AAC | ACA | CGC | AAG | CTG | | 1158 |
| Asp | Lys | Leu | Leu | Val | Ala | Thr | Gly | Arg | Ala | Pro | Asn | Thr | Arg | Lys | Leu | | |
| | | 360 | | | | | 365 | | | | | 370 | | | | | |

| | | | | | | | | | | | | | | | | | |
|---|---|---|---|---|---|---|---|---|---|---|---|---|---|---|---|---|---|
| GCA | CTG | GAT | GCG | ACG | GGC | GTC | ACG | CTC | ACC | CCC | CAA | GGC | GCT | ATC | GTC | | 1206 |
| Ala | Leu | Asp | Ala | Thr | Gly | Val | Thr | Leu | Thr | Pro | Gln | Gly | Ala | Ile | Val | | |
| | 375 | | | | 380 | | | | | 385 | | | | | | | |

| | | | | | | | | | | | | | | | | | |
|---|---|---|---|---|---|---|---|---|---|---|---|---|---|---|---|---|---|
| ATC | GAC | CCC | GGC | ATG | CGT | ACA | AGC | GTG | GAA | CAC | ATC | TAC | GCC | GCA | GGC | | 1254 |
| Ile | Asp | Pro | Gly | Met | Arg | Thr | Ser | Val | Glu | His | Ile | Tyr | Ala | Ala | Gly | | |
| 390 | | | | | 395 | | | | | 400 | | | | | 405 | | |

| | | | | | | | | | | | | | | | | | |
|---|---|---|---|---|---|---|---|---|---|---|---|---|---|---|---|---|---|
| GAC | TGC | ACC | GAC | CAG | CCG | CAG | TTC | GTC | TAT | GTG | GCG | GCA | GCG | GGC | | | 1302 |
| Asp | Cys | Thr | Asp | Gln | Pro | Gln | Phe | Val | Tyr | Val | Ala | Ala | Ala | Gly | | | |
| | | | | 410 | | | | | 415 | | | | | 420 | | | |

| | | | | | | | | | | | | | | | | | |
|---|---|---|---|---|---|---|---|---|---|---|---|---|---|---|---|---|---|
| ACT | CGC | GCC | GCG | ATC | AAC | ATG | ACC | GGC | GGT | GAC | GCC | GCC | CTG | AAC | CTG | | 1350 |
| Thr | Arg | Ala | Ala | Ile | Asn | Met | Thr | Gly | Gly | Asp | Ala | Ala | Leu | Asn | Leu | | |
| | | | | 425 | | | | | 430 | | | | | 435 | | | |

| | | | | | | | | | | | | | | | | | |
|---|---|---|---|---|---|---|---|---|---|---|---|---|---|---|---|---|---|
| ACC | GCG | ATG | CCG | GCC | GTG | GTG | TTC | ACC | GAC | CCG | CAA | GTG | GCG | ACC | GTA | | 1398 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Thr | Ala | Met | Pro | Ala | Val | Val | Phe | Thr | Asp | Pro | Gln | Val | Ala | Thr | Val |      |
|     |     | 440 |     |     |     | 445 |     |     |     | 450 |     |     |     |     |     |      |
| GGC | TAC | AGC | GAG | GCG | GAA | GCG | CAC | CAT | GAC | GGC | ATC | AAA | ACT | GAT | AGT | 1446 |
| Gly | Tyr | Ser | Glu | Ala | Glu | Ala | His | His | Asp | Gly | Ile | Lys | Thr | Asp | Ser |      |
|     |     | 455 |     |     |     | 460 |     |     |     | 465 |     |     |     |     |     |      |
| CGC | ACG | CTA | ACG | CTG | GAC | AAC | GTG | CCG | CGC | GCG | CTC | GCC | AAC | TTC | GAC | 1494 |
| Arg | Thr | Leu | Thr | Leu | Asp | Asn | Val | Pro | Arg | Ala | Leu | Ala | Asn | Phe | Asp |      |
| 470 |     |     |     |     | 475 |     |     |     |     | 480 |     |     |     |     | 485 |      |
| ACG | CGC | GGC | TTC | ATC | AAA | CTG | GTG | GTT | GAA | GAA | GGG | AGC | GGA | CGA | CTG | 1542 |
| Thr | Arg | Gly | Phe | Ile | Lys | Leu | Val | Val | Glu | Glu | Gly | Ser | Gly | Arg | Leu |      |
|     |     |     |     | 490 |     |     |     |     | 495 |     |     |     |     | 500 |     |      |
| ATC | GGC | GTC | CAG | GCA | GTG | GCC | CCG | GAA | GCG | GGC | GAA | CTG | ATC | CAG | ACG | 1590 |
| Ile | Gly | Val | Gln | Ala | Val | Ala | Pro | Glu | Ala | Gly | Glu | Leu | Ile | Gln | Thr |      |
|     |     |     | 505 |     |     |     |     | 510 |     |     |     |     | 515 |     |     |      |
| GCC | GCA | CTG | GCG | ATT | CGC | AAC | CGG | ATG | ACG | GTG | CAG | GAA | CTG | GCC | GAC | 1638 |
| Ala | Ala | Leu | Ala | Ile | Arg | Asn | Arg | Met | Thr | Val | Gln | Glu | Leu | Ala | Asp |      |
|     |     | 520 |     |     |     |     | 525 |     |     |     |     | 530 |     |     |     |      |
| CAG | TTG | TTC | CCC | TAC | CTG | ACG | ATG | GTC | GAA | GGG | TTG | AAG | CTC | GCG | GCG | 1686 |
| Gln | Leu | Phe | Pro | Tyr | Leu | Thr | Met | Val | Glu | Gly | Leu | Lys | Leu | Ala | Ala |      |
|     | 535 |     |     |     |     | 540 |     |     |     |     | 545 |     |     |     |     |      |
| CAG | ACC | TTC | AAC | AAG | GAT | GTG | AAG | CAG | CTT | TCC | TGC | TGC | GCC | GGG | TGA | 1734 |
| Gln | Thr | Phe | Asn | Lys | Asp | Val | Lys | Gln | Leu | Ser | Cys | Cys | Ala | Gly | *   |      |
| 550 |     |     |     |     | 555 |     |     |     |     | 560 |     |     |     |     | 565 |      |

GGCTGCAGGA ATTCGATA      1752

(2) INFORMATION FOR SEQ ID NO:16:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:16:

|     |     |     |     |     |     |     |     |     |     |     |     |     |     |     |
| --- | --- | --- | --- | --- | --- | --- | --- | --- | --- | --- | --- | --- | --- | --- |
| Met | Ser | Thr | Leu | Lys | Ile | Thr | Gly | Met | Thr | Cys | Asp | Ser | Cys | Ala | Val |
| 1   |     |     |     | 5   |     |     |     |     | 10  |     |     |     |     | 15  |
| His | Val | Lys | Asp | Ala | Leu | Glu | Lys | Val | Pro | Gly | Val | Gln | Ser | Ala | Asp |
|     |     |     | 20  |     |     |     |     | 25  |     |     |     |     | 30  |     |
| Val | Ser | Tyr | Ala | Lys | Gly | Ser | Ala | Lys | Leu | Ala | Ile | Glu | Val | Gly | Thr |
|     |     | 35  |     |     |     |     | 40  |     |     |     |     | 45  |     |     |
| Ser | Pro | Asp | Ala | Leu | Thr | Ala | Ala | Val | Ala | Gly | Leu | Gly | Tyr | Arg | Ala |
|     | 50  |     |     |     |     | 55  |     |     |     |     | 60  |     |     |     |
| Thr | Leu | Ala | Asp | Ala | Pro | Ser | Val | Ser | Thr | Pro | Gly | Gly | Leu | Leu | Asp |
| 65  |     |     |     |     | 70  |     |     |     |     | 75  |     |     |     |     | 80  |
| Lys | Met | Arg | Asp | Leu | Leu | Gly | Arg | Asn | Asp | Lys | Thr | Gly | Ser | Ser | Gly |
|     |     |     |     | 85  |     |     |     |     | 90  |     |     |     |     | 95  |
| Ala | Leu | His | Ile | Ala | Val | Ile | Gly | Ser | Gly | Ala | Ala | Met | Ala | Ala |
|     |     |     | 100 |     |     |     |     | 105 |     |     |     |     | 110 |     |
| Ala | Leu | Lys | Ala | Val | Glu | Gln | Gly | Ala | Pro | Val | Thr | Leu | Ile | Glu | Arg |
|     |     | 115 |     |     |     |     | 120 |     |     |     |     | 125 |     |     |
| Gly | Thr | Ile | Gly | Gly | Thr | Cys | Val | Asn | Val | Gly | Cys | Val | Pro | Ser | Lys |
|     | 130 |     |     |     |     | 135 |     |     |     |     | 140 |     |     |     |
| Ile | Met | Ile | Arg | Ala | Ala | His | Ile | Ala | His | Leu | Arg | Arg | Glu | Ser | Pro |
| 145 |     |     |     |     | 150 |     |     |     |     | 155 |     |     |     |     | 160 |
| Phe | Asp | Gly | Gly | Ile | Ala | Ala | Thr | Thr | Pro | Thr | Ile | Gln | Arg | Thr | Ala |
|     |     |     |     | 165 |     |     |     |     | 170 |     |     |     |     | 175 |
| Leu | Leu | Ala | Gln | Gln | Gln | Ala | Arg | Val | Asp | Glu | Leu | Arg | His | Ala | Lys |
|     |     |     | 180 |     |     |     |     | 185 |     |     |     |     | 190 |     |

```
Tyr Glu Gly Ile Leu Glu Gly Asn Pro Ala Ile Thr Val Leu His Gly
        195                 200                 205

Ser Ala Arg Phe Lys Asp Asn Arg Asn Leu Ile Val Gln Leu Asn Asp
    210                 215                 220

Gly Gly Glu Arg Val Val Ala Phe Asp Arg Cys Leu Ile Ala Thr Gly
225                 230                 235                 240

Ala Ser Pro Ala Val Pro Pro Ile Pro Gly Leu Lys Asp Thr Pro Tyr
                245                 250                 255

Trp Thr Ser Thr Glu Ala Leu Val Ser Glu Thr Ile Pro Lys Arg Leu
            260                 265                 270

Ala Val Ile Gly Ser Ser Val Leu Ala Leu Glu Leu Ala Gln Ala Phe
        275                 280                 285

Ala Arg Leu Gly Ala Lys Val Thr Ile Leu Ala Arg Ser Thr Leu Phe
    290                 295                 300

Phe Arg Glu Asp Pro Ala Ile Gly Glu Ala Val Thr Ala Ala Phe Arg
305                 310                 315                 320

Met Glu Gly Ile Glu Val Arg Glu His Thr Gln Ala Ser Gln Val Ala
                325                 330                 335

Tyr Ile Asn Gly Glu Gly Asp Gly Glu Phe Val Leu Thr Thr Ala His
            340                 345                 350

Gly Glu Leu Arg Ala Asp Lys Leu Leu Val Ala Thr Gly Arg Ala Pro
        355                 360                 365

Asn Thr Arg Lys Leu Ala Leu Asp Ala Thr Gly Val Thr Leu Thr Pro
370                 375                 380

Gln Gly Ala Ile Val Ile Asp Pro Gly Met Arg Thr Ser Val Glu His
385                 390                 395                 400

Ile Tyr Ala Ala Gly Asp Cys Thr Asp Gln Pro Gln Phe Val Tyr Val
                405                 410                 415

Ala Ala Ala Ala Gly Thr Arg Ala Ala Ile Asn Met Thr Gly Gly Asp
            420                 425                 430

Ala Ala Leu Asn Leu Thr Ala Met Pro Ala Val Val Phe Thr Asp Pro
        435                 440                 445

Gln Val Ala Thr Val Gly Tyr Ser Glu Ala Glu Ala His His Asp Gly
    450                 455                 460

Ile Lys Thr Asp Ser Arg Thr Leu Thr Leu Asp Asn Val Pro Arg Ala
465                 470                 475                 480

Leu Ala Asn Phe Asp Thr Arg Gly Phe Ile Lys Leu Val Val Glu Glu
                485                 490                 495

Gly Ser Gly Arg Leu Ile Gly Val Gln Ala Val Ala Pro Glu Ala Gly
            500                 505                 510

Glu Leu Ile Gln Thr Ala Ala Leu Ala Ile Arg Asn Arg Met Thr Val
        515                 520                 525

Gln Glu Leu Ala Asp Gln Leu Phe Pro Tyr Leu Thr Met Val Glu Gly
    530                 535                 540

Leu Lys Leu Ala Ala Gln Thr Phe Asn Lys Asp Val Lys Gln Leu Ser
545                 550                 555                 560

Cys Cys Ala Gly
                565
```

( 2 ) INFORMATION FOR SEQ ID NO:17:

( i ) SEQUENCE CHARACTERISTICS:
        ( A ) LENGTH: 58 base pairs
        ( B ) TYPE: nucleic acid
        ( C ) STRANDEDNESS: single 5,668,294

63                                                                              64
-continued ( D ) TOPOLOGY: linear ( i i ) MOLECULE TYPE: other nucleic acid
    ( A ) DESCRIPTION: /desc ="Oligonucleotide"

( i i i ) HYPOTHETICAL: NO ( i v ) ANTI-SENSE: NO ( x i ) SEQUENCE DESCRIPTION: SEQ ID NO:17:

```
CGCGTCGGAT CCAGAATTCG TCGACTAACC AGGAGCCACA ATGAAGCTCG CCCCATAT         58
```

( 2 ) INFORMATION FOR SEQ ID NO:18:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( x i ) SEQUENCE DESCRIPTION: SEQ ID NO:18:

```
CGTATCGGAT CCGAATTCAA GCTTATCACG GTGTCCATAG ATGA                        44
```

( 2 ) INFORMATION FOR SEQ ID NO:19:

( i ) SEQUENCE CHARACTERISTICS:
        ( A ) LENGTH: 1752 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="Mutagenized merApe47"

( i i i ) HYPOTHETICAL: NO ( i x ) FEATURE:
        ( A ) NAME/KEY: CDS
        ( B ) LOCATION: 40..1734

( i x ) FEATURE:
        ( A ) NAME/KEY: mat_peptide
        ( B ) LOCATION: 40..1731

( x i ) SEQUENCE DESCRIPTION: SEQ ID NO:19:

```
CTAGAACTAG TGGATCCCTA GATCTAAGAA GGAACCACA ATG AGC ACT CTC AAA          54
                                            Met Ser Thr Leu Lys
                                             1               5

ATC ACC GGC ATG ACT TGC GAC TCG TGC GCA GTG CAT GTC AAG GAC GCC        102
Ile Thr Gly Met Thr Cys Asp Ser Cys Ala Val His Val Lys Asp Ala
             10                  15                  20

CTG GAG AAA GTG CCC GGC GTG CAA TCA GCG GAT GTC TCC TAC GCC AAG        150
Leu Glu Lys Val Pro Gly Val Gln Ser Ala Asp Val Ser Tyr Ala Lys
         25                  30                  35

GGC AGC GCC AAG CTC GCC ATT GAG GTC GGC ACG TCA CCC GAC GCG CTG        198
Gly Ser Ala Lys Leu Ala Ile Glu Val Gly Thr Ser Pro Asp Ala Leu
         40                  45                  50

ACG GCC GCT GTA GCT GGA CTC GGT TAT CGG GCC ACG CTG GCC GAT GCC        246
Thr Ala Ala Val Ala Gly Leu Gly Tyr Arg Ala Thr Leu Ala Asp Ala
     55                  60                  65

CCC TCA GTT TCG ACG CCG GGC GGA TTG CTC GAC AAG ATG CGC GAT CTG        294
Pro Ser Val Ser Thr Pro Gly Gly Leu Leu Asp Lys Met Arg Asp Leu
 70                  75                  80                  85

CTG GGC AGA AAC GAC AAG ACG GGT AGC AGC GGC GCA TTG CAT ATC GCC        342
```

| | | | | | | | | | | | | | | |
|---|---|---|---|---|---|---|---|---|---|---|---|---|---|---|
| Leu | Gly | Arg | Asn | Asp | Lys | Thr | Gly | Ser | Ser | Gly | Ala | Leu | His | Ile | Ala |
| | | | | 90 | | | | | 95 | | | | | 100 | |

```
GTC ATC GGC AGC GGC GGG GCC GCG ATG GCA GCG GCG CTG AAG GCC GTC       390
Val Ile Gly Ser Gly Gly Ala Ala Met Ala Ala Ala Leu Lys Ala Val
            105             110             115

GAG CAA GGC GCA CCT GTC ACG CTG ATC GAG CGC GGC ACC ATC GGC GGC       438
Glu Gln Gly Ala Pro Val Thr Leu Ile Glu Arg Gly Thr Ile Gly Gly
        120             125             130

ACC TGT GTT AAT GTT GGT TGT GTG CCG AGC AAG ATC ATG ATT CGT GCT       486
Thr Cys Val Asn Val Gly Cys Val Pro Ser Lys Ile Met Ile Arg Ala
    135             140             145

GCT CAC ATT GCT CAT CTT CGT CGT GAA TCT CCA TTT GAT GGT GGC ATT       534
Ala His Ile Ala His Leu Arg Arg Glu Ser Pro Phe Asp Gly Gly Ile
150             155             160             165

GCT GCA ACC ACT CCA ACC ATT CAA CGT ACT GCA CTC CTT GCA CAA CAA       582
Ala Ala Thr Thr Pro Thr Ile Gln Arg Thr Ala Leu Leu Ala Gln Gln
            170             175             180

CAA GCA CGT GTT GAT GAA CTT CGT CAT GCA AAG TAT GAA GGT ATT CTA       630
Gln Ala Arg Val Asp Glu Leu Arg His Ala Lys Tyr Glu Gly Ile Leu
        185             190             195

GAA GGT AAC CCA GCC ATC ACT GTG CTT CAT GGC TCT GCA CGT TTC AAG       678
Glu Gly Asn Pro Ala Ile Thr Val Leu His Gly Ser Ala Arg Phe Lys
    200             205             210

GAC AAC CGT AAC CTC ATT GTT CAA CTC AAC GAC GGC GGC GAG CGC GTG       726
Asp Asn Arg Asn Leu Ile Val Gln Leu Asn Asp Gly Gly Glu Arg Val
215             220             225

GTG GCA TTC GAC CGC TGT CTC ATT GCC ACT GGT GCA AGC CCA GCT GTT       774
Val Ala Phe Asp Arg Cys Leu Ile Ala Thr Gly Ala Ser Pro Ala Val
230             235             240             245

CCA CCA ATT CCT GGT CTC AAG GAC ACT CCT TAC TGG ACT TCC ACT GAA       822
Pro Pro Ile Pro Gly Leu Lys Asp Thr Pro Tyr Trp Thr Ser Thr Glu
            250             255             260

GCA CTA GTG TCT GAG ACC ATT CCA AAG CGT CTT GCA GTC ATT GGC TCC       870
Ala Leu Val Ser Glu Thr Ile Pro Lys Arg Leu Ala Val Ile Gly Ser
        265             270             275

TCT GTG GTG GCT CTT GAA CTT GCC CAG GCC TTT GCA CGT CTT GGT GCT       918
Ser Val Val Ala Leu Glu Leu Ala Gln Ala Phe Ala Arg Leu Gly Ala
    280             285             290

AAA GTG ACC ATT CTT GCA CGC TCC ACT CTC TTC TTT CGT GAA GAC CCA       966
Lys Val Thr Ile Leu Ala Arg Ser Thr Leu Phe Phe Arg Glu Asp Pro
295             300             305

GCT ATA GGT GAA GCT GTT ACT GCT GCA TTT CGC ATG GAA GGC ATT GAA      1014
Ala Ile Gly Glu Ala Val Thr Ala Ala Phe Arg Met Glu Gly Ile Glu
310             315             320             325

GTG CGT GAG CAT ACT CAA GCA AGC CAA GTT GCC TAT ATC AAT GGT GAA      1062
Val Arg Glu His Thr Gln Ala Ser Gln Val Ala Tyr Ile Asn Gly Glu
            330             335             340

GGT GAC GGT GAA TTC GTC CTA ACC ACT GCT CAT GGT GAA CTT CGT GCA      1110
Gly Asp Gly Glu Phe Val Leu Thr Thr Ala His Gly Glu Leu Arg Ala
        345             350             355

GAC AAA CTC CTT GTT GCA ACT GGT CGT GCA CCA AAC ACT CGC AAA CTG      1158
Asp Lys Leu Leu Val Ala Thr Gly Arg Ala Pro Asn Thr Arg Lys Leu
    360             365             370

GCA CTT GAT GCA ACT GGT GTG ACC CTT ACT CCA CAA GGT GCT ATT GTC      1206
Ala Leu Asp Ala Thr Gly Val Thr Leu Thr Pro Gln Gly Ala Ile Val
375             380             385

ATC GAC CCC GGC ATG CGT ACA AGC GTG GAA CAC ATC TAC GCC GCA GGC      1254
Ile Asp Pro Gly Met Arg Thr Ser Val Glu His Ile Tyr Ala Ala Gly
390             395             400             405

GAC TGC ACC GAC CAG CCG CAG TTC GTC TAT GTG GCG GCA GCG GCC GGC      1302
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Asp | Cys | Thr | Asp | Gln | Pro | Gln | Phe | Val | Tyr | Val | Ala | Ala | Ala | Ala | Gly | |
|     |     |     |     | 410 |     |     |     | 415 |     |     |     |     | 420 |     |     | |
| ACT | CGC | GCC | GCG | ATC | AAC | ATG | ACC | GGC | GGT | GAC | GCC | GCC | CTG | AAC | CTG | 1350 |
| Thr | Arg | Ala | Ala | Ile | Asn | Met | Thr | Gly | Gly | Asp | Ala | Ala | Leu | Asn | Leu | |
|     |     |     | 425 |     |     |     | 430 |     |     |     |     | 435 |     |     |     | |
| ACC | GCG | ATG | CCG | GCC | GTG | GTG | TTC | ACC | GAC | CCG | CAA | GTG | GCG | ACC | GTA | 1398 |
| Thr | Ala | Met | Pro | Ala | Val | Val | Phe | Thr | Asp | Pro | Gln | Val | Ala | Thr | Val | |
|     |     | 440 |     |     |     |     | 445 |     |     |     | 450 |     |     |     |     | |
| GGC | TAC | AGC | GAG | GCG | GAA | GCG | CAC | CAT | GAC | GGC | ATC | AAA | ACT | GAT | AGT | 1446 |
| Gly | Tyr | Ser | Glu | Ala | Glu | Ala | His | His | Asp | Gly | Ile | Lys | Thr | Asp | Ser | |
|     | 455 |     |     |     | 460 |     |     |     |     | 465 |     |     |     |     |     | |
| CGC | ACG | CTA | ACG | CTG | GAC | AAC | GTG | CCG | CGC | GCG | CTC | GCC | AAC | TTC | GAC | 1494 |
| Arg | Thr | Leu | Thr | Leu | Asp | Asn | Val | Pro | Arg | Ala | Leu | Ala | Asn | Phe | Asp | |
| 470 |     |     |     |     | 475 |     |     |     |     | 480 |     |     |     |     | 485 | |
| ACG | CGC | GGC | TTC | ATC | AAA | CTG | GTG | GTT | GAA | GAA | GGG | AGC | GGA | CGA | CTG | 1542 |
| Thr | Arg | Gly | Phe | Ile | Lys | Leu | Val | Val | Glu | Glu | Gly | Ser | Gly | Arg | Leu | |
|     |     |     |     | 490 |     |     |     |     | 495 |     |     |     |     | 500 |     | |
| ATC | GGC | GTC | CAG | GCA | GTG | GCC | CCG | GAA | GCG | GGC | GAA | CTG | ATC | CAG | ACG | 1590 |
| Ile | Gly | Val | Gln | Ala | Val | Ala | Pro | Glu | Ala | Gly | Glu | Leu | Ile | Gln | Thr | |
|     |     |     |     | 505 |     |     |     |     | 510 |     |     |     | 515 |     |     | |
| GCC | GCA | CTG | GCG | ATT | CGC | AAC | CGG | ATG | ACG | GTG | CAG | GAA | CTG | GCC | GAC | 1638 |
| Ala | Ala | Leu | Ala | Ile | Arg | Asn | Arg | Met | Thr | Val | Gln | Glu | Leu | Ala | Asp | |
|     |     | 520 |     |     |     |     | 525 |     |     |     |     | 530 |     |     |     | |
| CAG | TTG | TTC | CCC | TAC | CTG | ACG | ATG | GTC | GAA | GGG | TTG | AAG | CTC | GCG | GCG | 1686 |
| Gln | Leu | Phe | Pro | Tyr | Leu | Thr | Met | Val | Glu | Gly | Leu | Lys | Leu | Ala | Ala | |
|     | 535 |     |     |     |     | 540 |     |     |     |     | 545 |     |     |     |     | |
| CAG | ACC | TTC | AAC | AAG | GAT | GTG | AAG | CAG | CTT | TCC | TGC | TGC | GCC | GGG | TGA | 1734 |
| Gln | Thr | Phe | Asn | Lys | Asp | Val | Lys | Gln | Leu | Ser | Cys | Cys | Ala | Gly | *   | |
| 550 |     |     |     |     | 555 |     |     |     |     | 560 |     |     |     |     | 565 | |

GGCTGCAGGA ATTCGATA                                                                                              1752

( 2 ) INFORMATION FOR SEQ ID NO:20:

( i ) SEQUENCE CHARACTERISTICS:
        ( A ) LENGTH: 564 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

|     |     |     |     |     |     |     |     |     |     |     |     |     |     |     |
|-----|-----|-----|-----|-----|-----|-----|-----|-----|-----|-----|-----|-----|-----|-----|
| Met | Ser | Thr | Leu | Lys | Ile | Thr | Gly | Met | Thr | Cys | Asp | Ser | Cys | Ala | Val |
| 1   |     |     |     | 5   |     |     |     |     | 10  |     |     |     | 15  |     |     |
| His | Val | Lys | Asp | Ala | Leu | Glu | Lys | Val | Pro | Gly | Val | Gln | Ser | Ala | Asp |
|     |     |     | 20  |     |     |     | 25  |     |     |     | 30  |     |     |     |     |
| Val | Ser | Tyr | Ala | Lys | Gly | Ser | Ala | Lys | Leu | Ala | Ile | Glu | Val | Gly | Thr |
|     |     | 35  |     |     |     |     | 40  |     |     |     |     | 45  |     |     |     |
| Ser | Pro | Asp | Ala | Leu | Thr | Ala | Ala | Val | Ala | Gly | Leu | Gly | Tyr | Arg | Ala |
|     | 50  |     |     |     |     | 55  |     |     |     |     | 60  |     |     |     |     |
| Thr | Leu | Ala | Asp | Ala | Pro | Ser | Val | Ser | Thr | Pro | Gly | Gly | Leu | Leu | Asp |
| 65  |     |     |     |     | 70  |     |     |     |     | 75  |     |     |     |     | 80  |
| Lys | Met | Arg | Asp | Leu | Leu | Gly | Arg | Asn | Asp | Lys | Thr | Gly | Ser | Ser | Gly |
|     |     |     |     | 85  |     |     |     |     | 90  |     |     |     | 95  |     |     |
| Ala | Leu | His | Ile | Ala | Val | Ile | Gly | Ser | Gly | Gly | Ala | Ala | Met | Ala | Ala |
|     |     |     | 100 |     |     |     |     | 105 |     |     |     | 110 |     |     |     |
| Ala | Leu | Lys | Ala | Val | Glu | Gln | Gly | Ala | Pro | Val | Thr | Leu | Ile | Glu | Arg |
|     |     |     | 115 |     |     |     |     | 120 |     |     |     | 125 |     |     |     |
| Gly | Thr | Ile | Gly | Gly | Thr | Cys | Val | Asn | Val | Gly | Cys | Val | Pro | Ser | Lys |
|     |     | 130 |     |     |     |     | 135 |     |     |     |     | 140 |     |     |     |

| | | | | | | | | | | | | | | | |
|---|---|---|---|---|---|---|---|---|---|---|---|---|---|---|---|
| Ile | Met | Ile | Arg | Ala | Ala | His | Ile | Ala | His | Leu | Arg | Arg | Glu | Ser | Pro |
| 145 | | | | | 150 | | | | | 155 | | | | | 160 |
| Phe | Asp | Gly | Gly | Ile | Ala | Ala | Thr | Thr | Pro | Thr | Ile | Gln | Arg | Thr | Ala |
| | | | | 165 | | | | | 170 | | | | | 175 | |
| Leu | Leu | Ala | Gln | Gln | Gln | Ala | Arg | Val | Asp | Glu | Leu | Arg | His | Ala | Lys |
| | | | 180 | | | | | 185 | | | | | 190 | | |
| Tyr | Glu | Gly | Ile | Leu | Glu | Gly | Asn | Pro | Ala | Ile | Thr | Val | Leu | His | Gly |
| | | 195 | | | | | 200 | | | | | 205 | | | |
| Ser | Ala | Arg | Phe | Lys | Asp | Asn | Arg | Asn | Leu | Ile | Val | Gln | Leu | Asn | Asp |
| | 210 | | | | | 215 | | | | | 220 | | | | |
| Gly | Gly | Glu | Arg | Val | Val | Ala | Phe | Asp | Arg | Cys | Leu | Ile | Ala | Thr | Gly |
| 225 | | | | | 230 | | | | | 235 | | | | | 240 |
| Ala | Ser | Pro | Ala | Val | Pro | Pro | Ile | Pro | Gly | Leu | Lys | Asp | Thr | Pro | Tyr |
| | | | | 245 | | | | | 250 | | | | | 255 | |
| Trp | Thr | Ser | Thr | Glu | Ala | Leu | Val | Ser | Glu | Thr | Ile | Pro | Lys | Arg | Leu |
| | | | 260 | | | | | 265 | | | | | 270 | | |
| Ala | Val | Ile | Gly | Ser | Ser | Val | Val | Ala | Leu | Glu | Leu | Ala | Gln | Ala | Phe |
| | | 275 | | | | | 280 | | | | | 285 | | | |
| Ala | Arg | Leu | Gly | Ala | Lys | Val | Thr | Ile | Leu | Ala | Arg | Ser | Thr | Leu | Phe |
| | 290 | | | | | 295 | | | | | 300 | | | | |
| Phe | Arg | Glu | Asp | Pro | Ala | Ile | Gly | Glu | Ala | Val | Thr | Ala | Ala | Phe | Arg |
| 305 | | | | | 310 | | | | | 315 | | | | | 320 |
| Met | Glu | Gly | Ile | Glu | Val | Arg | Glu | His | Thr | Gln | Ala | Ser | Gln | Val | Ala |
| | | | | 325 | | | | | 330 | | | | | 335 | |
| Tyr | Ile | Asn | Gly | Glu | Gly | Asp | Gly | Glu | Phe | Val | Leu | Thr | Thr | Ala | His |
| | | | 340 | | | | | 345 | | | | | 350 | | |
| Gly | Glu | Leu | Arg | Ala | Asp | Lys | Leu | Leu | Val | Ala | Thr | Gly | Arg | Ala | Pro |
| | | 355 | | | | | 360 | | | | | 365 | | | |
| Asn | Thr | Arg | Lys | Leu | Ala | Leu | Asp | Ala | Thr | Gly | Val | Thr | Leu | Thr | Pro |
| | 370 | | | | | 375 | | | | | 380 | | | | |
| Gln | Gly | Ala | Ile | Val | Ile | Asp | Pro | Gly | Met | Arg | Thr | Ser | Val | Glu | His |
| 385 | | | | | 390 | | | | | 395 | | | | | 400 |
| Ile | Tyr | Ala | Ala | Gly | Asp | Cys | Thr | Asp | Gln | Pro | Gln | Phe | Val | Tyr | Val |
| | | | | 405 | | | | | 410 | | | | | 415 | |
| Ala | Ala | Ala | Ala | Gly | Thr | Arg | Ala | Ala | Ile | Asn | Met | Thr | Gly | Gly | Asp |
| | | | 420 | | | | | 425 | | | | | 430 | | |
| Ala | Ala | Leu | Asn | Leu | Thr | Ala | Met | Pro | Ala | Val | Val | Phe | Thr | Asp | Pro |
| | 435 | | | | | 440 | | | | | 445 | | | | |
| Gln | Val | Ala | Thr | Val | Gly | Tyr | Ser | Glu | Ala | Glu | Ala | His | His | Asp | Gly |
| 450 | | | | | 455 | | | | | 460 | | | | | |
| Ile | Lys | Thr | Asp | Ser | Arg | Thr | Leu | Thr | Leu | Asp | Asn | Val | Pro | Arg | Ala |
| 465 | | | | | 470 | | | | | 475 | | | | | 480 |
| Leu | Ala | Asn | Phe | Asp | Thr | Arg | Gly | Phe | Ile | Lys | Leu | Val | Val | Glu | Glu |
| | | | | 485 | | | | | 490 | | | | | 495 | |
| Gly | Ser | Gly | Arg | Leu | Ile | Gly | Val | Gln | Ala | Val | Ala | Pro | Glu | Ala | Gly |
| | | | 500 | | | | | 505 | | | | | 510 | | |
| Glu | Leu | Ile | Gln | Thr | Ala | Ala | Leu | Ala | Ile | Arg | Asn | Arg | Met | Thr | Val |
| | | 515 | | | | | 520 | | | | | 525 | | | |
| Gln | Glu | Leu | Ala | Asp | Gln | Leu | Phe | Pro | Tyr | Leu | Thr | Met | Val | Glu | Gly |
| | 530 | | | | | 535 | | | | | 540 | | | | |
| Leu | Lys | Leu | Ala | Ala | Gln | Thr | Phe | Asn | Lys | Asp | Val | Lys | Gln | Leu | Ser |
| 545 | | | | | 550 | | | | | 555 | | | | | 560 |
| Cys | Cys | Ala | Gly | | | | | | | | | | | | |
| | | | | 565 | | | | | | | | | | | |

( 2 ) INFORMATION FOR SEQ ID NO:21:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( i v ) ANTI-SENSE: NO ( x i ) SEQUENCE DESCRIPTION: SEQ ID NO:21:

```
AAGAAGAACC ACAATGTCTA CTCTGAAGAT CACTGGTATG ACTTGTGACT CTTGTGCAGT    60

GCATGTCAAG GA                                                        72
```

( 2 ) INFORMATION FOR SEQ ID NO:22:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( x i ) SEQUENCE DESCRIPTION: SEQ ID NO:22:

```
TCGAATTCCT GCAGCCTTAG CCAGCACAGC AGCTCAGCTG CTTCACATCC TT            52
```

( 2 ) INFORMATION FOR SEQ ID NO:23:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( x i ) SEQUENCE DESCRIPTION: SEQ ID NO:23:

```
CATACACAAA TTGTGGTTGA TCAGTGCAAT CACCAGCTGC ATAGATGTGT TCCACAGAGG    60

TACGCATACC TGGATCAATC ACAATAGCAC CTTGTGGAG                           99
```

( 2 ) INFORMATION FOR SEQ ID NO:24:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( i v ) ANTI-SENSE: NO ( x i ) SEQUENCE DESCRIPTION: SEQ ID NO:24:

```
ACCACAATTT GTGTATGTTG CTGCTGCTGC TGGTACCCGT GCTGCTATCA ACATGACTGG    60
```

TGGTGATGCT GCCCTCAACC TCACCGCGAT GCCGGCCGT                             99

( 2 ) INFORMATION FOR SEQ ID NO:25:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide"

( i i i ) HYPOTHETICAL: NO ( x i ) SEQUENCE DESCRIPTION: SEQ ID NO:25:

CAAATGGAGA TTCACGACGA AGATGAGCAA TGTGAGCAGC ACGAATCATG ATCTTGCTTG     60

GCACACAACC AACATTAACA CAGGTGCCGC CGATGGTGC                             99

( 2 ) INFORMATION FOR SEQ ID NO:26:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Olgionucleotide"

( i i i ) HYPOTHETICAL: NO ( i v ) ANTI-SENSE: NO ( x i ) SEQUENCE DESCRIPTION: SEQ ID NO:26:

TCGTGAATCT CCATTTGATG GTGGCATTGC TGCAACCACT CCAACCATTC AACGTACTGC     60

ACTCCTTGCA CAACAACAAG CACGTGTTGA TGAACTTCG                             99

( 2 ) INFORMATION FOR SEQ ID NO:27:

( i ) SEQUENCE CHARACTERISTICS:
        ( A ) LENGTH: 1752 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc ="Mutagenized merApe20"

( i i i ) HYPOTHETICAL: NO ( i v ) ANTI-SENSE: NO ( i x ) FEATURE:
        ( A ) NAME/KEY: CDS
        ( B ) LOCATION: 40..1734

( i x ) FEATURE:
        ( A ) NAME/KEY: mat_peptide
        ( B ) LOCATION: 40..1731

( x i ) SEQUENCE DESCRIPTION: SEQ ID NO:27:

```
CTAGAACTAG TGGATCCCTA GATCTAAGAA GGAACCACA ATG AGC ACT CTC AAA         54
                                            Met Ser Thr Leu Lys
                                            1               5

ATC ACC GGC ATG ACT TGC GAC TCG TGC GCA GTG CAT GTC AAG GAC GCC       102
Ile Thr Gly Met Thr Cys Asp Ser Cys Ala Val His Val Lys Asp Ala
            10              15                  20

CTG GAG AAA GTG CCC GGC GTG CAA TCA GCG GAT GTC TCC TAC GCC AAG       150
```

|  |  |  |  |  |  |  |  |  |  |  |  |  |  |  |  |
|---|---|---|---|---|---|---|---|---|---|---|---|---|---|---|---|
| Leu | Glu | Lys | Val | Pro | Gly | Val | Gln | Ser | Ala | Asp | Val | Ser | Tyr | Ala | Lys |
|  |  |  | 25 |  |  |  | 30 |  |  |  |  | 35 |  |  |  |

| GGC | AGC | GCC | AAG | CTC | GCC | ATT | GAG | GTC | GGC | ACG | TCA | CCC | GAC | GCG | CTG | 198 |
|---|---|---|---|---|---|---|---|---|---|---|---|---|---|---|---|---|
| Gly | Ser | Ala | Lys | Leu | Ala | Ile | Glu | Val | Gly | Thr | Ser | Pro | Asp | Ala | Leu | |
|  |  | 40 |  |  |  | 45 |  |  |  | 50 |  |  |  |  |  | |

| ACG | GCC | GCT | GTA | GCT | GGA | CTC | GGT | TAT | CGG | GCC | ACG | CTG | GCC | GAT | GCC | 246 |
|---|---|---|---|---|---|---|---|---|---|---|---|---|---|---|---|---|
| Thr | Ala | Ala | Val | Ala | Gly | Leu | Gly | Tyr | Arg | Ala | Thr | Leu | Ala | Asp | Ala | |
|  | 55 |  |  |  | 60 |  |  |  | 65 |  |  |  |  |  |  | |

| CCC | TCA | GTT | TCG | ACG | CCG | GGC | GGA | TTG | CTC | GAC | AAG | ATG | CGC | GAT | CTG | 294 |
|---|---|---|---|---|---|---|---|---|---|---|---|---|---|---|---|---|
| Pro | Ser | Val | Ser | Thr | Pro | Gly | Gly | Leu | Leu | Asp | Lys | Met | Arg | Asp | Leu | |
| 70 |  |  |  | 75 |  |  |  | 80 |  |  |  |  |  | 85 |  | |

| CTG | GGC | AGA | AAC | GAC | AAG | ACG | GGT | AGC | AGC | GGC | GCA | TTG | CAT | ATC | GCC | 342 |
|---|---|---|---|---|---|---|---|---|---|---|---|---|---|---|---|---|
| Leu | Gly | Arg | Asn | Asp | Lys | Thr | Gly | Ser | Ser | Gly | Ala | Leu | His | Ile | Ala | |
|  |  |  | 90 |  |  |  | 95 |  |  |  |  | 100 |  |  |  | |

| GTC | ATC | GGC | AGC | GGC | GGG | GCC | GCG | ATG | GCA | GCG | GCG | CTG | AAG | GCC | GTC | 390 |
|---|---|---|---|---|---|---|---|---|---|---|---|---|---|---|---|---|
| Val | Ile | Gly | Ser | Gly | Gly | Ala | Ala | Met | Ala | Ala | Ala | Leu | Lys | Ala | Val | |
|  |  | 105 |  |  |  | 110 |  |  |  | 115 |  |  |  |  |  | |

| GAG | CAA | GGC | GCA | CCT | GTC | ACG | CTG | ATC | GAG | CGC | GGC | ACC | ATC | GGC | GGC | 438 |
|---|---|---|---|---|---|---|---|---|---|---|---|---|---|---|---|---|
| Glu | Gln | Gly | Ala | Pro | Val | Thr | Leu | Ile | Glu | Arg | Gly | Thr | Ile | Gly | Gly | |
|  | 120 |  |  |  | 125 |  |  |  |  | 130 |  |  |  |  |  | |

| ACC | TGC | GTC | AAT | GTC | GGT | TGT | GTG | CCG | TCC | AAG | ATC | ATG | ATC | CGC | GCC | 486 |
|---|---|---|---|---|---|---|---|---|---|---|---|---|---|---|---|---|
| Thr | Cys | Val | Asn | Val | Gly | Cys | Val | Pro | Ser | Lys | Ile | Met | Ile | Arg | Ala | |
| 135 |  |  |  | 140 |  |  |  |  | 145 |  |  |  |  |  |  | |

| GCC | CAT | ATC | GCC | CAT | CTG | CGC | CGG | GAA | AGC | CCG | TTC | GAT | GGC | GGC | ATC | 534 |
|---|---|---|---|---|---|---|---|---|---|---|---|---|---|---|---|---|
| Ala | His | Ile | Ala | His | Leu | Arg | Arg | Glu | Ser | Pro | Phe | Asp | Gly | Gly | Ile | |
| 150 |  |  |  | 155 |  |  |  | 160 |  |  |  |  |  | 165 |  | |

| GCC | GCT | ACC | ACG | CCG | ACC | ATC | CAG | CGC | ACG | GCG | CTG | CTG | GCC | CAG | CAG | 582 |
|---|---|---|---|---|---|---|---|---|---|---|---|---|---|---|---|---|
| Ala | Ala | Thr | Thr | Pro | Thr | Ile | Gln | Arg | Thr | Ala | Leu | Leu | Ala | Gln | Gln | |
|  |  |  | 170 |  |  |  | 175 |  |  |  |  | 180 |  |  |  | |

| CAG | GCC | CGC | GTC | GAT | GAA | CTG | CGC | CAC | GCC | AAG | TAC | GAA | GGC | ATC | TTG | 630 |
|---|---|---|---|---|---|---|---|---|---|---|---|---|---|---|---|---|
| Gln | Ala | Arg | Val | Asp | Glu | Leu | Arg | His | Ala | Lys | Tyr | Glu | Gly | Ile | Leu | |
|  |  | 185 |  |  |  | 190 |  |  |  | 195 |  |  |  |  |  | |

| GAG | GGC | AAT | CCG | GCG | ATC | ACT | GTG | CTG | CAC | GGC | TCC | GCC | CGC | TTT | AAG | 678 |
|---|---|---|---|---|---|---|---|---|---|---|---|---|---|---|---|---|
| Glu | Gly | Asn | Pro | Ala | Ile | Thr | Val | Leu | His | Gly | Ser | Ala | Arg | Phe | Lys | |
|  |  | 200 |  |  |  | 205 |  |  |  | 210 |  |  |  |  |  | |

| GAC | AAT | CGC | AAC | CTG | ATC | GTG | CAA | CTC | AAC | GAC | GGC | GGC | GAG | CGC | GTG | 726 |
|---|---|---|---|---|---|---|---|---|---|---|---|---|---|---|---|---|
| Asp | Asn | Arg | Asn | Leu | Ile | Val | Gln | Leu | Asn | Asp | Gly | Gly | Glu | Arg | Val | |
|  | 215 |  |  |  | 220 |  |  |  | 225 |  |  |  |  |  |  | |

| GTG | GCA | TTC | GAC | CGC | TGT | CTC | ATT | GCC | ACT | GGT | GCA | AGC | CCA | GCT | GTT | 774 |
|---|---|---|---|---|---|---|---|---|---|---|---|---|---|---|---|---|
| Val | Ala | Phe | Asp | Arg | Cys | Leu | Ile | Ala | Thr | Gly | Ala | Ser | Pro | Ala | Val | |
| 230 |  |  |  | 235 |  |  |  | 240 |  |  |  |  |  | 245 |  | |

| CCA | CCA | ATT | CCT | GGT | CTC | AAG | GAC | ACT | CCT | TAC | TGG | ACT | TCC | ACT | GAA | 822 |
|---|---|---|---|---|---|---|---|---|---|---|---|---|---|---|---|---|
| Pro | Pro | Ile | Pro | Gly | Leu | Lys | Asp | Thr | Pro | Tyr | Trp | Thr | Ser | Thr | Glu | |
|  |  |  | 250 |  |  |  | 255 |  |  |  |  | 260 |  |  |  | |

| GCA | CTA | GTG | TCT | GAG | ACC | ATT | CCA | AAG | CGT | CTT | GCA | GTC | ATT | GGC | TCC | 870 |
|---|---|---|---|---|---|---|---|---|---|---|---|---|---|---|---|---|
| Ala | Leu | Val | Ser | Glu | Thr | Ile | Pro | Lys | Arg | Leu | Ala | Val | Ile | Gly | Ser | |
|  |  | 265 |  |  |  | 270 |  |  |  | 275 |  |  |  |  |  | |

| TCT | GTG | GTG | GCT | CTT | GAA | CTT | GCC | CAG | GCC | TTT | GCA | CGT | CTT | GGT | GCT | 918 |
|---|---|---|---|---|---|---|---|---|---|---|---|---|---|---|---|---|
| Ser | Val | Val | Ala | Leu | Glu | Leu | Ala | Gln | Ala | Phe | Ala | Arg | Leu | Gly | Ala | |
|  | 280 |  |  |  | 285 |  |  |  | 290 |  |  |  |  |  |  | |

| AAA | GTG | ACC | ATT | CTT | GCA | CGC | TCC | ACT | CTC | TTC | TTT | CGT | GAA | GAC | CCA | 966 |
|---|---|---|---|---|---|---|---|---|---|---|---|---|---|---|---|---|
| Lys | Val | Thr | Ile | Leu | Ala | Arg | Ser | Thr | Leu | Phe | Phe | Arg | Glu | Asp | Pro | |
|  | 295 |  |  |  | 300 |  |  |  | 305 |  |  |  |  |  |  | |

| GCT | ATA | GGT | GAA | GCT | GTT | ACT | GCT | GCA | TTT | CGC | ATG | GAA | GGC | ATT | GAA | 1014 |
|---|---|---|---|---|---|---|---|---|---|---|---|---|---|---|---|---|
| Ala | Ile | Gly | Glu | Ala | Val | Thr | Ala | Ala | Phe | Arg | Met | Glu | Gly | Ile | Glu | |
| 310 |  |  |  | 315 |  |  |  |  | 320 |  |  |  | 325 |  |  | |

| GTG | CGT | GAG | CAT | ACT | CAA | GCA | AGC | CAA | GTT | GCC | TAT | ATC | AAT | GGT | GAA | 1062 |
|---|---|---|---|---|---|---|---|---|---|---|---|---|---|---|---|---|
| Val | Arg | Glu | His | Thr | Gln | Ala | Ser | Gln | Val | Ala | Tyr | Ile | Asn | Gly | Glu | |
|  |  |  | 330 |  |  |  | 335 |  |  |  |  | 340 |  |  |  | |

| GGG | GAC | GGC | GAA | TTC | GTG | CTC | ACC | ACG | GCG | CAC | GGC | GAA | CTG | CGC | GCC | 1110 |

| | | | | | | | | | | | | | | | | |
|---|---|---|---|---|---|---|---|---|---|---|---|---|---|---|---|---|
| Gly | Asp | Gly | Glu | Phe | Val | Leu | Thr | Thr | Ala | His | Gly | Glu | Leu | Arg | Ala | |
| | | | 345 | | | | | 350 | | | | | 355 | | | |

| GAC | AAG | CTG | CTG | GTC | GCC | ACC | GGC | CGC | GCG | CCC | AAC | ACA | CGC | AAG | CTG | 1158 |
|---|---|---|---|---|---|---|---|---|---|---|---|---|---|---|---|---|
| Asp | Lys | Leu | Leu | Val | Ala | Thr | Gly | Arg | Ala | Pro | Asn | Thr | Arg | Lys | Leu | |
| | | 360 | | | | | 365 | | | | | 370 | | | | |

| GCA | CTG | GAT | GCG | ACG | GGC | GTC | ACG | CTC | ACC | CCC | CAA | GGC | GCT | ATC | GTC | 1206 |
|---|---|---|---|---|---|---|---|---|---|---|---|---|---|---|---|---|
| Ala | Leu | Asp | Ala | Thr | Gly | Val | Thr | Leu | Thr | Pro | Gln | Gly | Ala | Ile | Val | |
| 375 | | | | | 380 | | | | | 385 | | | | | | |

| ATC | GAC | CCC | GGC | ATG | CGT | ACA | AGC | GTG | GAA | CAC | ATC | TAC | GCC | GCA | GGC | 1254 |
|---|---|---|---|---|---|---|---|---|---|---|---|---|---|---|---|---|
| Ile | Asp | Pro | Gly | Met | Arg | Thr | Ser | Val | Glu | His | Ile | Tyr | Ala | Ala | Gly | |
| 390 | | | | | 395 | | | | 400 | | | | | | 405 | |

| GAC | TGC | ACC | GAC | CAG | CCG | CAG | TTC | GTC | TAT | GTG | GCG | GCA | GCG | GCC | GGC | 1302 |
|---|---|---|---|---|---|---|---|---|---|---|---|---|---|---|---|---|
| Asp | Cys | Thr | Asp | Gln | Pro | Gln | Phe | Val | Tyr | Val | Ala | Ala | Ala | Ala | Gly | |
| | | | | 410 | | | | | 415 | | | | | 420 | | |

| ACT | CGC | GCC | GCG | ATC | AAC | ATG | ACC | GGC | GGT | GAC | GCC | GCC | CTG | AAC | CTG | 1350 |
|---|---|---|---|---|---|---|---|---|---|---|---|---|---|---|---|---|
| Thr | Arg | Ala | Ala | Ile | Asn | Met | Thr | Gly | Gly | Asp | Ala | Ala | Leu | Asn | Leu | |
| | | | 425 | | | | | 430 | | | | | 435 | | | |

| ACC | GCG | ATG | CCG | GCC | GTG | GTG | TTC | ACC | GAC | CCG | CAA | GTG | GCG | ACC | GTA | 1398 |
|---|---|---|---|---|---|---|---|---|---|---|---|---|---|---|---|---|
| Thr | Ala | Met | Pro | Ala | Val | Val | Phe | Thr | Asp | Pro | Gln | Val | Ala | Thr | Val | |
| | | 440 | | | | | 445 | | | | | 450 | | | | |

| GGC | TAC | AGC | GAG | GCG | GAA | GCG | CAC | CAT | GAC | GGC | ATC | AAA | ACT | GAT | AGT | 1446 |
|---|---|---|---|---|---|---|---|---|---|---|---|---|---|---|---|---|
| Gly | Tyr | Ser | Glu | Ala | Glu | Ala | His | His | Asp | Gly | Ile | Lys | Thr | Asp | Ser | |
| | 455 | | | | | 460 | | | | | 465 | | | | | |

| CGC | ACG | CTA | ACG | CTG | GAC | AAC | GTG | CCG | CGC | GCG | CTC | GCC | AAC | TTC | GAC | 1494 |
|---|---|---|---|---|---|---|---|---|---|---|---|---|---|---|---|---|
| Arg | Thr | Leu | Thr | Leu | Asp | Asn | Val | Pro | Arg | Ala | Leu | Ala | Asn | Phe | Asp | |
| 470 | | | | | 475 | | | | | 480 | | | | | 485 | |

| ACG | CGC | GGC | TTC | ATC | AAA | CTG | GTG | GTT | GAA | GAA | GGG | AGC | GGA | CGA | CTG | 1542 |
|---|---|---|---|---|---|---|---|---|---|---|---|---|---|---|---|---|
| Thr | Arg | Gly | Phe | Ile | Lys | Leu | Val | Val | Glu | Glu | Gly | Ser | Gly | Arg | Leu | |
| | | | | 490 | | | | | 495 | | | | | 500 | | |

| ATC | GGC | GTC | CAG | GCA | GTG | GCC | CCG | GAA | GCG | GGC | GAA | CTG | ATC | CAG | ACG | 1590 |
|---|---|---|---|---|---|---|---|---|---|---|---|---|---|---|---|---|
| Ile | Gly | Val | Gln | Ala | Val | Ala | Pro | Glu | Ala | Gly | Glu | Leu | Ile | Gln | Thr | |
| | | | 505 | | | | | 510 | | | | | 515 | | | |

| GCC | GCA | CTG | GCG | ATT | CGC | AAC | CGG | ATG | ACG | GTG | CAG | GAA | CTG | GCC | GAC | 1638 |
|---|---|---|---|---|---|---|---|---|---|---|---|---|---|---|---|---|
| Ala | Ala | Leu | Ala | Ile | Arg | Asn | Arg | Met | Thr | Val | Gln | Glu | Leu | Ala | Asp | |
| | | 520 | | | | | 525 | | | | | 530 | | | | |

| CAG | TTG | TTC | CCC | TAC | CTG | ACG | ATG | GTC | GAA | GGG | TTG | AAG | CTC | GCG | GCG | 1686 |
|---|---|---|---|---|---|---|---|---|---|---|---|---|---|---|---|---|
| Gln | Leu | Phe | Pro | Tyr | Leu | Thr | Met | Val | Glu | Gly | Leu | Lys | Leu | Ala | Ala | |
| | 535 | | | | | 540 | | | | | 545 | | | | | |

| CAG | ACC | TTC | AAC | AAG | GAT | GTG | AAG | CAG | CTT | TCC | TGC | TGC | GCC | GGG | TGA | 1734 |
|---|---|---|---|---|---|---|---|---|---|---|---|---|---|---|---|---|
| Gln | Thr | Phe | Asn | Lys | Asp | Val | Lys | Gln | Leu | Ser | Cys | Cys | Ala | Gly | * | |
| 550 | | | | | 555 | | | | | 560 | | | | | 565 | |

| GGCTGCAGGA ATTCGATA | 1752 |
|---|---|

( 2 ) INFORMATION FOR SEQ ID NO:28:

( i ) SEQUENCE CHARACTERISTICS:
        ( A ) LENGTH: 564 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| Met | Ser | Thr | Leu | Lys | Ile | Thr | Gly | Met | Thr | Cys | Asp | Ser | Cys | Ala | Val |
|---|---|---|---|---|---|---|---|---|---|---|---|---|---|---|---|
| 1 | | | | 5 | | | | | 10 | | | | | 15 | |

| His | Val | Lys | Asp | Ala | Leu | Glu | Lys | Val | Pro | Gly | Val | Gln | Ser | Ala | Asp |
|---|---|---|---|---|---|---|---|---|---|---|---|---|---|---|---|
| | | | 20 | | | | | 25 | | | | | 30 | | |

| Val | Ser | Tyr | Ala | Lys | Gly | Ser | Ala | Lys | Leu | Ala | Ile | Glu | Val | Gly | Thr |
|---|---|---|---|---|---|---|---|---|---|---|---|---|---|---|---|
| | | 35 | | | | | 40 | | | | | 45 | | | |

| Ser | Pro | Asp | Ala | Leu | Thr | Ala | Ala | Val | Ala | Gly | Leu | Gly | Tyr | Arg | Ala |
|---|---|---|---|---|---|---|---|---|---|---|---|---|---|---|---|
| | 50 | | | | | 55 | | | | | 60 | | | | |

```
Thr Leu Ala Asp Ala Pro Ser Val Ser Thr Pro Gly Gly Leu Leu Asp
 65              70              75              80

Lys Met Arg Asp Leu Leu Gly Arg Asn Asp Lys Thr Gly Ser Ser Gly
             85              90              95

Ala Leu His Ile Ala Val Ile Gly Ser Gly Ala Ala Met Ala Ala
            100             105             110

Ala Leu Lys Ala Val Glu Gln Gly Ala Pro Val Thr Leu Ile Glu Arg
        115             120             125

Gly Thr Ile Gly Gly Thr Cys Val Asn Val Gly Cys Val Pro Ser Lys
    130             135             140

Ile Met Ile Arg Ala Ala His Ile Ala His Leu Arg Arg Glu Ser Pro
145             150             155             160

Phe Asp Gly Gly Ile Ala Ala Thr Thr Pro Thr Ile Gln Arg Thr Ala
                165             170             175

Leu Leu Ala Gln Gln Gln Ala Arg Val Asp Glu Leu Arg His Ala Lys
            180             185             190

Tyr Glu Gly Ile Leu Glu Gly Asn Pro Ala Ile Thr Val Leu His Gly
        195             200             205

Ser Ala Arg Phe Lys Asp Asn Arg Asn Leu Ile Val Gln Leu Asn Asp
    210             215             220

Gly Gly Glu Arg Val Val Ala Phe Asp Arg Cys Leu Ile Ala Thr Gly
225             230             235             240

Ala Ser Pro Ala Val Pro Pro Ile Pro Gly Leu Lys Asp Thr Pro Tyr
                245             250             255

Trp Thr Ser Thr Glu Ala Leu Val Ser Glu Thr Ile Pro Lys Arg Leu
            260             265             270

Ala Val Ile Gly Ser Ser Val Val Ala Leu Glu Leu Ala Gln Ala Phe
        275             280             285

Ala Arg Leu Gly Ala Lys Val Thr Ile Leu Ala Arg Ser Thr Leu Phe
    290             295             300

Phe Arg Glu Asp Pro Ala Ile Gly Glu Ala Val Thr Ala Ala Phe Arg
305             310             315             320

Met Glu Gly Ile Glu Val Arg Glu His Thr Gln Ala Ser Gln Val Ala
                325             330             335

Tyr Ile Asn Gly Glu Gly Asp Gly Glu Phe Val Leu Thr Thr Ala His
            340             345             350

Gly Glu Leu Arg Ala Asp Lys Leu Leu Val Ala Thr Gly Arg Ala Pro
        355             360             365

Asn Thr Arg Lys Leu Ala Leu Asp Ala Thr Gly Val Thr Leu Thr Pro
    370             375             380

Gln Gly Ala Ile Val Ile Asp Pro Gly Met Arg Thr Ser Val Glu His
385             390             395             400

Ile Tyr Ala Ala Gly Asp Cys Thr Asp Gln Pro Gln Phe Val Tyr Val
                405             410             415

Ala Ala Ala Ala Gly Thr Arg Ala Ala Ile Asn Met Thr Gly Gly Asp
            420             425             430

Ala Ala Leu Asn Leu Thr Ala Met Pro Ala Val Val Phe Thr Asp Pro
        435             440             445

Gln Val Ala Thr Val Gly Tyr Ser Glu Ala Glu Ala His His Asp Gly
    450             455             460

Ile Lys Thr Asp Ser Arg Thr Leu Thr Leu Asp Asn Val Pro Arg Ala
465             470             475             480

Leu Ala Asn Phe Asp Thr Arg Gly Phe Ile Lys Leu Val Val Glu Glu
```

|         |         |         | 485     |         |         |         | 490     |         |         |         |         | 495     |         |         |
|---------|---------|---------|---------|---------|---------|---------|---------|---------|---------|---------|---------|---------|---------|---------|
| Gly     | Ser     | Gly     | Arg     | Leu     | Ile     | Gly     | Val     | Gln     | Ala     | Val     | Ala     | Pro     | Glu     | Ala     | Gly     |
|         |         | 500     |         |         |         |         | 505     |         |         |         |         | 510     |         |         |         |
| Glu     | Leu     | Ile     | Gln     | Thr     | Ala     | Ala     | Leu     | Ala     | Ile     | Arg     | Asn     | Arg     | Met     | Thr     | Val     |
|         |         | 515     |         |         |         |         | 520     |         |         |         |         | 525     |         |         |         |
| Gln     | Glu     | Leu     | Ala     | Asp     | Gln     | Leu     | Phe     | Pro     | Tyr     | Leu     | Thr     | Met     | Val     | Glu     | Gly     |
|         | 530     |         |         |         |         | 535     |         |         |         |         | 540     |         |         |         |         |
| Leu     | Lys     | Leu     | Ala     | Ala     | Gln     | Thr     | Phe     | Asn     | Lys     | Asp     | Val     | Lys     | Gln     | Leu     | Ser     |
| 545     |         |         |         |         | 550     |         |         |         |         | 555     |         |         |         |         | 560     |
| Cys     | Cys     | Ala     | Gly     |
|         |         |         | 565     |

(2) INFORMATION FOR SEQ ID NO:29:

(i) SEQUENCE CHARACTERISTICS:
        (A) LENGTH: 1746 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc ="Mutagenized merApe29"

(iii) HYPOTHETICAL: NO (ix) FEATURE:
        (A) NAME/KEY: CDS
        (B) LOCATION: 40..1728

(ix) FEATURE:
        (A) NAME/KEY: mat_peptide
        (B) LOCATION: 40..1725

(xi) SEQUENCE DESCRIPTION: SEQ ID NO:29:

| CTAGAACTAG | TGGATCCCTA | GATCTAAGAA | GGAACCACA | ATG | AGC | ACT | CTC | AAA |     |     |     |     |     |     | 54  |
|------------|------------|------------|-----------|-----|-----|-----|-----|-----|-----|-----|-----|-----|-----|-----|-----|
|            |            |            |           | Met | Ser | Thr | Leu | Lys |     |     |     |     |     |     |     |
|            |            |            |           |  1  |     |     |     |  5  |     |     |     |     |     |     |     |

| ATC | ACC | GGC | ATG | ACT | TGC | GAC | TCG | TGC | GCA | GTG | CAT | GTC | AAG | GAC | GCC | 102 |
|-----|-----|-----|-----|-----|-----|-----|-----|-----|-----|-----|-----|-----|-----|-----|-----|-----|
| Ile | Thr | Gly | Met | Thr | Cys | Asp | Ser | Cys | Ala | Val | His | Val | Lys | Asp | Ala |     |
|     |     |     | 10  |     |     |     |     | 15  |     |     |     |     | 20  |     |     |     |

| CTG | GAG | AAA | GTG | CCC | GGC | GTG | CAA | TCA | GCG | GAT | GTC | TCC | TAC | GCC | AAG | 150 |
|-----|-----|-----|-----|-----|-----|-----|-----|-----|-----|-----|-----|-----|-----|-----|-----|-----|
| Leu | Glu | Lys | Val | Pro | Gly | Val | Gln | Ser | Ala | Asp | Val | Ser | Tyr | Ala | Lys |     |
|     |     | 25  |     |     |     |     | 30  |     |     |     |     | 35  |     |     |     |     |

| GGC | AGC | GCC | AAG | CTC | GCC | ATT | GAG | GTC | GGC | ACG | TCA | CCC | GAC | GCG | CTG | 198 |
|-----|-----|-----|-----|-----|-----|-----|-----|-----|-----|-----|-----|-----|-----|-----|-----|-----|
| Gly | Ser | Ala | Lys | Leu | Ala | Ile | Glu | Val | Gly | Thr | Ser | Pro | Asp | Ala | Leu |     |
|     |     |     | 40  |     |     |     |     | 45  |     |     |     |     | 50  |     |     |     |

| ACG | GCC | GCT | GTA | GCT | GGA | CTC | GGT | TAT | CGG | GCC | ACG | CTG | GCC | GAT | GCC | 246 |
|-----|-----|-----|-----|-----|-----|-----|-----|-----|-----|-----|-----|-----|-----|-----|-----|-----|
| Thr | Ala | Ala | Val | Ala | Gly | Leu | Gly | Tyr | Arg | Ala | Thr | Leu | Ala | Asp | Ala |     |
|     |     | 55  |     |     |     |     | 60  |     |     |     |     | 65  |     |     |     |     |

| CCC | TCA | GTT | TCG | ACG | CCG | GGC | GGA | TTG | CTC | GAC | AAG | ATG | CGC | GAT | CTG | 294 |
|-----|-----|-----|-----|-----|-----|-----|-----|-----|-----|-----|-----|-----|-----|-----|-----|-----|
| Pro | Ser | Val | Ser | Thr | Pro | Gly | Gly | Leu | Leu | Asp | Lys | Met | Arg | Asp | Leu |     |
| 70  |     |     |     |     | 75  |     |     |     |     | 80  |     |     |     |     | 85  |     |

| CTG | GGC | AGA | AAC | GAC | AAG | ACG | GGT | AGC | AGC | GGC | GCA | TTG | CAT | ATC | GCC | 342 |
|-----|-----|-----|-----|-----|-----|-----|-----|-----|-----|-----|-----|-----|-----|-----|-----|-----|
| Leu | Gly | Arg | Asn | Asp | Lys | Thr | Gly | Ser | Ser | Gly | Ala | Leu | His | Ile | Ala |     |
|     |     |     |     | 90  |     |     |     |     | 95  |     |     |     |     | 100 |     |     |

| GTC | ATC | GGC | AGC | GGC | GGG | GCC | GCG | ATG | GCA | GCG | GCG | CTG | AAG | GCC | GTC | 390 |
|-----|-----|-----|-----|-----|-----|-----|-----|-----|-----|-----|-----|-----|-----|-----|-----|-----|
| Val | Ile | Gly | Ser | Gly | Gly | Ala | Ala | Met | Ala | Ala | Ala | Leu | Lys | Ala | Val |     |
|     |     |     |     | 105 |     |     |     |     | 110 |     |     |     |     | 115 |     |     |

| GAG | CAA | GGC | GCA | CCT | GTC | ACG | CTG | ATC | GAG | CGC | GGC | ACC | ATC | GGC | GGC | 438 |
|-----|-----|-----|-----|-----|-----|-----|-----|-----|-----|-----|-----|-----|-----|-----|-----|-----|
| Glu | Gln | Gly | Ala | Pro | Val | Thr | Leu | Ile | Glu | Arg | Gly | Thr | Ile | Gly | Gly |     |
|     |     | 120 |     |     |     |     | 125 |     |     |     |     | 130 |     |     |     |     |

| ACC | TGC | GTC | AAT | GTC | GGT | TGT | GTG | CCG | TCC | AAG | ATC | ATG | ATC | CGC | GCC | 486 |
|-----|-----|-----|-----|-----|-----|-----|-----|-----|-----|-----|-----|-----|-----|-----|-----|-----|
| Thr | Cys | Val | Asn | Val | Gly | Cys | Val | Pro | Ser | Lys | Ile | Met | Ile | Arg | Ala |     |
|     | 135 |     |     |     |     | 140 |     |     |     |     | 145 |     |     |     |     |     |

| | | | | | | | | | | | | | | | | |
|---|---|---|---|---|---|---|---|---|---|---|---|---|---|---|---|---|
| GCC | CAT | ATC | GCC | CAT | CTG | CGC | CGG | GAA | AGC | CCG | TTC | GAT | GGC | GGC | ATC | 534 |
| Ala | His | Ile | Ala | His | Leu | Arg | Arg | Glu | Ser | Pro | Phe | Asp | Gly | Gly | Ile | |
| 150 | | | | 155 | | | | | 160 | | | | | | 165 | |
| GCC | GCT | ACC | ACG | CCG | ACC | ATC | CAG | CGC | ACG | GCG | CTG | CTG | GCC | CAG | CAG | 582 |
| Ala | Ala | Thr | Thr | Pro | Thr | Ile | Gln | Arg | Thr | Ala | Leu | Leu | Ala | Gln | Gln | |
| | | | | 170 | | | | | 175 | | | | | 180 | | |
| CAG | GCC | CGC | GTC | GAT | GAA | CTG | CGT | CAT | GCA | AAG | TAT | GAA | GGT | ATT | CTA | 630 |
| Gln | Ala | Arg | Val | Asp | Glu | Leu | Arg | His | Ala | Lys | Tyr | Glu | Gly | Ile | Leu | |
| | | | 185 | | | | | 190 | | | | | 195 | | | |
| GAA | GGT | AAC | CCA | GCC | ATC | ACT | GTG | CTT | CAT | GGC | TCT | GCA | CGT | TTC | AAG | 678 |
| Glu | Gly | Asn | Pro | Ala | Ile | Thr | Val | Leu | His | Gly | Ser | Ala | Arg | Phe | Lys | |
| | | 200 | | | | | 205 | | | | | 210 | | | | |
| GAC | AAC | CGT | AAC | CTC | ATT | GTT | CAA | CTC | AAC | GAC | GGC | GGC | GAG | CGC | GTG | 726 |
| Asp | Asn | Arg | Asn | Leu | Ile | Val | Gln | Leu | Asn | Asp | Gly | Gly | Glu | Arg | Val | |
| | | 215 | | | | 220 | | | | | 225 | | | | | |
| GTG | GCA | TTC | GAC | CGC | TGT | CTC | ATT | GCC | ACT | GGT | GCA | AGC | CCA | GCT | GTT | 774 |
| Val | Ala | Phe | Asp | Arg | Cys | Leu | Ile | Ala | Thr | Gly | Ala | Ser | Pro | Ala | Val | |
| 230 | | | | | 235 | | | | 240 | | | | | | 245 | |
| CCA | CCA | ATT | CCT | GGT | CTC | AAG | GAC | ACT | CCT | TAC | TGG | ACT | TCC | ACT | GAA | 822 |
| Pro | Pro | Ile | Pro | Gly | Leu | Lys | Asp | Thr | Pro | Tyr | Trp | Thr | Ser | Thr | Glu | |
| | | | | 250 | | | | | 255 | | | | | 260 | | |
| GTG | TCT | GAG | ACC | ATT | CCA | AAG | CGT | CTT | GCA | GTC | ATT | GGC | TCC | TCT | GTG | 870 |
| Val | Ser | Glu | Thr | Ile | Pro | Lys | Arg | Leu | Ala | Val | Ile | Gly | Ser | Ser | Val | |
| | | | 265 | | | | | 270 | | | | | 275 | | | |
| GTG | GCT | CTT | GAA | CTT | GCC | CAG | GCC | TTT | GCA | CGT | CTT | GGT | GCT | AAA | GTG | 918 |
| Val | Ala | Leu | Glu | Leu | Ala | Gln | Ala | Phe | Ala | Arg | Leu | Gly | Ala | Lys | Val | |
| | | 280 | | | | | 285 | | | | | 290 | | | | |
| ACC | ATT | CTT | GCA | CGC | TCC | ACT | CTC | TTC | TTT | CGT | GAA | GAC | CCA | GCT | ATA | 966 |
| Thr | Ile | Leu | Ala | Arg | Ser | Thr | Leu | Phe | Phe | Arg | Glu | Asp | Pro | Ala | Ile | |
| | 295 | | | | | 300 | | | | | 305 | | | | | |
| GGT | GAA | GCT | GTT | ACT | GCT | GCA | TTT | CGC | ATG | GAA | GGC | ATT | GAA | GTG | CGT | 1014 |
| Gly | Glu | Ala | Val | Thr | Ala | Ala | Phe | Arg | Met | Glu | Gly | Ile | Glu | Val | Arg | |
| 310 | | | | | 315 | | | | 320 | | | | | | 325 | |
| GAG | CAT | ACT | CAA | GCA | AGC | CAA | GTT | GCC | TAT | ATC | AAT | GGT | GAA | GGG | GAC | 1062 |
| Glu | His | Thr | Gln | Ala | Ser | Gln | Val | Ala | Tyr | Ile | Asn | Gly | Glu | Gly | Asp | |
| | | | | 330 | | | | 335 | | | | | 340 | | | |
| GGC | GAA | TTC | GTG | CTC | ACC | ACG | GCG | CAC | GGC | GAA | CTG | CGC | GCC | GAC | AAG | 1110 |
| Gly | Glu | Phe | Val | Leu | Thr | Thr | Ala | His | Gly | Glu | Leu | Arg | Ala | Asp | Lys | |
| | | | 345 | | | | | 350 | | | | | 355 | | | |
| CTG | CTG | GTC | GCC | ACC | GGC | CGC | GCG | CCC | AAC | ACA | CGC | AAG | CTG | GCA | CTG | 1158 |
| Leu | Leu | Val | Ala | Thr | Gly | Arg | Ala | Pro | Asn | Thr | Arg | Lys | Leu | Ala | Leu | |
| | | | 360 | | | | 365 | | | | | 370 | | | | |
| GAT | GCG | ACG | GGC | GTC | ACG | CTC | ACC | CCC | CAA | GGC | GCT | ATC | GTC | ATC | GAC | 1206 |
| Asp | Ala | Thr | Gly | Val | Thr | Leu | Thr | Pro | Gln | Gly | Ala | Ile | Val | Ile | Asp | |
| | 375 | | | | | 380 | | | | | 385 | | | | | |
| CCC | GGC | ATG | CGT | ACA | AGC | GTG | GAA | CAC | ATC | TAC | GCC | GCA | GGC | GAC | TGC | 1254 |
| Pro | Gly | Met | Arg | Thr | Ser | Val | Glu | His | Ile | Tyr | Ala | Ala | Gly | Asp | Cys | |
| 390 | | | | | 395 | | | | 400 | | | | | | 405 | |
| ACC | GAC | CAG | CCG | CAG | TTC | GTC | TAT | GTG | GCG | GCA | GCG | GCC | GGC | ACT | CGC | 1302 |
| Thr | Asp | Gln | Pro | Gln | Phe | Val | Tyr | Val | Ala | Ala | Ala | Ala | Gly | Thr | Arg | |
| | | | | 410 | | | | 415 | | | | | 420 | | | |
| GCC | GCG | ATC | AAC | ATG | ACC | GGC | GGT | GAC | GCC | GCC | CTG | AAC | CTG | ACC | GCG | 1350 |
| Ala | Ala | Ile | Asn | Met | Thr | Gly | Gly | Asp | Ala | Ala | Leu | Asn | Leu | Thr | Ala | |
| | | | 425 | | | | 430 | | | | | 435 | | | | |
| ATG | CCG | GCC | GTG | GTG | TTC | ACC | GAC | CCG | CAA | GTG | GCG | ACC | GTA | GGC | TAC | 1398 |
| Met | Pro | Ala | Val | Val | Phe | Thr | Asp | Pro | Gln | Val | Ala | Thr | Val | Gly | Tyr | |
| | | 440 | | | | | 445 | | | | | 450 | | | | |
| AGC | GAG | GCG | GAA | GCG | CAC | CAT | GAC | GGC | ATC | AAA | ACT | GAT | AGT | CGC | ACG | 1446 |
| Ser | Glu | Ala | Glu | Ala | His | His | Asp | Gly | Ile | Lys | Thr | Asp | Ser | Arg | Thr | |
| | 455 | | | | 460 | | | | 465 | | | | | | | |

| | | | | | | | | | | | | | | | |
|---|---|---|---|---|---|---|---|---|---|---|---|---|---|---|---|
| CTA | ACG | CTG | GAC | AAC | GTG | CCG | CGC | GCG | CTC | GCC | AAC | TTC | GAC | ACG | CGC | 1494 |
| Leu | Thr | Leu | Asp | Asn | Val | Pro | Arg | Ala | Leu | Ala | Asn | Phe | Asp | Thr | Arg | |
| 470 | | | | 475 | | | | | 480 | | | | | 485 | | |
| GGC | TTC | ATC | AAA | CTG | GTG | GTT | GAA | GAA | GGG | AGC | GGA | CGA | CTG | ATC | GGC | 1542 |
| Gly | Phe | Ile | Lys | Leu | Val | Val | Glu | Glu | Gly | Ser | Gly | Arg | Leu | Ile | Gly | |
| | | | | 490 | | | | | 495 | | | | | 500 | | |
| GTC | CAG | GCA | GTG | GCC | CCG | GAA | GCG | GGC | GAA | CTG | ATC | CAG | ACG | GCC | GCA | 1590 |
| Val | Gln | Ala | Val | Ala | Pro | Glu | Ala | Gly | Glu | Leu | Ile | Gln | Thr | Ala | Ala | |
| | | | 505 | | | | | 510 | | | | | 515 | | | |
| CTG | GCG | ATT | CGC | AAC | CGG | ATG | ACG | GTG | CAG | GAA | CTG | GCC | GAC | CAG | TTG | 1638 |
| Leu | Ala | Ile | Arg | Asn | Arg | Met | Thr | Val | Gln | Glu | Leu | Ala | Asp | Gln | Leu | |
| | | | 520 | | | | | 525 | | | | | 530 | | | |
| TTC | CCC | TAC | CTG | ACG | ATG | GTC | GAA | GGG | TTG | AAG | CTC | GCG | GCG | CAG | ACC | 1686 |
| Phe | Pro | Tyr | Leu | Thr | Met | Val | Glu | Gly | Leu | Lys | Leu | Ala | Ala | Gln | Thr | |
| | 535 | | | | | 540 | | | | | 545 | | | | | |
| TTC | AAC | AAG | GAT | GTG | AAG | CAG | CTT | TCC | TGC | TGC | GCC | GGG | TGA | | | 1728 |
| Phe | Asn | Lys | Asp | Val | Lys | Gln | Leu | Ser | Cys | Cys | Ala | Gly | * | | | |
| 550 | | | | | 555 | | | | | 560 | | | | | | |

GGCTGCAGGA ATTCGATA 1746

( 2 ) INFORMATION FOR SEQ ID NO:30:

( i ) SEQUENCE CHARACTERISTICS:
        ( A ) LENGTH: 562 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| | | | | | | | | | | | | | | |
|---|---|---|---|---|---|---|---|---|---|---|---|---|---|---|
| Met | Ser | Thr | Leu | Lys | Ile | Thr | Gly | Met | Thr | Cys | Asp | Ser | Cys | Ala | Val |
| 1 | | | | 5 | | | | | 10 | | | | | 15 | |
| His | Val | Lys | Asp | Ala | Leu | Glu | Lys | Val | Pro | Gly | Val | Gln | Ser | Ala | Asp |
| | | | 20 | | | | | 25 | | | | | 30 | | |
| Val | Ser | Tyr | Ala | Lys | Gly | Ser | Ala | Lys | Leu | Ala | Ile | Glu | Val | Gly | Thr |
| | | 35 | | | | | 40 | | | | | 45 | | | |
| Ser | Pro | Asp | Ala | Leu | Thr | Ala | Ala | Val | Ala | Gly | Leu | Gly | Tyr | Arg | Ala |
| | 50 | | | | | 55 | | | | | 60 | | | | |
| Thr | Leu | Ala | Asp | Ala | Pro | Ser | Val | Ser | Thr | Pro | Gly | Gly | Leu | Leu | Asp |
| 65 | | | | | 70 | | | | | 75 | | | | | 80 |
| Lys | Met | Arg | Asp | Leu | Leu | Gly | Arg | Asn | Asp | Lys | Thr | Gly | Ser | Ser | Gly |
| | | | | 85 | | | | | 90 | | | | | 95 | |
| Ala | Leu | His | Ile | Ala | Val | Ile | Gly | Ser | Gly | Gly | Ala | Ala | Met | Ala | Ala |
| | | | 100 | | | | | 105 | | | | | 110 | | |
| Ala | Leu | Lys | Ala | Val | Glu | Gln | Gly | Ala | Pro | Val | Thr | Leu | Ile | Glu | Arg |
| | | 115 | | | | | 120 | | | | | 125 | | | |
| Gly | Thr | Ile | Gly | Gly | Thr | Cys | Val | Asn | Val | Gly | Cys | Val | Pro | Ser | Lys |
| | 130 | | | | | 135 | | | | | 140 | | | | |
| Ile | Met | Ile | Arg | Ala | Ala | His | Ile | Ala | His | Leu | Arg | Arg | Glu | Ser | Pro |
| 145 | | | | | 150 | | | | | 155 | | | | | 160 |
| Phe | Asp | Gly | Gly | Ile | Ala | Ala | Thr | Thr | Pro | Thr | Ile | Gln | Arg | Thr | Ala |
| | | | | 165 | | | | | 170 | | | | | 175 | |
| Leu | Leu | Ala | Gln | Gln | Gln | Ala | Arg | Val | Asp | Glu | Leu | Arg | His | Ala | Lys |
| | | | 180 | | | | | 185 | | | | | 190 | | |
| Tyr | Glu | Gly | Ile | Leu | Glu | Gly | Asn | Pro | Ala | Ile | Thr | Val | Leu | His | Gly |
| | | 195 | | | | | 200 | | | | | 205 | | | |
| Ser | Ala | Arg | Phe | Lys | Asp | Asn | Arg | Asn | Leu | Ile | Val | Gln | Leu | Asn | Asp |
| | 210 | | | | | 215 | | | | | 220 | | | | |

```
Gly Gly Glu Arg Val Val Ala Phe Asp Arg Cys Leu Ile Ala Thr Gly
225             230             235             240

Ala Ser Pro Ala Val Pro Pro Ile Pro Gly Leu Lys Asp Thr Pro Tyr
                245             250             255

Trp Thr Ser Thr Glu Val Ser Glu Thr Ile Pro Lys Arg Leu Ala Val
            260             265             270

Ile Gly Ser Ser Val Val Ala Leu Glu Leu Ala Gln Ala Phe Ala Arg
            275             280             285

Leu Gly Ala Lys Val Thr Ile Leu Ala Arg Ser Thr Leu Phe Phe Arg
    290             295             300

Glu Asp Pro Ala Ile Gly Glu Ala Val Thr Ala Ala Phe Arg Met Glu
305             310             315             320

Gly Ile Glu Val Arg Glu His Thr Gln Ala Ser Gln Val Ala Tyr Ile
                325             330             335

Asn Gly Glu Gly Asp Gly Glu Phe Val Leu Thr Thr Ala His Gly Glu
            340             345             350

Leu Arg Ala Asp Lys Leu Leu Val Ala Thr Gly Arg Ala Pro Asn Thr
        355             360             365

Arg Lys Leu Ala Leu Asp Ala Thr Gly Val Thr Leu Thr Pro Gln Gly
    370             375             380

Ala Ile Val Ile Asp Pro Gly Met Arg Thr Ser Val Glu His Ile Tyr
385             390             395             400

Ala Ala Gly Asp Cys Thr Asp Gln Pro Gln Phe Val Tyr Val Ala Ala
            405             410             415

Ala Ala Gly Thr Arg Ala Ala Ile Asn Met Thr Gly Gly Asp Ala Ala
            420             425             430

Leu Asn Leu Thr Ala Met Pro Ala Val Val Phe Thr Asp Pro Gln Val
        435             440             445

Ala Thr Val Gly Tyr Ser Glu Ala Glu Ala His His Asp Gly Ile Lys
    450             455             460

Thr Asp Ser Arg Thr Leu Thr Leu Asp Asn Val Pro Arg Ala Leu Ala
465             470             475             480

Asn Phe Asp Thr Arg Gly Phe Ile Lys Leu Val Val Glu Glu Gly Ser
            485             490             495

Gly Arg Leu Ile Gly Val Gln Ala Val Ala Pro Glu Ala Gly Glu Leu
        500             505             510

Ile Gln Thr Ala Ala Leu Ala Ile Arg Asn Arg Met Thr Val Gln Glu
    515             520             525

Leu Ala Asp Gln Leu Phe Pro Tyr Leu Thr Met Val Glu Gly Leu Lys
    530             535             540

Leu Ala Ala Gln Thr Phe Asn Lys Asp Val Lys Gln Leu Ser Cys Cys
545             550             555             560

Ala Gly *
```

METAL RESISTANCE SEQUENCES AND TRANSGENIC PLANTS

This invention was made in part with funding from the National Science Foundation and the Environmental Protection Agency. Accordingly, the United States government may have certain rights in this invention.

THE FIELD OF THE INVENTION

The field of this invention is the area of plant molecular biology, and it relates in particular, to metal and organometal resistance genes functional in plants, transgenic plants containing same, and methods for remediation of environmental metal contamination using the transgenic plants of the present invention.

THE BACKGROUND OF THE INVENTION

Contamination of the environment with metal ions and/or alkyl and thiol derivatives of metals has increased over the last several decades, with toxic levels of the contaminants being reached in air, water and/or soil in certain locations. Contamination may stem from human and industrial sources, or in certain locales, the soil is contaminated naturally with such toxic metals as arsenic, cadmium, copper, cobalt, lead, mercury, selenium and/or zinc.

Mercury is often found in soil and marine sediments as thiol salts, as chelates with acidic humic substances such as methylmercury and to a lesser extent other organomercurials, and as free $Hg^{++}$. Mercury cycles through the aqueous phase and into the atmosphere as volatile elemental Hg and methylmercury, and is then oxidized and washed by rain into the marine environment [Barkay et al. (1992) *Biodegradation* 3:147–159]. Some bacteria in soil and sediments can detoxify ionic mercury by reducing it to its metallic form in an NADPH-coupled reaction, which is efficiently catalyzed by mercuric ion reductase. Mercury is often found bound in the form of organomercurial compounds in contaminated animals and microbes [Barkay et al. (1992) supra; Robinson and Tuovinen (1984) *Microbiological Reviews* 48:95–124]. In fish, where mercury toxicity is well studied, most of the tissue-associated mercury is found as methylmercury, and its production may be the product of a nonenzymatic reaction of $Hg^{++}$ with methyl-B12 [Pan Hou and Imura (1987) *Arch. Microbiol.* 131:176–177]. Dimethylmercury is volatile, and both mono- and dimethylmercury are extremely toxic [D'Itri and D'Itri (1987) *Environ. Management* 2:3–16]. Although the effects and levels of methylmercury in plants and the contribution of plants to the production of organomercurial compounds in the environment are not known, it is likely that macrophytes are a major source of organomercury compounds in the environment based on the biochemical activity of the dominant macrophytes in many fresh water, estuarine and marine environments.

Certain plants express phytochelatins, a group of γ-glutamylcysteine peptides which are the products of a complex synthetic pathway [Scheller et al. (1987) *Plant Physiol.* 85:1031–1035]. Phytochelatins mediate some metal resistance in plants which produce them [Grill et al. (1987) *Proc. Natl. Acad. Sci. USA* 84:439–443]. Lefebvre et al. (1987) *Biotechnology* 5:1053–1056 reported the construction of transgenic plant tissue expressing a mammalian metallothionein gene; that tissue exhibited some resistance to cadmium.

The bacterial gene merA used by the present inventors is derived from the transposon Tn21, which was originally isolated from the Incompatibility Group IncFII resistance plasmid NR1 [see e.g., Gilbert and Summers (1988) *Plasmid* 20:127–136]. The product of the bacterial merA gene is mercuric ion reductase (MerA). MerA can detoxify ionic mercury by reducing it to its less toxic (insoluble and volatile) elemental form ($Hg^0$). MerA belongs to a family of reductase enzymes which are related in their primary structures. As a family, these reductases act on a wide variety of organic and thiol substrates in addition to the thiol salts of divalent Hg.

Some of the bacterial mer operons also encode an organomercurial lyase (MerB, methylmercury lyase, Tn21 merB gene product) which catalyzes the protonolytic cleavage of carbon-mercury bonds, $RCH_2Hg^+ \rightarrow Hg^{++} + RCH_3$, and together with MerA produces what is termed broad spectrum mercury resistance (resistance to both thiolmercurial and alkylmercurial compounds and resistance to mercuric ion). The MerB protein cleaves a variety of carbon-mercury compounds, from methylmercury to long chain hydrocarbon and aromatic derivatives [Begley et al. (1986) *Biochemistry* 25:7186–7192; Begley et al. (1986) ibid. 7192–7200]. This process removes methylmercury and then metallic mercury from the environment.

Additional genes often part of bacterial mer operons include merT (mercury transport through the cell membrane) and merP (mercury sequestration in the periplasmic space of gram-negative bacteria). Mercury resistance genes are reviewed in Summers, A. O. (1986) *Ann. Rev. Microbiology* 40:607–634.

Regions which are naturally contaminated with heavy metals are often characterized by scrubby heavy-metal tolerant vegetation [Brooks and Malaisse (1985) *The Heavy Metal-tolerant Flora of South Central Africa*, A. A. Balkema Press, Boston, Mass.; Wild, H. (1978) "The Vegetation of Heavy Metal and Other Toxic Soils," in *Biogeography and Ecology of Southern Africa*, Wergren, M. J. H., ed, Junk, The Hague, Netherlands]. Certain of these naturally occurring metal-resistant plants hyperaccumulate large amounts of heavy metals in the form of malate or citrate chelates. These plants have been found in a variety of habitats, but often they exhibit bizarre metal ion requirements, grow poorly in less exotic habitats, and are of little direct economic value as crop or forest species.

There is a long felt need in the art for the in situ remediation of toxic metal ions and/or metal complexes (e.g., alkyl and thiol metal adducts). The present invention enables phytoremediation and/or revegetation of contaminated environments via the plant-expressible metal resistance coding sequences disclosed herein.

SUMMARY OF THE INVENTION

The present invention provides nucleic acid sequences which mediate resistance to heavy metal in transgenic plants or plant cells which express these coding sequences encoding metal ion reductases. Preferably the coding sequence is that of plant-expressible merA (which encodes mercuric ion reductase). As specifically exemplified, the plant-expressible metal resistance coding sequences are include merApe9, merApe20, merApe29, merApe38, and merApe47 (SEQ ID NOS: 15, 27, 29, 13 and 19, respectively), as disclosed herein (See FIGS. 1–2). Also, within the scope of the present invention are metal resistance genes with sequences completely modified for plant gene expressions.

Another aspect of the present invention are plant-expressible metal resistance coding sequences operably linked to transcriptional and translational control sequences which are functional in plants. Preferably the coding sequence is that of plant-expressible merA (which encodes mercury reductase). As specifically exemplified, the plant-expressible metal resistance coding sequences are include merApe9, merApe20, merApe29, merApe38, and merApe47 (SEQ ID NOS: 15, 27, 29, 13 and 19, respectively), as disclosed herein (See FIGS. 1–2).

A further aspect of the present invention are transgenic plant cells, plant tissue and plants which have been genetically engineered to contain and express a plant-expressible metal resistance coding sequence operably linked to transcriptional and translational control sequences which are functional in plants. Preferably the coding sequence is that of plant-expressible merA (which encodes mercury ion reductase). As specifically exemplified, the plant-expressible metal resistance coding sequences are include merApe9, merApe20, merApe29, merApe38, and merApe47 (SEQ ID NOS: 15, 27, 29, 13 and 19, respectively), as disclosed herein (See FIGS. 1–2).

Also provided by the present invention are methods for effecting metal resistance in plants by stably transforming a plant to contain and express a nucleotide sequence of a plant-expressible metal resistance coding sequences operably linked to transcriptional and translational control sequences which are functional in plants. Preferably the coding sequence is that of plant-expressible merA (which encodes mercury reductase). As specifically exemplified, the plant-expressible metal resistance coding sequences are include merApe9, merApe20, merApe29, merApe38, and merApe47 (SEQ ID NOS: 15, 27, 29, 13 and 19, respectively), as disclosed herein (See FIGS. 1–2).

A further aspect of the invention are plant-expressible nucleotide-sequences which mediate resistance to organomercurial compounds in conjunction with the plant-expressible metal resistance coding sequences of the present invention. As specifically exemplified herein, the coding sequence mediating organomercurial resistance is that of merB, which encodes methylmercury lyase, which has been adapted for plant gene expression as disclosed herein (See FIG. 4).

A further object of the invention are transgenic plants genetically engineered to contain and express plant-expressible metal resistance coding sequences, and plants also genetically engineered to further contain and express organomercurial resistance coding sequences according to the teachings of this disclosure.

BRIEF DESCRIPTION OF THE DRAWINGS

FIGS. 1A–1D illustrate the construction of merApe9 by overlap extension polymerase chain reaction (OE PCR). The primers used to prepare the "a" and "b" fragments are shown below the merA map. The "a" and "b" fragments were joined in a PCR reaction using the "a" and "b" fragments as templates and the 5'S and 3'N primers. Primer sequences are given in Table 2 hereinbelow. pNS2 contains modified 5' and 3' flanking sequences with bacterial ribosome binding sites (SD) and consensus plant translation signals (PT) as well as restriction sites to be used in subsequent cloning experiments.

FIG. 4 is a schematic representation of the strategy for producing a plant-expressible merB coding sequence. Overlap extension PCR using pCT12 as template and MerB5'S (SEQ ID NO: 17) and MerB3'A (SEQ ID NO: 18) as primers is used to adapt the merB for plant (and/or animal) gene expression, as described in Example 8.

DETAILED DESCRIPTION OF THE INVENTION

Figures 1A, 1B:
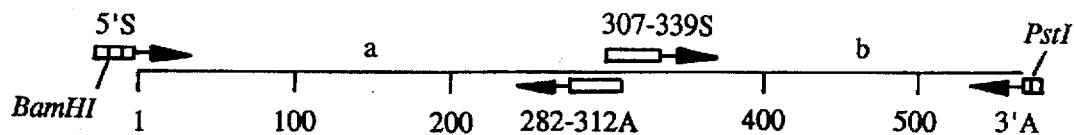

Because metal contamination of the environment is a problem, it is urgent that modern technology provide solutions which are economical in terms of money and natural resources and which are also safe for the environment.

As used herein, the term "metal resistance" means that a non-naturally occurring organism is not inhibited by the presence of at least one of divalent cations of mercury, cadmium, cobalt, trivalent cations of gold, and monovalent silver ion, at concentrations (levels) at which a naturally occurring (wild-type) counterpart of the non-naturally occurring organism is inhibited or exhibits symptoms of toxicity. It is not intended that the term metal resistance refer to resistance to unlimited concentration of metal ions, but rather the term is relative in that it relies on comparison to the properties of a parental strain.

A "metal resistance coding sequence" is one which encodes a protein capable of mediating resistance to at least one metal ion, including, but not limited to, divalent cations of mercury, nickel, cobalt, trivalent cations of gold, and by monovalent cations of silver. Also within the scope of this definition are mutant sequences which determine proteins capable of mediating resistance to divalent cations of lead, cadmium and copper.

An "organomercurial resistance coding sequence" is one whose protein product mediates resistance to such organic mercury compounds as alkylmercurials and certain aromatic mercurials, for example, mono- or dimethylmercury, typically in conjunction with a metal resistance gene such as merA. As specifically exemplified herein, the organomercurial resistance gene is the methylmercury lyase gene (merB) and its gene product confers resistance to organomercurial compounds such as methymercury, p-chloromercuribenzoate (PCMB) and p-hydroxymercuribenzoate in conjunction with the merA gene product (mercury ion reductase).

With respect to a coding sequence, the term "plant-expressible" means that the coding sequence (nucleotide sequence) can be efficiently expressed by plant cells, tissue and whole plants. The art understands that a plant-expressible coding sequence has a GC composition consistent with good gene expression in plant cells, a sufficiently low CpG content so that expression of that coding sequence is not restricted by plant cells, and codon usage which is consistent with that of plant genes. Where it is desired that the properties of the plant-expressible metal resistance gene are identical to those of the naturally occurring metal resistance gene, the plant-expressible homolog will have a synonymous coding sequence or a substantially synonymous coding sequence. A substantially synonymous coding sequence is one in which there are one or more codons which encode a similar amino acid to a comparison sequence, or if the amino acid substituted is not similar in properties to the one it replaces, that change has no significant effect on enzymatic activity for at least one substrate of that enzyme. As discussed hereinbelow, it is well understood that in most cases, there is some flexibility in amino acid sequence such that function is not significantly changed. The skilled artisan understands such conservative changes in amino acid sequence, and the resultant similar protein can be readily tested without the expense of undue experimentation using procedures such as those disclosed herein. Where it is desired that the plant-expressible gene have different properties, there can be variation in the amino acid sequence as compared to the wild-type gene, and the properties of metal resistance can be readily determined as described herein, again without the expense of undue experimentation.

"Plant-expressible transcriptional and translational regulatory sequences" are those which can function in plants, plant tissue and plant cells to effect the transcriptional and translational expression of the nucleotide sequences with which they are associated. Included are 5' sequences to a target sequence to be expressed which qualitatively control gene expression (turn on or off gene expression in response to environmental signals such as light, or in a tissue-specific manner) and quantitative regulatory sequences which advantageously increase the level of downstream gene expression. An example of a sequence motif which serves as a translational control sequence is that of the ribosome binding site sequence. Polyadenylation signals are examples of transcription regulatory sequences positioned downstream of a target sequence, and there are several well known in the art of plant molecular biology; these include the 3' flanking sequences of the nos gene.

A "non-naturally occurring recombinant nucleic acid molecule", e.g., a recombinant DNA molecule, is one which does not occur in nature; i.e., it is produced either by natural processes using methods known to the art but is directed by man to produce a desired result, or it has been artificially produced from parts derived from heterologous sources, which parts may be naturally occurring or chemically synthesized molecules or portions thereof, and wherein those parts have been joined by ligation or other means known to the art.

A "transgenic plant" is one which has been genetically modified to contain and express heterologous DNA sequences, either as regulatory RNA molecules or as proteins. As specifically exemplified herein, a transgenic plant is genetically modified to contain and express at least one heterologous DNA sequence operably linked to and under the regulatory control of transcriptional control sequences which function in plant cells or tissue or in whole plants. As used herein, a transgenic plant also refers to progeny of the initial transgenic plant where those progeny contain and are capable of expressing the heterologous coding sequence under the regulatory control of the plant-expressible transcription control sequences described herein. Seeds containing transgenic embryos are encompassed within this definition.

When plant expression of a heterologous gene or coding sequence of interest is desired, that coding sequence is operably linked in the sense orientation to a suitable promoter and advantageously under the regulatory control of DNA sequences which quantitatively regulate transcription of a downstream sequence in plant cells or tissue or in planta, in the same orientation as the promoter, so that a sense (i.e., functional for translational expression) mRNA is produced. A transcription termination signal, for example, as polyadenylation signal, functional in a plant cell is advantageously placed downstream of the mercury resistance coding sequence, and a selectable marker which can be expressed in a plant, can be covalently linked to the inducible expression unit so that after this DNA molecule is introduced into a plant cell or tissue, its presence can be selected and plant cells or tissue not so transformed will be killed or prevented from growing. In the present invention, the mercury resistance coding sequence can serve as a selectable marker for transformation of plant cells or tissue. Where constitutive gene expression is desired, suitable plant-expressible promoters include the 35S or 19S promoters of Cauliflower Mosaic Virus, the Nos, ocs or mas promoters of *Agrobacterium tumefaciens* Ti plasmids, and others known to the art. Where tissue specific expression of the plant-expressible metal resistance coding sequence is desired, the skilled artisan will choose from a number of well-known sequences to mediate that form of gene expression. Environmentally regulated promoters are also well known in the art, and the skilled artisan can choose from well known transcription regulatory sequences to achieve the desired result.

The metal resistance protein (MerA protein, mercuric ion reductase) is exemplified by that from Tn21, a bacterial mercury resistance transposon originally isolated from the IncFII plasmid NR1. The amino acid sequence is given in SEQ ID NO:2. In addition to reducing mercuric ions, the Tn21 MerA reduces trivalent gold and monovalent silver cations [Summers and Sugarman (1974) *Journal of Bacteriology* 119:242–249]. Monovalent silver and certain divalent metal cations have been shown to be competitive inhibitors of mercuric ion reduction in vitro [Rinderle et al. (1983) *Biochemistry* 22:869–876]. Data obtained by the present inventors indicate that MerA mediates resistance to trivalent gold, divalent cobalt, divalent copper and divalent nickel cations as well as divalent ionic mercury.

Because mercury resistant plants are desirable for their potential roles in revegetation of contaminated soils (e.g., subsequent to mining operations) and/or bioremediation of soils and/or aquatic environments contaminated with ionic mercury, the naturally occurring merA coding sequence derived from the bacterial transposon Tn21 was incorporated in transgenic plants under the regulatory control of the Cauliflower Mosaic Virus 35S plant-expressible promoter. The MerA protein did not appear to be produced and the transgenic plants did not exhibit greater resistance to mercuric ions than did control plants lacking this gene [Thompson, D. M. (1990) *Transcriptional and Post-transcriptional Regulation of the Genes Encoding the Small Subunit of Ribulose-1,5-Bisphosphate Carboxylase,* Ph.D. Thesis, University of Georgia, Athens, Ga.].

An additional benefit of the metal resistant plants is their ability to harvest metals; precious and semi-precious metals can be reduced and thereby trapped in plant tissues. These metals include can include gold, silver, platinum, rhenium, copper, palladium, nickel, zinc and cadmium, where the corresponding metal ions are reduced by the metal resistance gene product in those plants.

Examination of the merA coding sequence [Barrineau et al. (1984) *Journal of Molecular and Applied Genetics* 2:601–619] revealed that the 1695 nucleotide open reading frame contains 67% G+C and 218 CpG dinucleotides. Those CpG dinucleotides and codons skewed for G or C in the third nucleotide are uncommon in plants [McClelland and Ivarie (1982) *Nucleic Acids Research* 10:1865–7877; Murray et al. (1989) *Nucleic Acids Research* 17:477–494] as well as in *Escherichia coli* [Phillips and Kushner (1987) *Journal of Biological Chemistry* 262:455–459]. Raina et al. (1993) *Proc. Natl. Acad. Sci. USA* 90:6355–6359 have reported that plant promoters are often hypermethylated and turned off when adjacent to CpG-rich sequences.

The present inventors have constructed DNA sequences which encode a metal resistance protein which is expressed in plant cells. As specifically exemplified, this modified sequences are presented in FIGS. 1 and 2. The deduced amino acid sequence for the naturally occurring heavy metal resistance protein MerA (mercury ion reductase) is given in SEQ ID NO:2. The open reading frame extends from an ATG beginning at nucleotide 14 through the stop codon ending at nucleotide 1708 in SEQ ID NO:1. Sequences for MerApe 9, MerApe 20, MerApe29, MerApe 38 and MerApe 48 are provided herein.

The function of the MerA proteins synthesized by *E. coli* cells expressing the merApe9 and merApe38 sequences are reflected in the mercury resistance phenotypes of strains carrying pNS2 and pNS5 (See Table 1 and Example 6). *E. coli* cells which express all of the mer operon except a functional reductase (merA) exhibit mercury hypersensitivity. A culture of isogenic *E. coli* hypersensitive to mercury which contains pBluescript without insert served as a negative control. Control cells were hypersensitive to mercuric ion and totally inactive in the reduction of mercuric ions.

Figure 3:
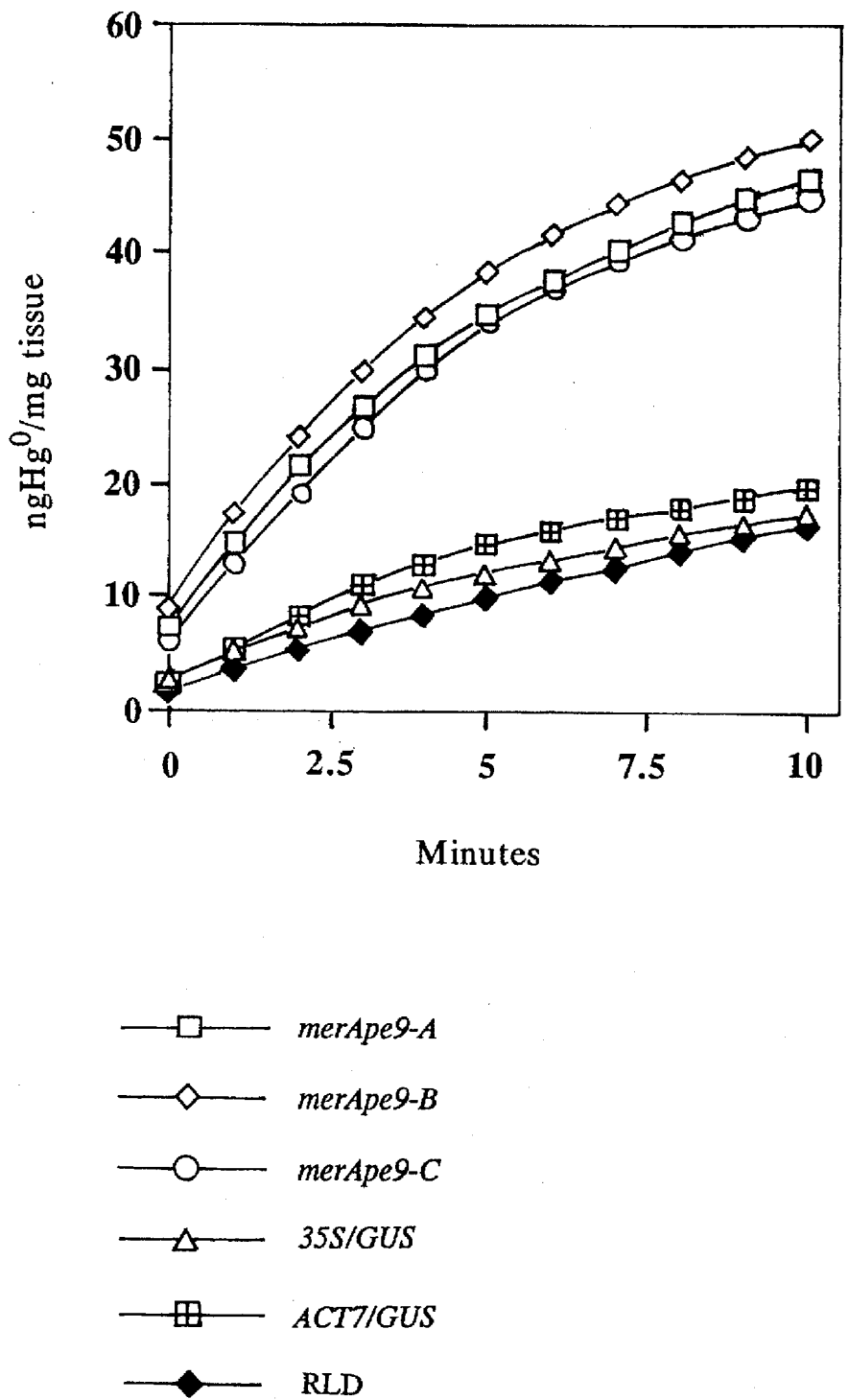
FIG. 3 illustrates the evolution of Hg$^0$ with time in control *Arabidopsis thaliana* var. RLD plants, and representative transgenic plants expressing merApe9. (Mercury evolution by transgenic plants expressing merApe 9: -□- merApe 9-A, -◇- merApe 9-B, -○- merApe 9-C; -♦- *A. thaliana* RLD control, -△- transgenic plant expressing GUS gene under CaMV 35S promoter control, -⊞- transgenic plant expressing GUS under control of Actin 7 promoter).

Transgenic plant tissue containing and expressing the merApe9 (SEQ ID NO:15) coding sequence mediated the evolution of elemental mercury at levels significantly greater than for control plant tissue (See FIG. 3 and Example 7). 10 mg of transgenic MerA⁺ seedling tissue evolved about 500 ng Hg⁰ during the 10 minute assay period. Control untransformed plants and transgenic plants expressing the unrelated β-glucuronidase (GUS) gene under the control of the CaMV 35S promoter or the Actin7 promoter did not evolve significatn amounts of elemental mercury during the incubation period (<1 ng Hg⁰/50 mg plant tissue/10 min).

It is understood that nucleic acid sequences other than that of SEQ ID NO:1, from nucleotide 14 through nucleotide 1708, or MerApe 20, MerApe 29, MerApe 38 or MerApe 47 (SEQ ID NOS: 27, 29, 13 and 19, respectively) will function as coding sequences synonymous with the exemplified merApe9 coding sequence. Nucleic acid sequences are synonymous if the amino acid sequences encoded by those nucleic acid sequences are the same. The degeneracy of the genetic code is well known to the art; i.e., for many amino acids, there is more than one nucleotide triplet which serves as the codon for the amino acid; for expression in plant cells or tissue it is desired that codon usage reflect that of plant genes and that CpG dinucleotides be kept low in frequency in the coding sequence. It is also well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Vol. 5, Suppl. 3, pp. 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

A plant-expressible transcription and translation regulatory sequence can be operably linked to any promoter sequence functional in plants as understood by the skilled artisan; where a regulatory element is to be coupled to a promoter, generally a truncated (or minimal) promoter is used, for example, the truncated 35S promoter of Cauliflower Mosaic Virus, CaMV). Truncated versions of other constitutive promoters can also be used to provide CAAT and TATA-homologous regions; such promoter sequences can be derived from those of *A. tumefaciens* T-DNA genes such as Nos, ocs and mas and plant virus genes such as the CaMV 19S gene. It will be understood that the goals of a skilled artisan will determine the choice of particular transcriptional (and translational) regulatory sequences. Translational control sequences specifically exemplified herein are the nucleotides between 8 and 13 upstream of the ATG translation start codon for bacterial signals and from nucleotides 1 to 7 upstream of the ATG translation start codon for plants (See FIG. 18).

A minimal promoter contains the DNA sequence signals necessary for RNA polymerase binding and initiation of transcription. For RNA polymerase II promoters the promoter is identified by a TATA-homologous sequences motif about 20 to 50 bp upstream of the transcription start site and a CAAT-homologous sequence motif about 50 to 120 bp upstream of the transcription start site. By convention, the skilled artisan often numbers the nucleotides upstream of the transcription start with increasingly large numbers extending upstream of (in the 5' direction) from the start site. Generally, transcription directed by a minimal promoter is low and does not respond either positively or negatively to environmental or developmental signals in plant tissue. An exemplary minimal promoter suitable for use in plants is the truncated CaMV 35S promoter, which contains the regions from –90 to +8 of the 35S gene. Where a minimal promoter is used, it is desired that for high levels of gene expression, transcription regulatory sequences which upregulate the levels of gene expression be operably linked thereto. Such quantitative regulatory sequences are exemplified by transcription enhancing regulatory sequences such as enhancers.

Operably linking transcription and translation regulatory sequences upstream of a promoter functional in a plant cell allows the expression of the mercury resistance coding sequence (or the methylmercury lyase coding sequence) operably fused just downstream of the promoter, and the skilled artisan understands spacing requirements and ribosome binding site requirements for translational expression of the coding sequence. The mercury resistance coding sequence preferably encodes the merA protein of Tn21, as exemplified by the amino acid sequence in SEQ ID NO:2.

In plants, the constitutive plant-expressible transcription and translation regulatory element effects the expression of a downstream plant-expressible metal resistance coding sequence. Data is presented for metal resistance in *Arabidopsis thaliana* genetically engineered to contain and express a plant-expressible merA coding sequence, in particular, merApe9. Other plant-expressible metal resistance coding sequences provided by the present invention include merApe20, merApe29, merApe38 and merApe47 (SEQ ID NOS: 27, 29, 13 and 19), respectively). When resistance to organomercurials is desired plants are genetically engineered to contain and express a plant-expressible merB coding sequence (merB) in addition to a plant-expressible merA sequence. Similar results are obtained in other plants, including monocots, dicots and gymnosperms, after stable transformation, as for the *Arabidopsis thaliana* ecperiments described herein.

Coding sequences suitable for expression in a plant are operably linked downstream of a constitutive or a regulated promoter construct. Transgenic plants can be constructed using the chimeric gene consisting essentially of the promoter, any additional transcription enhancing sequences, and the desired mercury resistance coding sequence including the necessary sequence signals for its translation.

Alternative plant-expressible mercury resistance and organomercury resistance coding sequences which can be expressed include those from merA genes from Tn501 and plasmid R100 [Brown et al. (1983) *Biochemistry* 22:4089–4095; Misra et al. (1985) *Gene* 34:253–262].

Additionally, or alternatively, induction of the regulated construct can be induced, for example, by treating the transgenic plant or tissue with an inducer suitable for regulating expression of the plant-expressible mercury resistance coding sequences of the present invention. The expression of the mercury resistance coding sequence can also be regulated by tissue specific transcription regulatory sequences.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment and subsequent selection and regeneration (see Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205; Gasser and Fraley (1989) *Sci.* 244:1293; Leemans (1993) *Bio/Technology.* 11:522; Beck et al. (1993) *Bio/Technology.* 11:1524; Koziel et al. (1993) *Bio/Technology.* 11:194; Vasil et al. (1993) *Bio/Technology.* 11:1533). Techniques are well known to the art for the introduction of DNA into monocots as well as dicots, as are the techniques for culturing such plant tissues and regenerating those tissues. Monocots which have been successfully transformed and regenerated include wheat, corn, rye, rice and asparagus. For efficient regeneration of transgenic plants, it is desired that the plant tissue used in the transformation possess a high capacity to produce shoots. For example, Aspen stem sections have good regeneration capacity. [Devillard, C. III et al. (1992) *C.R. Acad. Sci. Set. VIE* 314: 291–298K; Nilsson et al. (1992) *Transgenic Research* 1: 209–220; Tsai et al. (1994) *Plant Cell Rep.* 14: 94–97] Poplars have been successfully transformed [Wilde et al. (1992) *Plant Physiol.* 98:114–120].

Techniques for introducing and selecting for the presence of heterologous DNA in plant tissue are well known. For example, *A. tumefaciens*-mediated DNA transfer into plant tissue, followed by selection and growth in vitro and subsequent regeneration of the transformed plant tissue to a plant is well known for a variety of plants.

Other techniques for genetically engineering plant tissue to contain an expression cassette comprising a promoter and associated transcription regulatory sequences fused to the metal resistance coding sequence and optionally containing a transcription termination region are to be integrated into the plant cell genome by electroporation, co-cultivation, microinjection, particle bombardment and other techniques known to the art. The metal resistance plant expression cassette further contains a marker allowing selection of the expression cassette in the plant cell, e.g., genes carrying resistance to an antibiotic such as kanamycin, hygromycin, gentamicin, or bleomycin. The marker allows for selection of successfully transformed plant cells growing in the medium containing certain antibiotics because they will carry the expression cassette with resistance gene to the antibiotic.

The following examples use many techniques well known and accessible to those skilled in the arts of molecular biology, in the manipulation of recombinant DNA in plant tissue and in the culture and regeneration of transgenic plants. Enzymes are obtained from commercial sources and are used according to the vendors' recommendations or other variations known to the art. Reagents, buffers and culture conditions are also known to the art. References providing standard molecular biological procedures include Sambrook et al. (1989) *Molecular Cloning*, second edition, Cold Spring Harbor Laboratory, Plainview, N.Y., R. Wu (ed.) (1993) *Methods in Enzymology* 218, Wu et al. (eds.) *Methods in Enzymology* 100, 101, Glover (ed.) (1985) *DNA Cloning*, Vols. I and II, IRL Press, Oxford, UK; and Hames and Higgins (eds.) (1985) *Nucleic Acid Hybridization*, IRL Press, Oxford, UK. References related to the manipulation and transformation of plant tissue include R. A. Dixon (ed.) (1985) *Plant Cell Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) *Methods for Plant Molecular Biology*, Academic Press, San Diego, Calif.; I. Potrykus (1991) *Ann. Rev. Plant Physiol. Plant Mol. Biol.* 42:205; Weising et al. (1988) *Annu. Rev. Genet.* 22:421, van Wordragen et al. (1992) *Plant Mol. Biol. Rep.* 19:12, Davey et al. (1989) *Plant Mol. Biol.* 13:273, Walden and Schell (1990) *Eur. J. Biochem.* 192:563, Joersbo and Brunstedt (1991) *Physiol. Plant.* 81:256 and references cited in those references. Abbreviations and nomenclature, where employed, are deemed standard in the filed and are commonly used in professional journals such as those cited herein.

All references cited in the present application are expressly incorporated by reference herein.

The following examples are provided for illustrative proposes are not intended to limit the scope of the invention as claimed herein. Any variations in the exemplified compositions and methods which occur to the skilled artisan are intended to fall within the scope of the present invention.

EXAMPLES

Example 1

Plant-expressible merA Coding Sequences

An overlap extension polymerase chain reaction (OE PCR) protocol, based on that of Ho et al. (1989) *Gene* 77:51–50, was used to mutagenize the merA coding sequence derived from Tn21 [Barrineau et al. (1984) *J. Mol. Appl. Molec. Genet.* 2:601–619] to adapt it for plant expressibility. The two halves of the merA sequence were amplified in separate PCR reactions, using pair of sense and antisense mutagenic oligonucleotide primers [5'S (SEQ ID NO:3) and 282–312A (SEQ ID NO:4) and 307–339S (SEQ ID NO:5) and 3'A (SEQ ID NO:6), respectively] and pNH6 as template. SEQ ID NO:3 includes BamHI and BglII recognition sites (GGATCC and AGATCT, respectively), a translation stop codon (TAA) in frame with the merA coding sequence, a consensus Shine-Delgarno bacterial ribosome binding site (AGAAGG) [Stormo et al. (1982) *Nucleic Acids Res.* 10:2971–2996], and potentially important plant translation sequences (AACCACA) [Heidecker and Menning (1986) *Ann. Rev. Plant Physiol.* 37:451–462]. The 3'S primer (SEQ ID NO:6) separated the merA coding sequence form the GC-rich region downstream of the translation stop codon. Where mutagenic primers are used, the length of 99 nucleotides was chosen to maximize the amount of the gene which is changes while minimizing the errors which might be introduced in each oligonucleotide.

Each PCR reaction contained 10 ng pNH6, 1.5 mM $MgCl_2$, 5% DMSO, 100 µM deoxynucleotide triphosphates, 45 pmol of each oligonucleotide primer as appropriate, 1.5 units Taq polymerase (Boehringer Mannheim Corp., Indianapolis, Ind.) and was carried out for 35 cycles (94° C. 1 min, 42° C. 1 min and 72° C. 2 min). After gel purification, the 5' and 3' fragments were joined in a PCR reaction using identical reaction conditions and the 5'S and 3'S primers (SEQ ID NO:1 and 4, respectively) to produce the NS2 amplimer. The NS2 amplimer was cleaved in the flanking BamHI and PstI sites, ligated into the BamHI/PstI replacement region of the multilinker of pBluescriptSKII(−) vector (Stratagene, La Jolla, Calif.) to produce pNS2, and the ligation mixture was transformed into Hg++-supersensitive *E. coli* (pPB111-47). *E. coli* (pPB111-47)(pNS2) grew well when replica plated onto medium containing 200 µM $HgCl_2$; the hypersensitive parental strain did not grow on 25–200 µM $HgCl_2$.

Example 2

DNA Sequence Determination

DNA sequences were determined for plant expressible metal resistance coding sequences to verify that desired mutagenized changes were made via the overlap extension PCR procedures.

Sequence determinations of single-stranded and double-stranded DNAs were carried out by the dideoxynucleotide chain termination procedure [Sanger et al. (1977) *Proc. Natl. Acad. Sci. USA* 74:8073–8077], with a Sequenase kit from United States Biochemical Corp., Cleveland, Ohio) or an automated fluorescence based system (Applied Biosystems, Foster City, Calif.).

Example 3

Bacterial Assays of Metal Resistance

*E. coli* SK1592 is Gal⁻, Thi⁻, T1$^R$, EndA⁻, hsdR4, sbcB15, Sup, and is highly proficient as a host in transformation.

pDMT10 is a pTZ vector (Pharmacia, Piscataway, N.J.) which carries an insert of all the genes of the mer operon (merT, merC, merP and merA). pDU202 is also a wild-type met plasmid. PDU202 carriers the wild-type mer operon. Both these plasmids confer a mercury resistant phenotype on *E. coli* strains which harbor it. pPB111-47 contains the mer operon within an R100 plasmid, but it contains a Tn5 insertion in the merA gene; it is suitable as a host for recombinant plasmids. The phenotype of *E. coli* strains carrying this plasmid is mercury hypersensitivity. For routine growth, *E. coli* strains are grown on LB media at 37° C. No potentially inhibitory compounds are incorporated into the medium unless otherwise noted.

The minimum $HgCl_2$ concentration to inhibit *E. coli* growth is 5 µM, and 10µ HgCl was used for selections. *E. coli* colonies which grew on LB plates containing 5, 10 and 50 µM $HgCl_2$ were considered to be mercury resistant. Selection of plasmids was performed by the inclusion of 50 µg/ml kanamycin and/or 100 µg/ml ampicillin.

Figure 2:
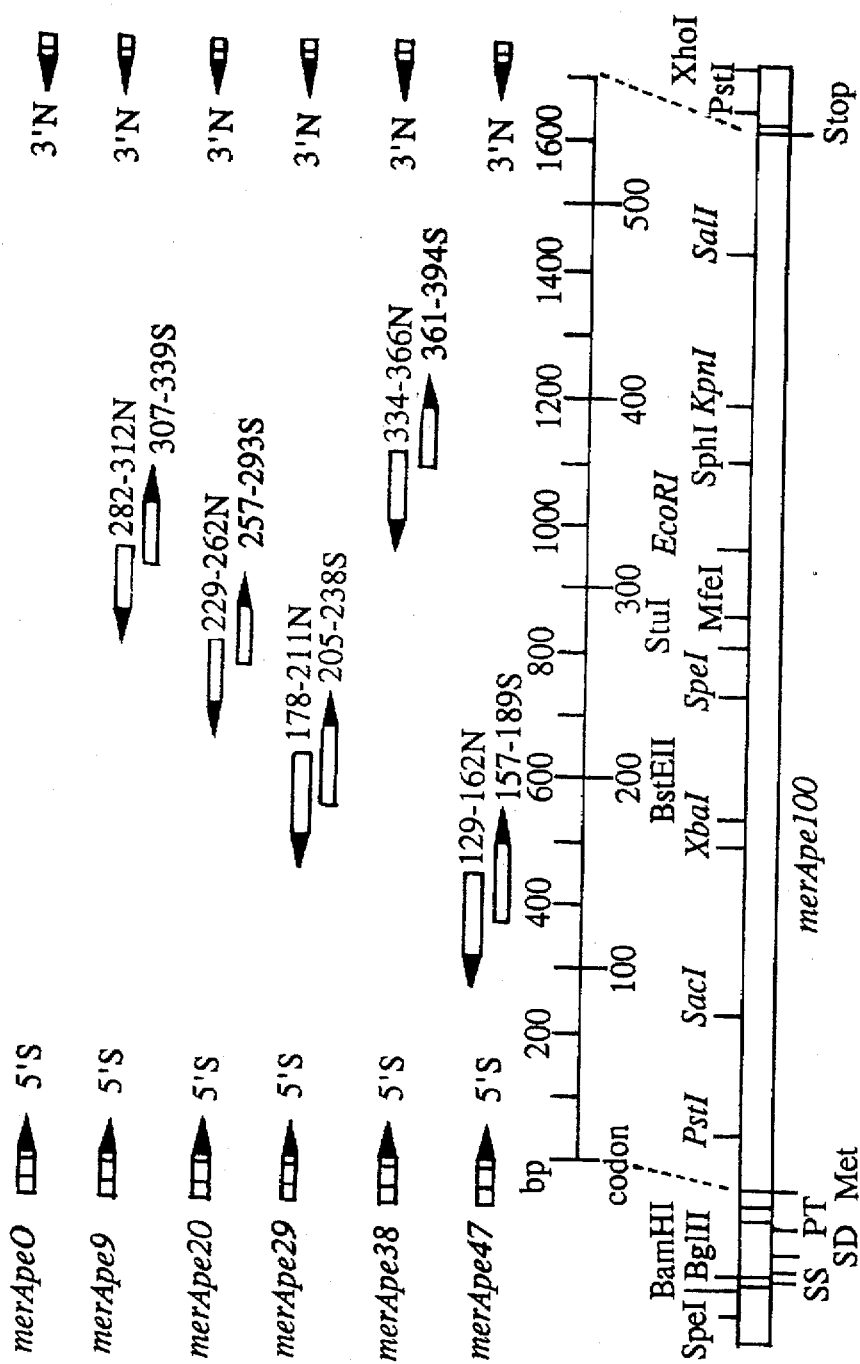
FIG. 2 diagrammatically illustrates strategies for the construction of merA sequences designed to be plant-expressible. The overlap extension PCR technique is used to produce the plant expressible merA derivatives. For example, to make merApe9, two fragment were synthesized by priming OE PCR reactions with merA (see SEQ ID NO:1) and two pairs of primers (5'S and 282/312N, i.e., SEQ ID NO:3 and NO:4; 307–339S and 3'N, SEQ ID NO:5 and NO:6). The two reaction products are purified and joined in a second PCR reaction using 5'S and 3'N (SEQ ID NO:3 and NO:6) as primers. Three more rounds of mutagenesis are carried out, each time starting with the preceding constructs, resulted in merApe38, which has 38% synthetic sequences. Primer sequences are given in Table 2 hereinbelow. After primer, merApe100 has 100% idealized sequence (for plant expression) and contains additional restriction sites as the result of silent base changes relative to the coding sequence of the naturally occurring merA coding sequence.

The wild-type merA coding sequence and mutated coding sequences were inserted under the regulatory control of the lac promoter into *E. coli*-compatible plasmids for testing effect on mercury sensitivity. pNS2 contains the merApe9 coding sequence (see SEQ ID NO:15), pNS5 contains the merApe38 coding sequence (see SEQ ID NO:13) and pNS100 contains the merApe100 coding sequence (see FIG. 2).

Sensitivity assays were carried out using the filter disk technique to determine the phenotypes of various genotypes of *E. coli* strains. Solid medium in these experiments was Tryptone agar for $HgCl_2$, $HAuCl_4$, $NiCl_2$ and $CoCl_2$. HMM medium with glycerol phosphate as the phosphate source [LaRossa et al. (1994) *J. Indus. Microbiol.* in press] was used in some experiments to prevent the precipitation of some metals. HMM contains 40 mM MOPS buffer, pH 7.3, 50 mM KCl, 10 mM $NH_4Cl$, 0.5 mM $MgSO_4$, 0.4% glucose, 1 mM glycerol-2-phosphate adn 1 µM $FeCl_3$. The results are summarized in Table 1:

TABLE 1

| | | | | Filter Disk Assay for Metal Ion Sensitivity* ← plasmid, strain, and Hg⁺⁺ sensitivity → | | | |
|---|---|---|---|---|---|---|---|
| Metal Salt | 2 ul /disk [con.] | SK 1592 Hg$^s$ | SK1592/ pNS2 Hg$^r$ | SK1592/ pPB111-47 Hg$^{ss}$ | SK1592/ pPB111-47/ pNS2 Hg$^r$ | SK1592/ pB111-47/ pNS5 Hg$^r$ | DU1040 pDU202 Hg$^r$ |
| $HgCl_2$ | 0.1 M | 25 mm | 20 mm | 30 mm | 14 mm | 14 mm | 15 mm |
| $HAuCl_4$ | 0.2 M | 20 mm | 16 mm | 20 mm | 15.5 mm | | 16 mm |
| $NiCl_2$ | 1.0 M | 17 mm | 17 mm | 16 mm | 13.5 mm | | 14 mm |
| $CoCl_2$ | 1.0 M | 19 mm | 19 mm | 17 mm | 15 mm | | 15 mm |
| **$HgCl_2$ | 0.1 M | 34 mm | 28 mm | | | | |
| **$HAuCl_4$ | 0.2 M | 25 mm | 18 mm | | | | |
| **$CuCl_2$ | 1.0 M | 30 mm | 25 mm | | | | |

*The mer operon is induced to maximum expression by Hg⁺⁺ ion. Experiments using trace amounts of Hg⁺⁺ in the plates (not shown) altered the actual killing zone sizes but does not significantly alter the interpretation of the data presented above. These results have been repeated several times and the zone of inhibition varies by less than 1 mm per experiment. Experiments in the top half of the table used tryptone plates.
**The last three disk assays used HMM media with glycerol phosphate as a phosphate source [LaRossa et al. (1994) J. Indus. Microbiol. (in press) to prevent the precipitation of some metals.

The results in Table 1 demonstrate that merA (or the mutated sequences thereof) can mediate significant resistance to both mercuric and auric ions. *E. coli* strains which contain merA in combination with the merT transport protein show some resistance to Co and Ni divalent cations.

Example 4

Construction of Plant Expression Constructs

Recombinant DNA methods were performed according to established methods (Sambrook et al. (1989) supra). pNS2 was cut with BamHI just upstream of the merA coding sequence and XhoI in the multilinker downstream of merA. This fragment was inserted into the replacement regions of the binary plant expression vector pVSTI [Malik and Wahab (1993) *J. Plant Biochem. Biotech.* 2:69-70] to produce pPENS2. The merApe9 coding sequence is expressed in plants under the regulatory control of the CaMV 35S promoter and nos polyadenylation signals. Agrobacterium-mediated transformation of *Arabidopsis thaliana* var. RLD root explants essentially as described by Marton (1991) *Plant Cell. Rep.* 10:235-239. Large numbers of independent transgenic shoot resulted, and these shoots were planted in soil, fed topically and allowed to go to seed (T1 seeds).

Example 5

Generation of Transgenic Plants

Agrobacterium-mediated transformation of *Arabidopsis thaliana* var. RLD root explants essentially as described by Marton (1991) *Plant Cell. Rep.* 10:235-239. Large numbers of independent transgenic shoot resulted, and these shoots were planted in soil, fed topically and allowed to go to seed (T1 seeds). The T1 seeds from transgenic plant line NS2-6 germinated and grew on plant growth solidified agar medium [Murashige and Skoog (1964) *Plant. Physiol.* 15:485] containing 60 µM $HgCl_2$. Almost all transgenic lines grew on 20-100 µM$HgCl_2$. 100 µm $HgCl_2$ corresponds to 40 ppm. Untransformed RLD control seeds exposed to 20 µM or higher concentrations of $HgCl_2$ either did not germinate or died shortly after germination.

Example 6

Metal Resistance of Transgenic Plants

Growth of parental plantlets of Arabidopsis var. RLD, and transgenic plants carrying either the merApe9 plant-expressible gene or a β-glucuronidase plant expressible construct (GUS, as a control) was tested on Murashige and Skoog plant growth medium [Murashige and Skoog (1964) supra] with and without metal ions.

The T1 seeds from transgenic plant line NS2-6 germinated and grew on plant growth solidified agar medium containing 60 µM$HgCl_2$. Almost all transgenic lines containing and expressing merApe9 grew on 20-60 µM $HgCl_2$. Untransformed RLD control seeds and the GUS control transgenic plants exposed to 20 µM or higher concentrations of $HgCl_2$ either did not germinate or died shortly after germination.

The merApe9 transgenic plants grow significantly better than the GUS and untransformed controls on plant growth solidified medium containing 100-500 µM $AuHCl_4$. Root growth Physiol. is most dramatically affected on the medium containing gold ions.

Plants resistant to organomercurial compounds such as methylmercury are produced by genetically engineering plant cells to contain and express a plant expressible merB coding sequence as well as a plant-expressible merA coding sequence.

Example 7

Mercuric Ion Reduction in Transgenic Plants

Transgenic seedlings containing the plant-expressible metal resistance coding sequence (merApe9) catalyzed significant reduction of divalent mercury to elemental mercury relative to the chemical reduction of mercuric ions observed with control seedlings of the parental RLD lineage.

About 10 seedlings (10 days old, 0.05 g total wet weight) were incubated in 2 ml assay medium (25 mM sodium phosphate pH 7.0, 5 µM $HgCl_2$) in glass bubbler tubas designed with an outlet vent for collection of sparged gas. The amount of elemental mercury ($Hg^0$) produced was assayed by bubbling air through the sample (for 12 sec) beginning at 8 sec after placing the seedlings into the assay medium. Samples were then re-assayed every min over the next 10 min. so that the rate of mercury evolution could be determined. The volatilized $Hg^0$ for each sampling was measured by passing each sample over the gold foil membrane resister on a Jerome 431 mercury vapor analyzer (Arizona Instrument Corp., Tempe, Ariz.). The instrument was repeatedly standardized with known quantities of $Hg^0$ (1-50 ng), reduced form $HgCl_2$ with excess $SnCl_2$. The amount of $Hg^0$ evolved was normalized to the amount of tissue used in each assay reaction. It was found to be necessary to bake all glassware for the assays at 180° C. for 6 hrs before use.

Example 8

Plant Expressible merB Coding Sequence

A plant-expressible merB coding sequence is engineered using a naturally occurring merB gene and adapting it by overlap extension PCR in an analogous manner as used for the adaptation of merA as described hereinabove.

The merB gene is cloned on a 1.5 kb EcoRI restriction fragment from pCT12, a broad spectrum resistance plasmid in *Salmonella typhimurium*. The plant-expressible merB is produced by PCR amplification using the MerB5'S and MerB3'A primers. The MerB5'S primer contains BamHI, EcoRI and SalGI restriction sites upstream of a bacterial Shine-Delgarno sequence and synthetic plant animal ribosome binding signals upstream of the first six codons of the merB coding sequence. The MerB3'A primer contains the last five codons of merB, the stop codon and HindIII, EcoRI and BamHI recognition sites. The sequences of these primers are as follows:

---

MerB5'S (SEQ ID NO: 17)
5'-CGCGTCGGATCCAGAATTCGTCGACTAACCAGGAGCCACAATGAAGCTCGCCCCATAT-3'
MerB3'A (SEQ ID NO: 18)
5'-CGTATCGGATCCGAATTCAAGCTTATCACGGTGTCCATAGATGA-3'

---

The PCR reaction product is cut with BamHI and then cloned into BamHI-cut pBS-SK to give pBS-KSII' (See FIG. 4).

Resistance to organomercurial compounds can be confirmed in an *E. coli* host which also contains merA, for example on plasmid pDU202 [Foster, T. J. (1983) *Microbiol. Rev.* 47:361–409]. For testing the organomercurial resistance phenotype, PCMB is applied onto a sterile filter paper disk (5 μl of 10 mM solution) on the surface of soft agar seeded with the *E. coli* strain carrying the gene to be tested.

For plant gene expression, the plant expressible merB coding sequence is cloned from pBS-SKII⁻ into a binary vector for plant transformation using BamHI, EcoRI or other restriction enzymes which will produce the desired restriction fragment with the plant-expressible coding sequence. For example, pBI121 (Clontech, Palo Alto, Calif.) can be digested with BamHI, and the merB adapted gene can be inserted downstream of the 35SC promoter to give high constitutive levels of gene expression in plant cells stably transformed to contain this construct.

Where resistance is desired to metal ions and organomercurials the transgenic plant should also contain a plant-expressible merA coding sequence as taught hereinabove.

Example 9

PCR mutagenesis Strategy

Figure 1D:
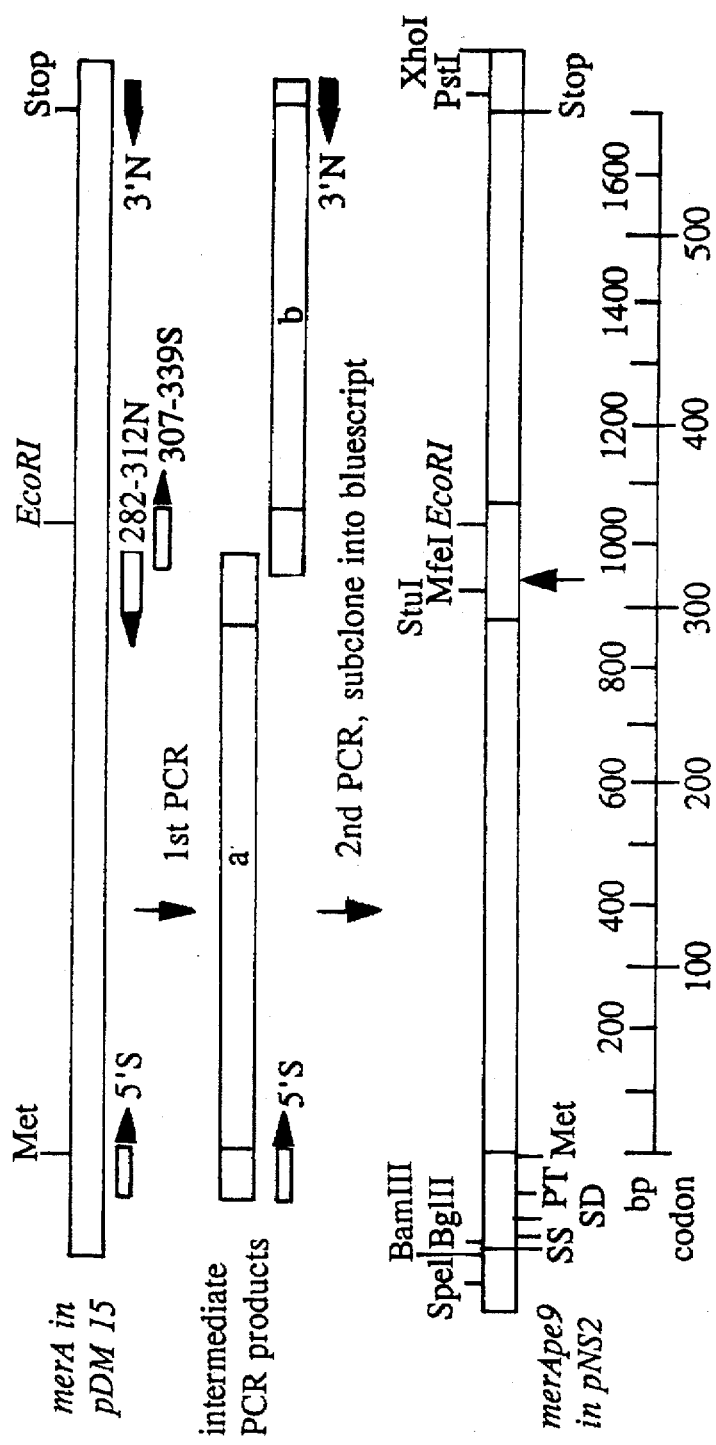

The strategy for generating plant-expressible merA coding sequences other than merApe9 is presented in FIG. 2, together with the sequences of the primers to be used in PCR as described hereinabove and with reference to FIG. 1 and its description. Mutagenic primer sequences are given in Table 2 and in SEQ ID NOs:3–14. The merA coding sequence of Tn21 is provided in SEQ ID NO:1, from nucleotide 14 to nucleotide 1708, and is taken from Barrineau et al. (1984) *J. Mol. Appl. Genet.* 2:601–619. Sequences of merApe 9, merApe 20, merApe 29, merApe 38, and merApe 47 are disclosed herein.

TABLE 2

OLIGONUCLEOTIDE SEQUENCES

```
5'S (SEQ ID NO: 3)
         10            20           30               40            50
      CTAGAACTAG    TGGATCCCTA   GATCTAAGAA     GGAACCACAA TG    AGCACTCT
      Bluescript homology BglII Shine-Dalgarno Start MerA homology
                                     TAA         AACCACA
                                     STOP        Plant Translation
                                                 Control Sequence
         59
      CAAAATCAC-3'
3'N (SEQ ID NO: 6)
         10            20           30             36
      TATCGAATTC    CTGCAGCCTC   ACCCGGCGCA      GCAGGA
1–19S (SEQ ID NO: 21)
         10            20           30              40             50
      AAGAAGAAC     CACAATGtct   ACTCTgAAgA      TCACtGGtAT     GACTTGTGAC
         60            70           73
      TCtTGtGCAG    TGCATGTCAA   GGA*
282–312N (SEQ ID NO: 4)
         10            20           30              40             50
      CCtATaGCTG    GGTCTTCaCG   aAAGAAgAGa      GTGgaGCGtG     CaAGaATgGT
         60            70           80              90             92
      CACtTTaGCa    CCaAGaCGtG   CaAAgGCCTG      cGCcAGcTCc     AG
549–565N (SEQ ID NO: 22)
         10            20           30              40             50     52
      TCGAATTCCT    GCAGCCTtAg   CCaGCaCAGC      AGctcAGCTG     CTTCACATCC TT*
307–339S (SEQ ID NO: 5)
         10            20           30              40             50
      GAAGACCCAG    CTATAGGTGA   AGCTGTTACT      GCTGCATTTC     GCATGGAAGG
         60            70           80              90             99
      CATTGAAGTG    CGTGAGCATA   CTCAAGCAAG      CCAAGTTGCC     TATATCAAT
229–262N (SEQ ID NO: 7)
         10            20           30              40             50
      GCTTCAGTGG    AAGTCCAGTA   AGGAGTGTCC      TTGAGACCAG     GAATTGGTGG
         60            70           80              90             101
      AACAGCTGGG    CTTGCACCAG   TGGCAATGAG      ACAGCGGTCG     AATGCCACCA C
257–293S (SEQ ID NO: 8)
         10            20           30              40             50
      TGGACTTCCA    CTGAAGCACT   AGTGTCTGAG      ACCATTCCAA     AGCGTCTTGC
         60            70           80              90             100
      AGTCATTGGC    TCCTCTGTGG   TGGCTCTTGA      ACTTGCCCAG     GCCTTTGCAC
         109
      GTCTTGGTG
334–366N (SEQ ID NO: 11)
         10            20           30              40             50
      CACGACCAGT    TGCAACAAGG   AGTTTGTCTG      CACGAAGTTC     ACCATGAGCA
         60            70           80              90             100
      GTGGTAAGGA    CGAATTCACC   ATCACCTTCA      CCATTGATAT     AGGCAACTTG
361–394S (SEQ ID NO: 12)
         10            20           30              40             50
      TGTTGCAACT    GGTCGTGCAC   CAAACACTCG      CAAACTGGCA     CTTGATGCAA
         60            70           80              90             99
      CTGGTGTGAC    CCTTACTCCA   CAAGGTGCTA      TTGTCATCGA     CCCCGGCAT
205–238S (SEQ ID NO: 10)
         10            20           30              40             50
```

TABLE 2-continued

| OLIGONUCLEOTIDE SEQUENCES | | | | |
|---|---|---|---|---|
| GCTTCATGGC | TCTGCACGTT | TCAAGGACAA | CCGTAACCTC | ATTGTTCAAC |
| 60 | 70 | 80 | 90 | 99 |
| TTAATGATGG | TGGTGAACGT | GTGGTGGCTT | TTGACCGCTG | TCTCATTGC |
| 383–416N (SEQ ID NO: 23) | | | | |
| 10 | 20 | 30 | 40 | 50 |
| CATACACAAA | TTGTGGTTGA | TCAGTGCAAT | CACCAGCTGC | ATAGATGTGT |
| 60 | 70 | 80 | 90 | 99 |
| TCCACAGAGG | TACGCATACC | TGGATCAATC | ACAATAGCAC | CTTGTGGAG |
| 410–437S (SEQ ID NO: 24) | | | | |
| 10 | 20 | 30 | 40 | 50 |
| ACCACAATTT | GTGTATGTTG | CTGCTGCTGC | TGGTACCCGT | GCTGCTATCA |
| 60 | 70 | 80 | 90 | 99 |
| ACATGACTGG | TGGTGATGCT | GCCCTCAACC | TCACCGCGAT | GCCGGCCGT |
| 178–211N (SEQ ID NO: 9) | | | | |
| 10 | 20 | 30 | 40 | 50 |
| GTGCAGAGCC | ATGAAGCACA | GTGATGGCTG | GGTTACCTTC | TAGAATACCT |
| 60 | 70 | 80 | 90 | 99 |
| TCATACTTTG | CATGACGAAG | TTCATCAACA | CGGGCCTGCT | GCTGGGCCA |
| 135–162N (SEQ ID NO: 25) | | | | |
| 10 | 20 | 30 | 40 | 50 |
| CAAATGGAGA | TTCACGACGA | AGATGAGCAA | TGTGAGCAGC | ACGAATCATG |
| 60 | 70 | 80 | 90 | 99 |
| ATCTTGCTTG | GCACACAACC | AACATTAACA | CAGGTGCCGC | CGATGGTGC |
| 156–189S (SEQ ID NO: 26) | | | | |
| 10 | 20 | 30 | 40 | 50 |
| TCGTGAATCT | CCATTTGATG | GTGGCATTGC | TGCAACCACT | CCAACCATTC |
| 60 | 70 | 80 | 90 | 99 |
| AACGTACTGC | ACTCCTTGCA | CAACAACAAG | CACGTGTTGA | TGAACTTCG |

Example 10

Generation of Random Mutations in merA

Where it is desired to express an altered merA gene in plants, the starting material for the generation of random mutations in the merA coding sequence, the starting material is purified DNA comprising one of merApe9, merApe20, merApe29, merApe38, merApe47 and merApe100, or other plant-expressible merA coding sequences. Mutagenic PCR is carried out as essentially as described by Muhlrad et al. (1992) *Yeast* 8:79–82. Template DNA (e.g., pNS2) is linearized a restriction enzyme (which cuts one time in the plasmid, outside the merA coding sequence) and diluted top 10 ng/ml. Concentrated reaction buffer is added to give final concentrations of 100 mM Tris-HCl, pH 8.3, 500 mM KCl, 0.1% (w/v) gelatin, and nucleotide triphosphates are added to a final concentration 1 mM each of dGTP, dCTP and dTTP and 200 μM dATP, primers are added, and 2.5 units of AmpliTAQ DNA polymerass (Cetus) is added to start the reaction. Each reaction is supplemented with $MgCl_2$ at a concentration of from 1.5 to 6 mM and $MnCl_2$ is added for a final concentration of 0.05 to 0.65 mM. Reactions were carried out in a volume of 25 μl each after overlayering with 100 μl mineral oil.

Untreated plasmid DNA (100 ng) is then mixed with the mutagenic PCR product (20μ) and transformed into competent *E. coli* cells, with selection for drug resistance carried by the vector portion of the plasmid carrying the coding sequence which was used as template in the mutagnic PCR reaction. In the cells, the PCR products (containing mutations relative to the starting template) recombine via homologons sequences into the plasmid. Then the potential mutants are screened for novel phenotypes useful in the practice of the present invention.

Transformants are then tested for the maintenance of resistance to mercuric ion as described above, and they are tested for cross-resistance to other metal ions.

TABLE 3

| SEQ ID NO: 1 MerA from Tn21 | | | | | | | | | | | | | | | | | |
|---|---|---|---|---|---|---|---|---|---|---|---|---|---|---|---|---|---|
| AAGGAACGAT | | | GGT | ATG | AGC | ACT | CTC | AAA | ATC | ACC | GGC | ATG | ACT | TGC | GAC | | |
| | | | | Met | Ser | Thr | Leu | Lys | Ile | Thr | Gly | Met | Thr | Cys | Asp | | |
| | | | | 1 | | | | 5 | | | | | 10 | | | | |
| TCG | TGC | GCA | GTG | CAT | GTC | AAG | GAC | GCC | CTG | GAG | AAA | GTG | CCC | GGC | GTG | | |
| Ser | Cys | Ala | Val | His | Val | Lys | Asp | Ala | Leu | Glu | Lys | Val | Pro | Gly | Val | | |
| | | 15 | | | | | 20 | | | | | 25 | | | | | |
| CAA | TCA | GCG | GAT | GTC | TCC | TAC | GCC | AAG | GGC | AGC | GCC | AAG | CTC | GCC | ATT | | |
| Gln | Ser | Ala | Asp | Val | Ser | Tyr | Ala | Lys | Gly | Ser | Ala | Lys | Leu | Ala | Ile | | |
| | | 30 | | | | 35 | | | | | 40 | | | | | | |
| GAG | GTC | GGC | ACG | TCA | CCC | GAC | GCG | CTG | ACG | GCC | GCT | GTA | GCT | GGA | CTC | | |
| Glu | Val | Gly | Thr | Ser | Pro | Asp | Ala | Leu | Thr | Ala | Ala | Val | Ala | Gly | Leu | | |
| 45 | | | | | 50 | | | | | | 55 | | | | | 60 | |
| GGT | TAT | CGG | GCC | ACG | CTG | GCC | GAT | GCC | CCC | TCA | GTT | TCG | ACG | CCG | GGC | | |
| Gly | Tyr | Arg | Ala | Thr | Leu | Ala | Asp | Ala | Pro | Ser | Val | Ser | Thr | Pro | Gly | | |
| | | | | 65 | | | | | 70 | | | | | 75 | | | |

TABLE 3-continued

| SEQ ID NO: 1 MerA from Tn21 |
|---|

| GGA | TTG | CTC | GAC | AAG | ATG | CGC | GAT | CTG | CTG | GGC | AGA | AAC | GAC | AAG | ACG |
|---|---|---|---|---|---|---|---|---|---|---|---|---|---|---|---|
| Gly | Leu | Leu | Asp 80 | Lys | Met | Arg | Asp | Leu 85 | Leu | Gly | Arg | Asn | Asp 90 | Lys | Thr |
| GGT | AGC | AGC | GGC | GCA | TTG | CAT | ATC | GCC | GTC | ATC | GGC | AGC | GGC | GGG | GCC |
| Gly | Ser | Ser 95 | Gly | Ala | Leu | His | Ile 100 | Ala | Val | Ile | Gly | Ser 105 | Gly | Gly | Ala |
| GCG | ATG | GCA | GCG | GCG | CTG | AAG | GCC | GTC | GAG | CAA | GGC | GCA | CCT | GTC | ACG |
| Ala | Met 110 | Ala | Ala | Ala | Leu | Lys 115 | Ala | Val | Glu | Gln | Gly 120 | Ala | Pro | Val | Thr |
| CTG | ATC | GAG | CGC | GGC | ACC | ATC | GGC | GGC | ACC | TGC | GTC | AAT | GTC | GGT | TGT |
| Leu 125 | Ile | Glu | Arg | Gly | Thr 130 | Ile | Gly | Gly | Thr | Cys 135 | Val | Asn | Val | Gly | Cys 140 |
| GTG | CCG | TCC | AAG | ATC | ATG | ATC | CGC | GCC | GCC | CAT | ATC | GCC | CAT | CTG | CGC |
| Val | Pro | Ser | Lys | Ile 145 | Met | Ile | Arg | Ala | Ala 150 | His | Ile | Ala | His | Leu 155 | Arg |
| CGG | GAA | AGC | CCG | TTC | GAT | GGC | GGC | ATC | GCC | GCT | ACC | ACG | CCG | ACC | ATC |
| Arg | Glu | Ser | Pro 160 | Phe | Asp | Gly | Gly | Ile 165 | Ala | Ala | Thr | Thr | Pro 170 | Thr | Ile |
| CAG | CGC | ACG | GCG | CTG | CTG | GCC | CAG | CAG | CAG | GCC | CGC | GTC | GAT | GAA | CTG |
| Gln | Arg | Thr 175 | Ala | Leu | Leu | Ala | Gln 180 | Gln | Gln | Ala | Arg | Val 185 | Asp | Glu | Leu |
| CGC | CAC | GCC | AAG | TAC | GAA | GGC | ATC | TTG | GAG | GGC | AAT | CCG | GCG | ATC | ACT |
| Arg | His 190 | Ala | Lys | Tyr | Glu | Gly 195 | Ile | Leu | Glu | Gly | Asn 200 | Pro | Ala | Ile | Thr |
| GTG | CTG | CAC | GGC | TCC | GCC | CGC | TTT | AAG | GAC | AAT | CGC | AAC | CTG | ATC | GTG |
| Val 205 | Leu | His | Gly | Ser | Ala 210 | Arg | Phe | Lys | Asp | Asn 215 | Arg | Asn | Leu | Ile | Val 220 |
| CAA | CTC | AAC | GAC | GGC | GGC | GAG | CGC | GTG | GTG | GCA | TTC | GAC | CGC | TGC | CTG |
| Gln | Leu | Asn | Asp | Gly 225 | Gly | Glu | Arg | Val | Val 230 | Ala | Phe | Asp | Arg | Cys 235 | Leu |
| ATC | GCC | ACC | GGC | GCG | AGC | CCG | GCC | GTG | CCG | CCG | ATT | CCC | GGC | CTG | AAA |
| Ile | Ala | Thr | Gly 240 | Ala | Ser | Pro | Ala | Val 245 | Pro | Pro | Ile | Pro | Gly 250 | Leu | Lys |
| GAC | ACT | CCG | TAC | TGG | ACT | TCC | ACT | GAA | GCG | CTG | GTC | AGC | GAG | ACG | ATT |
| Asp | Thr | Pro 255 | Tyr | Trp | Thr | Ser | Thr 260 | Glu | Ala | Leu | Val | Ser 265 | Glu | Thr | Ile |
| CCT | AAG | CGC | CTG | GCC | GTG | ATT | GGC | TCA | TCA | GTG | CTG | GCG | CTG | GAG | CTG |
| Pro | Lys 270 | Arg | Leu | Ala | Val | Ile 275 | Gly | Ser | Ser | Val | Leu 280 | Ala | Leu | Glu | Leu |
| GCG | CAG | GCG | TTC | GCC | CGA | CTC | GGA | GCG | AAG | GTG | ACG | ATC | CTG | GCT | CGC |
| Ala 285 | Gln | Ala | Phe | Ala | Arg 290 | Leu | Gly | Ala | Lys | Val 295 | Thr | Ile | Leu | Ala | Arg 300 |
| AGC | ACG | CTG | TTC | TTC | CGC | GAA | GAC | CCA | GCT | ATA | GGC | GAA | GCT | GTC | ACG |
| Ser | Thr | Leu | Phe | Phe 305 | Arg | Glu | Asp | Pro | Ala 310 | Ile | Gly | Glu | Ala | Val 315 | Thr |
| GCC | GCA | TTC | CGG | ATG | GAG | GGC | ATC | GAG | GTG | AGG | GAA | CAC | ACC | CAG | GCC |
| Ala | Ala | Phe | Arg 320 | Met | Glu | Gly | Ile | Glu 325 | Val | Arg | Glu | His | Thr 330 | Gln | Ala |
| AGC | CAG | GTC | GCG | TAT | ATC | AAT | GGT | GAA | GGG | GAC | GGC | GAA | TTC | GTG | CTC |
| Ser | Gln | Val 335 | Ala | Tyr | Ile | Asn | Gly 340 | Glu | Gly | Asp | Gly | Glu 345 | Phe | Val | Leu |
| ACC | ACG | GCG | CAC | GGC | GAA | CTG | CGC | GCC | GAC | AAG | CTG | CTG | GTC | GCC | ACC |
| Thr | Thr 350 | Ala | His | Gly | Glu | Leu 355 | Arg | Ala | Asp | Lys | Leu 360 | Leu | Val | Ala | Thr |
| GGC | CGC | GCG | CCC | AAC | ACA | CGC | AAG | CTG | GCA | CTG | GAT | GCG | ACG | GGC | GTC |
| Gly 365 | Arg | Ala | Pro | Asn | Thr 370 | Arg | Lys | Leu | Ala | Leu 375 | Asp | Ala | Thr | Gly | Val 380 |
| ACG | CTC | ACC | CCC | CAA | GGC | GCT | ATC | GTC | ATC | GAC | CCC | GGC | ATG | CGT | ACA |
| Thr | Leu | Thr | Pro | Gln 385 | Gly | Ala | Ile | Val | Ile 390 | Asp | Pro | Gly | Met | Arg 395 | Thr |
| AGC | GTG | GAA | CAC | ATC | TAC | GCC | GCA | GGC | GAC | TGC | ACC | GAC | CAG | CCG | CAG |
| Ser | Val | Glu | His 400 | Ile | Tyr | Ala | Ala | Gly 405 | Asp | Cys | Thr | Asp | Gln 410 | Pro | Gln |
| TTC | GTC | TAT | GTG | GCG | GCA | GCG | GCC | GGC | ACT | CGC | GCC | GCG | ATC | AAC | ATG |
| Phe | Val | Tyr 415 | Val | Ala | Ala | Ala | Ala 420 | Gly | Thr | Arg | Ala | Ala 425 | Ile | Asn | Met |
| ACC | GGC | GGT | GAC | GCC | GCC | CTG | AAC | CTG | ACC | GCG | ATG | CCG | GCC | GTG | GTG |
| Thr | Gly 430 | Gly | Asp | Ala | Ala | Leu 435 | Asn | Leu | Thr | Ala | Met 440 | Pro | Ala | Val | Val |
| TTC | ACC | GAC | CCG | CAA | GTG | GCG | ACC | GTA | GGC | TAC | AGC | GAG | GCG | GAA | GCG |
| Phe | Thr | Asp | Pro | Gln 450 | Val | Ala | Thr | Val | Gly | Tyr 455 | Ser | Glu | Ala | Glu | Ala 460 |
| CAC | CAT | GAC | GGC | ATC | AAA | ACT | GAT | AGT | CGC | ACG | CTA | ACG | CTG | GAC | AAC |
| His | His | Asp | Gly | Ile 465 | Lys | Thr | Asp | Ser | Arg 470 | Thr | Leu | Thr | Leu | Asp | Asn 475 |
| GTG | CCG | CGC | GCG | CTC | GCC | AAC | TTC | GAC | ACG | CGC | GGC | TTC | ATC | AAA | CTG |
| Val | Pro | Arg | Ala | Leu | Ala | Asn | Phe | Asp | Thr | Arg | Gly | Phe | Ile | Lys | Leu |

TABLE 3-continued

SEQ ID NO: 1 MerA from Tn21

| | | | | | | | | | | | | | | | |
|---|---|---|---|---|---|---|---|---|---|---|---|---|---|---|---|
| | | | 480 | | | | | 485 | | | | | 490 | | |
| GTG | GTT | GAA | GAA | GGG | AGC | GGA | CGA | CTG | ATC | GGC | GTC | CAG | GCA | GTG | GCC |
| Val | Val | Glu | Glu | Gly | Ser | Gly | Arg | Leu | Ile | Gly | Val | Gln | Ala | Val | Ala |
| | | 495 | | | | | 500 | | | | | 505 | | | |
| CCG | GAA | GCG | GGC | GAA | CTG | ATC | CAG | ACG | GCC | GCA | CTG | GCG | ATT | CGC | AAC |
| Pro | Glu | Ala | Gly | Glu | Leu | Ile | Gln | Thr | Ala | Ala | Leu | Ala | Ile | Arg | Asn |
| | 510 | | | | | 515 | | | | | 520 | | | | |
| CGG | ATG | ACG | GTG | CAG | GAA | CTG | GCC | GAC | CAG | TTG | TTC | CCC | TAC | CTG | ACG |
| Arg | Met | Thr | Val | Gln | Glu | Leu | Ala | Asp | Gln | Leu | Phe | Pro | Tyr | Leu | Thr |
| 525 | | | | | 530 | | | | | 535 | | | | | 540 |
| ATG | GTC | GAA | GGG | TTG | AAG | CTC | GCG | GCG | CAG | ACC | TTC | AAC | AAG | GAT | GTG |
| Met | Val | Glu | Gly | Leu | Lys | Leu | Ala | Ala | Gln | Thr | Phe | Asn | Lys | Asp | Val |
| | | | | 545 | | | | | 550 | | | | | 555 | |
| AAG | CAG | CTT | TCC | TGC | TGC | GCC | GGG | TGA | GGACAAGGAG | GTGTGCGATG | | | | | |
| Lys | Gln | Leu | Ser | Cys | Cys | Ala | Gly | * | | | | | | | |
| | | | 560 | | | | | 565 | | | | | | | |

TABLE 4

MerApe 9 DNA and Amino Acid Sequences (SEQ ID NO: 15–16)

| | | | | | | | | | | | | | | | |
|---|---|---|---|---|---|---|---|---|---|---|---|---|---|---|---|
| CTAGAACTAG | | | TGGATCCCTA | | | GATCTAAGAA | | | GGAACCACA | | ATG | AGC | ACT | CTC | AAA |
| | | | | | | | | | | | Met | Ser | Thr | Leu | Lys |
| | | | | | | | | | | | 1 | | | | 5 |
| ATC | ACC | GGC | ATG | ACT | TGC | GAC | TCG | TGC | GCA | GTG | CAT | GTC | AAG | GAC | GCC |
| Ile | Thr | Gly | Met | Thr | Cys | Asp | Ser | Cys | Ala | Val | His | Val | Lys | Asp | Ala |
| | | | | 10 | | | | | 15 | | | | | 20 | |
| CTG | GAG | AAA | GTG | CCC | GGC | GTG | CAA | TCA | GCG | GAT | GTC | TCC | TAC | GCC | AAG |
| Leu | Glu | Lys | Val | Pro | Gly | Val | Gln | Ser | Ala | Asp | Val | Ser | Tyr | Ala | Lys |
| | | | 25 | | | | | 30 | | | | | | 35 | |
| GGC | AGC | GCC | AAG | CTC | GCC | ATT | GAG | GTC | GGC | ACG | TCA | CCC | GAC | GCG | CTG |
| Gly | Ser | Ala | Lys | Leu | Ala | Ile | Glu | Val | Gly | Thr | Ser | Pro | Asp | Ala | Leu |
| | | 40 | | | | | 45 | | | | | 50 | | | |
| ACG | GCC | GCT | GTA | GCT | GGA | CTC | GGT | TAT | CGG | GCC | ACG | CTG | GCC | GAT | GCC |
| Thr | Ala | Ala | Val | Ala | Gly | Leu | Gly | Tyr | Arg | Ala | Thr | Leu | Ala | Asp | Ala |
| | 55 | | | | | 60 | | | | | 65 | | | | |
| CCC | TCA | GTT | TCG | ACG | CCG | GGC | GGA | TTG | CTC | GAC | AAG | ATG | CGC | GAT | CTG |
| Pro | Ser | Val | Ser | Thr | Pro | Gly | Gly | Leu | Leu | Asp | Lys | Met | Arg | Asp | Leu |
| 70 | | | | | 75 | | | | | 80 | | | | | 85 |
| CTG | GGC | AGA | AAC | GAC | AAG | ACG | GGT | AGC | AGC | GGC | GCA | TTG | CAT | ATC | GCC |
| Leu | Gly | Arg | Asn | Asp | Lys | Thr | Gly | Ser | Ser | Gly | Ala | Leu | His | Ile | Ala |
| | | | | 90 | | | | | 95 | | | | | 100 | |
| GTC | ATC | GGC | AGC | GGC | GGG | GCC | GCG | ATG | GCA | GCG | GCG | CTG | AAG | GCC | GTC |
| Val | Ile | Gly | Ser | Gly | Gly | Ala | Ala | Met | Ala | Ala | Ala | Leu | Lys | Ala | Val |
| | | | | 105 | | | | | 110 | | | | | 115 | |
| GAG | CAA | GGC | GCA | CCT | GTC | ACG | CTG | ATC | GAG | CGC | GGC | ACC | ATC | GGC | GGC |
| Glu | Gln | Gly | Ala | Pro | Val | Thr | Leu | Ile | Glu | Arg | Gly | Thr | Ile | Gly | Gly |
| | | 120 | | | | | 125 | | | | | 130 | | | |
| ACC | TGC | GTC | AAT | GTC | GGT | TGT | GTG | CCG | TCC | AAG | ATC | ATG | ATC | CGC | GCC |
| Thr | Cys | Val | Asn | Val | Gly | Cys | Val | Pro | Ser | Lys | Ile | Met | Ile | Arg | Ala |
| | 135 | | | | | 140 | | | | | 145 | | | | |
| GCC | CAT | ATC | GCC | CAT | CTG | CGC | CGG | GAA | AGC | CCG | TTC | GAT | GGC | GGC | ATC |
| Ala | His | Ile | Ala | His | Leu | Arg | Arg | Glu | Ser | Pro | Phe | Asp | Gly | Gly | Ile |
| 150 | | | | | 155 | | | | | 160 | | | | | 165 |
| GCC | GCT | ACC | ACG | CCG | ACC | ATC | CAG | CGC | ACG | GCG | CTG | CTG | GCC | CAG | CAG |
| Ala | Ala | Thr | Thr | Pro | Thr | Ile | Gln | Arg | Thr | Ala | Leu | Leu | Ala | Gln | Gln |
| | | | | 170 | | | | | 175 | | | | | 180 | |
| CAG | GCC | CGC | GTC | GAT | GAA | CTG | CGC | CAC | GCC | AAG | TAC | GAA | GGC | ATC | TTG |
| Gln | Ala | Arg | Val | Asp | Glu | Leu | Arg | His | Ala | Lys | Tyr | Glu | Gly | Ile | Leu |
| | | | 185 | | | | | 190 | | | | | 195 | | |
| GAG | GGC | AAT | CCG | GCG | ATC | ACT | GTG | CTG | CAC | GGC | TCC | GCC | CGC | TTT | AAG |
| Glu | Gly | Asn | Pro | Ala | Ile | Thr | Val | Leu | His | Gly | Ser | Ala | Arg | Phe | Lye |
| | | 200 | | | | | 205 | | | | | 210 | | | |
| GAC | AAT | CGC | AAC | CTG | ATC | GTG | CAA | CTC | AAC | GAC | GGC | GGC | GAG | CGC | GTG |
| Asp | Asn | Arg | Asn | Leu | Ile | Val | Gln | Leu | Asn | Asp | Gly | Gly | Glu | Arg | Val |
| | 215 | | | | | 220 | | | | | 225 | | | | |
| GTG | GCA | TTC | GAC | CGC | TGC | CTG | ATC | GCC | ACC | GGC | GCG | AGC | CCG | GCC | GTG |
| Val | Ala | Phe | Asp | Arg | Cys | Leu | Ile | Ala | Thr | Gly | Ala | Ser | Pro | Ala | Val |
| 230 | | | | | 235 | | | | | 240 | | | | | 245 |
| CCG | CCG | ATT | CCC | GGC | CTG | AAA | GAC | ACT | CCG | TAC | TGG | ACT | TCC | ACT | GAA |
| Pro | Pro | Ile | Pro | Gly | Leu | Lys | Asp | Thr | Pro | Tyr | Trp | Thr | Ser | Thr | Glu |
| | | | | 250 | | | | | 255 | | | | | 260 | |
| GCG | CTG | GTC | AGC | GAG | ACG | ATT | CCT | AAG | CGC | CTG | GCC | GTG | ATT | GGC | TCA |
| Ala | Leu | Val | Ser | Glu | Thr | Ile | Pro | Lys | Arg | Leu | Ala | Val | Ile | Gly | Ser |

TABLE 4-continued

MerApe 9 DNA and Amino Acid Sequences (SEQ ID NO: 15-16)

| | | 265 | | | | | 270 | | | | | 275 | | |
|---|---|---|---|---|---|---|---|---|---|---|---|---|---|---|
| TCA | GTG | CTG | GCG | CTT | GAA | CTT | GCC | CAG | GCC | TTT | GCA | CGT | CTT | GGT | GCT |
| Ser | Val | Leu | Ala | Leu | Glu | Leu | Ala | Gln | Ala | Phe | Ala | Arg | Leu | Gly | Ala |
| | | 280 | | | | | 285 | | | | | 290 | | | |
| AAA | GTG | ACC | ATT | CTT | GCA | CGC | TCC | ACT | CTC | TTC | TTT | CGT | GAA | GAC | CCA |
| Lys | Val | Thr | Ile | Leu | Ala | Arg | Ser | Thr | Leu | Phe | Phe | Arg | Glu | Asp | Pro |
| | 295 | | | | | 300 | | | | | 305 | | | | |
| GCT | ATA | GGT | GAA | GCT | GTT | ACT | GCT | GCA | TTT | CGC | ATG | GAA | GGC | ATT | GAA |
| Ala | Ile | Gly | Glu | Ala | Val | Thr | Ala | Ala | Phe | Arg | Met | Glu | Gly | Ile | Glu |
| 310 | | | | | 315 | | | | | 320 | | | | | 325 |
| GTG | CGT | GAG | CAT | ACT | CAA | GCA | AGC | CAA | GTT | GCC | TAT | ATC | AAT | GGT | GAA |
| Val | Arg | Glu | His | Thr | Gln | Ala | Ser | Gln | Val | Ala | Tyr | Ile | Asn | Gly | Glu |
| | | | | 330 | | | | | 335 | | | | | 340 | |
| GGG | GAC | GGC | GAA | TTC | GTG | CTC | ACC | ACG | GCG | CAC | GGC | GAA | CTG | CGC | GCC |
| Gly | Asp | Gly | Glu | Phe | Val | Leu | Thr | Thr | Ala | His | Gly | Glu | Leu | Arg | Ala |
| | | | 345 | | | | | 350 | | | | | 355 | | |
| GAC | AAG | CTG | CTG | GTC | GCC | ACC | GGC | CGC | GCG | CCC | AAC | ACA | CGC | AAG | CTG |
| Asp | Lys | Leu | Leu | Val | Ala | Thr | Gly | Arg | Ala | Pro | Asn | Thr | Arg | Lys | Leu |
| | | 360 | | | | | 365 | | | | | 370 | | | |
| GCA | CTG | GAT | GCG | ACG | GGC | GTC | ACG | CTC | ACC | CCC | CAA | GGC | GCT | ATC | GTC |
| Ala | Leu | Asp | Ala | Thr | Gly | Val | Thr | Leu | Thr | Pro | Gln | Gly | Ala | Ile | Val |
| | 375 | | | | | 380 | | | | | 385 | | | | |
| ATC | GAC | CCC | GGC | ATG | CGT | ACA | AGC | GTG | GAA | CAC | ATC | TAC | GCC | GCA | GGC |
| Ile | Asp | Pro | Gly | Met | Arg | Thr | Ser | Val | Glu | His | Ile | Tyr | Ala | Ala | Gly |
| 390 | | | | | 395 | | | | | 400 | | | | | 405 |
| GAC | TGC | ACC | GAC | CAG | CCG | CAG | TTC | GTC | TAT | GTG | GCG | GCA | GCG | GCC | GGC |
| Asp | Cys | Thr | Asp | Gln | Pro | Gln | Phe | Val | Tyr | Val | Ala | Ala | Ala | Ala | Gly |
| | | | | 410 | | | | | 415 | | | | | 420 | |
| ACT | CGC | GCC | GCG | ATC | AAC | ATG | ACC | GGC | GGT | GAC | GCC | GCC | CTG | AAC | CTG |
| Thr | Arg | Ala | Ala | Ile | Asn | Met | Thr | Gly | Gly | Asp | Ala | Ala | Leu | Asn | Leu |
| | | | 425 | | | | | 430 | | | | | 435 | | |
| ACC | GCG | ATG | CCG | GCC | GTG | GTG | TTC | ACC | GAC | CCG | CAA | GTG | GCG | ACC | GTA |
| Thr | Ala | Met | Pro | Ala | Val | Val | Phe | Thr | Asp | Pro | Gln | Val | Ala | Thr | Val |
| | | 440 | | | | | 445 | | | | | 450 | | | |
| GGC | TAC | AGC | GAG | GCG | GAA | GCG | CAC | CAT | GAC | GGC | ATC | AAA | ACT | GAT | AGT |
| Gly | Tyr | Ser | Glu | Ala | Glu | Ala | His | His | Asp | Gly | Ile | Lys | Thr | Asp | Ser |
| | 455 | | | | | 460 | | | | | 465 | | | | |
| CGC | ACG | CTA | ACG | CTG | GAC | AAC | GTG | CCG | CGC | GCG | CTC | GCC | AAC | TTC | GAC |
| Arg | Thr | Leu | Thr | Leu | Asp | Asn | Val | Pro | Arg | Ala | Leu | Ala | Asn | Phe | Asp |
| 470 | | | | | 475 | | | | | 480 | | | | | 485 |
| ACG | CGC | GGC | TTC | ATC | AAA | CTG | GTG | GTT | GAA | GAA | GGG | AGC | GGA | CGA | CTG |
| Thr | Arg | Gly | Phe | Ile | Lys | Leu | Val | Val | Glu | Glu | Gly | Ser | Gly | Arg | Leu |
| | | | | 490 | | | | | 495 | | | | | 500 | |
| ATC | GGC | GTC | CAG | GCA | GTG | GCC | CCG | GAA | GCG | GGC | GAA | CTG | ATC | CAG | ACG |
| Ile | Gly | Val | Gln | Ala | Val | Ala | Pro | Glu | Ala | Gly | Glu | Leu | Ile | Gln | Thr |
| | | | 505 | | | | | 510 | | | | | 515 | | |
| GCC | GCA | CTG | GCG | ATT | CGC | AAC | CGG | ATG | ACG | GTG | CAG | GAA | CTG | GCC | GAC |
| Ala | Ala | Leu | Ala | Ile | Arg | Asn | Arg | Met | Thr | Val | Gln | Glu | Leu | Ala | Asp |
| | | 520 | | | | | 525 | | | | | 530 | | | |
| CAG | TTG | TTC | CCC | TAC | CTG | ACG | ATG | GTC | GAA | GGG | TTG | AAG | CTC | GCG | GCG |
| Gln | Leu | Phe | Pro | Tyr | Leu | Thr | Met | Val | Glu | Gly | Leu | Lys | Leu | Ala | Ala |
| | 535 | | | | | 540 | | | | | 545 | | | | |
| CAG | ACC | TTC | AAC | AAG | GAT | GTG | AAG | CAG | CTT | TCC | TGC | TGC | GCC | GGG | TGA |
| Gln | Thr | Phe | Asn | Lys | Asp | Val | Lys | Gln | Leu | Ser | Cys | Cys | Ala | Gly | * |
| 550 | | | | | 555 | | | | | 560 | | | | | 565 |
| GGCTGCAGGA | | ATTCGATA | | | | | | | | | | | | | |

TABLE 5

MerApe 20 DNA and Amino Acid Sequences C(SEQ ID NO: 27-28)

| CTAGAACTAG | | TGGATCCCTA | | GATCTAAGAA | | GGAACCACA | | ATG | AGC | ACT | CTC | AAA |
|---|---|---|---|---|---|---|---|---|---|---|---|---|
| | | | | | | | | Met | Ser | Thr | Leu | Lys |
| | | | | | | | | 1 | | | | 5 |
| ATC | ACC | GGC | ATG | ACT | TGC | GAC | TCG | TGC | GCA | GTG | CAT | GTC | AAG | GAC | GCC |
| Ile | Thr | Gly | Met | Thr | Cys | Asp | Ser | Cys | Ala | Val | His | Val | Lys | Asp | Ala |
| | | | | 10 | | | | | 15 | | | | | 20 | |
| CTG | GAG | AAA | GTG | CCC | GGC | GTG | CAA | TCA | GCG | GAT | GTC | TCC | TAC | GCC | AAG |
| Leu | Glu | Lys | Val | Pro | Gly | Val | Gln | Ser | Ala | Asp | Val | Ser | Tyr | Ala | Lys |
| | | | 25 | | | | | 30 | | | | | 35 | | |
| GGC | AGC | GCC | AAG | CTC | GCC | ATT | GAG | GTC | GGC | ACG | TCA | CCC | GAC | GCG | CTG |
| Gly | Ser | Ala | Lys | Leu | Ala | Ile | Glu | Val | Gly | Thr | Ser | Pro | Asp | Ala | Leu |
| | | 40 | | | | | 45 | | | | | 50 | | | |
| ACG | GCC | GCT | GTA | GCT | GGA | CTC | GGT | TAT | CGG | GCC | ACG | CTG | GCC | GAT | GCC |

TABLE 5-continued

MerApe 20 DNA and Amino Acid Sequences C(SEQ ID NO: 27-28)

| | | | | | | | | | | | | | | |
|---|---|---|---|---|---|---|---|---|---|---|---|---|---|---|
| Thr | Ala | Ala | Val | Ala | Gly | Leu | Gly | Tyr | Arg | Ala | Thr | Leu | Ala | Asp | Ala |
|  | 55 |  |  |  | 60 |  |  |  |  |  | 65 |  |  |  |  |
| CCC | TCA | GTT | TCG | ACG | CCG | GGC | GGA | TTG | CTC | GAC | AAG | ATG | CGC | GAT | CTG |
| Pro | Ser | Val | Ser | Thr | Pro | Gly | Gly | Leu | Leu | Asp | Lys | Met | Arg | Asp | Leu |
| 70 |  |  |  |  | 75 |  |  |  |  |  | 80 |  |  |  | 85 |
| CTG | GGC | AGA | AAC | GAC | AAG | ACG | GGT | AGC | AGC | GGC | GCA | TTG | CAT | ATC | GCC |
| Leu | Gly | Arg | Asn | Asp | Lys | Thr | Gly | Ser | Ser | Gly | Ala | Leu | His | Ile | Ala |
|  |  |  |  | 90 |  |  |  |  | 95 |  |  |  |  | 100 |  |
| GTC | ATC | GGC | AGC | GGC | GGG | GCC | GCG | ATG | GCA | GCG | GCG | CTG | AAG | GCC | GTC |
| Val | Ile | Gly | Ser | Gly | Gly | Ala | Ala | Met | Ala | Ala | Ala | Leu | Lys | Ala | Val |
|  |  |  | 105 |  |  |  |  | 110 |  |  |  |  | 115 |  |  |
| GAG | CAA | GGC | GCA | CCT | GTC | ACG | CTG | ATC | GAG | CGC | GGC | ACC | ATC | GGC | GGC |
| Glu | Gln | Gly | Ala | Pro | Val | Thr | Leu | Ile | Glu | Arg | Gly | Thr | Ile | Gly | Gly |
|  |  | 120 |  |  |  |  | 125 |  |  |  |  | 130 |  |  |  |
| ACC | TGC | GTC | AAT | GTC | GGT | TGT | GTG | CCG | TCC | AAG | ATC | ATG | ATC | CGC | GCC |
| Thr | Cys | Val | Asn | Val | Gly | Cys | Val | Pro | Ser | Lys | Ile | Met | Ile | Arg | Ala |
|  | 135 |  |  |  | 140 |  |  |  |  | 145 |  |  |  |  |  |
| GCC | CAT | ATC | GCC | CAT | CTG | CGC | CGG | GAA | AGC | CCG | TTC | GAT | GGC | GGC | ATC |
| Ala | His | Ile | Ala | His | Leu | Arg | Arg | Glu | Ser | Pro | Phe | Asp | Gly | Gly | Ile |
| 150 |  |  |  |  | 155 |  |  |  |  | 160 |  |  |  |  | 165 |
| GCC | GCT | ACC | ACG | CCG | ACC | ATC | CAG | CGC | ACG | GCG | CTG | CTG | GCC | CAG | CAG |
| Ala | Ala | Thr | Thr | Pro | Thr | Ile | Gln | Arg | Thr | Ala | Leu | Leu | Ala | Gln | Gln |
|  |  |  |  | 170 |  |  |  |  | 175 |  |  |  |  | 180 |  |
| CAG | GCC | CGC | GTC | GAT | GAA | CTG | CGC | CAC | GCC | AAG | TAC | GAA | GGC | ATC | TTG |
| Gln | Ala | Arg | Val | Asp | Glu | Leu | Arg | His | Ala | Lys | Tyr | Glu | Gly | Ile | Leu |
|  |  |  | 185 |  |  |  |  | 190 |  |  |  |  | 195 |  |  |
| GAG | GGC | AAT | CCG | GCG | ATC | ACT | GTG | CTG | CAC | GGC | TCC | GCC | CGC | TTT | AAG |
| Glu | Gly | Asn | Pro | Ala | Ile | Thr | Val | Leu | His | Gly | Ser | Ala | Arg | Phe | Lye |
|  |  | 200 |  |  |  |  | 205 |  |  |  |  | 210 |  |  |  |
| GAC | AAT | CGC | AAC | CTG | ATC | GTG | CAA | CTC | AAC | GAC | GGC | GGC | GAG | CGC | GTG |
| Asp | Asn | Arg | Asn | Leu | Ile | Val | Gln | Leu | Asn | Asp | Gly | Gly | Glu | Arg | Val |
|  | 215 |  |  |  |  | 220 |  |  |  |  | 225 |  |  |  |  |
| GTG | GCA | TTC | GAC | CGC | TGC | CTG | ATC | GCC | ACC | GGC | GCG | AGC | CCG | GCC | GTG |
| Val | Ala | Phe | Asp | Arg | Cys | Leu | Ile | Ala | Thr | Gly | Ala | Ser | Pro | Ala | Val |
| 230 |  |  |  |  | 235 |  |  |  |  | 240 |  |  |  |  | 245 |
| CCA | CCA | ATT | CCT | GGT | CTC | AAG | GAC | ACT | CCT | TAC | TGG | ACT | TCC | ACT | GAA |
| Pro | Pro | Ile | Pro | Gly | Leu | Lys | Asp | Thr | Pro | Tyr | Trp | Thr | Ser | Thr | Glu |
|  |  |  |  | 250 |  |  |  |  | 255 |  |  |  |  | 260 |  |
| GCA | CTA | GTG | TCT | GAG | ACC | ATT | CCA | AAG | CGT | CTT | GCA | GTC | ATT | GGC | TCC |
| Ala | Leu | Val | Ser | Glu | Thr | Ile | Pro | Lys | Arg | Leu | Ala | Val | Ile | Gly | Ser |
|  |  |  | 265 |  |  |  |  | 270 |  |  |  |  | 275 |  |  |
| TCT | GTG | GTG | GCT | CTT | GAA | CTT | GCC | CAG | GCC | TTT | GCA | CGT | CTT | GGT | GCT |
| Ser | Val | Leu | Ala | Leu | Glu | Leu | Ala | Gln | Ala | Phe | Ala | Arg | Leu | Gly | Ala |
|  |  | 280 |  |  |  |  | 285 |  |  |  |  | 290 |  |  |  |
| AAA | GTG | ACC | ATT | CTT | GCA | CGC | TCC | ACT | CTC | TTC | TTT | CGT | GAA | GAC | CCA |
| Lys | Val | Thr | Ile | Leu | Ala | Arg | Ser | Thr | Leu | Phe | Phe | Arg | Glu | Asp | Pro |
|  | 295 |  |  |  |  | 300 |  |  |  |  | 305 |  |  |  |  |
| GCT | ATA | GGT | GAA | GCT | GTT | ACT | GCT | GCA | TTT | CGC | ATG | GAA | GGC | ATT | GAA |
| Ala | Ile | Gly | Glu | Ala | Val | Thr | Ala | Ala | Phe | Arg | Met | Glu | Gly | Ile | Glu |
| 310 |  |  |  |  | 315 |  |  |  |  | 320 |  |  |  |  | 325 |
| GTG | CGT | GAG | CAT | ACT | CAA | GCA | AGC | CAA | GTT | GCC | TAT | ATC | AAT | GGT | GAA |
| Val | Arg | Glu | His | Thr | Gln | Ala | Ser | Gln | Val | Ala | Tyr | Ile | Asn | Gly | Glu |
|  |  |  |  | 330 |  |  |  |  | 335 |  |  |  |  | 340 |  |
| GGG | GAC | GGC | GAA | TTC | GTG | CTC | ACC | ACG | GCG | CAC | GGC | GAA | CTG | CGC | GCC |
| Gly | Asp | Gly | Glu | Phe | Val | Leu | Thr | Thr | Ala | His | Gly | Glu | Leu | Arg | Ala |
|  |  |  | 345 |  |  |  |  | 350 |  |  |  |  | 355 |  |  |
| GAC | AAG | CTG | CTG | GTC | GCC | ACC | GGC | CGC | GCA | CCC | AAC | ACA | CGC | AAG | CTG |
| Asp | Lys | Leu | Leu | Val | Ala | Thr | Gly | Arg | Ala | Pro | Asn | Thr | Arg | Lys | Leu |
|  |  | 360 |  |  |  |  | 365 |  |  |  |  | 370 |  |  |  |
| GCA | CTG | GAT | GCG | ACG | GGC | GTC | ACG | CTC | ACC | CCC | CAA | GGC | GCT | ATC | GTC |
| Ala | Leu | Asp | Ala | Thr | Gly | Val | Thr | Leu | Thr | Pro | Gln | Gly | Ala | Ile | Val |
|  | 375 |  |  |  |  | 380 |  |  |  |  | 385 |  |  |  |  |
| ATC | GAC | CCC | GGC | ATG | CGT | ACA | AGC | GTG | GAA | CAC | ATC | TAC | GCC | GCA | GGC |
| Ile | Asp | Pro | Gly | Met | Arg | Thr | Ser | Val | Glu | His | Ile | Tyr | Ala | Ala | Gly |
| 390 |  |  |  |  | 395 |  |  |  |  | 400 |  |  |  |  | 405 |
| GAC | TGC | ACC | GAC | CAG | CCG | CAG | TTC | GTC | TAT | GTG | GCG | GCA | GCG | GCC | GGC |
| Asp | Cys | Thr | Asp | Gln | Pro | Gln | Phe | Val | Tyr | Val | Ala | Ala | Ala | Ala | Gly |
|  |  |  |  | 410 |  |  |  |  | 415 |  |  |  |  | 420 |  |
| ACT | CGC | GCC | GCG | ATC | AAC | ATG | ACC | GGT | GAC | GCC | GCC | CTG | AAC | CTG |  |
| Thr | Arg | Ala | Ala | Ile | Asn | Met | Thr | Gly | Gly | Asp | Ala | Ala | Leu | Asn | Leu |
|  |  |  | 425 |  |  |  |  | 430 |  |  |  |  | 435 |  |  |
| ACC | GCG | ATG | CCG | GCC | GTG | GTG | TTC | ACC | GAC | CCG | CAA | GTG | GCG | ACC | GTA |
| Thr | Ala | Met | Pro | Ala | Val | Val | Phe | Thr | Asp | Pro | Gln | Val | Ala | Thr | Val |
|  |  | 440 |  |  |  |  | 445 |  |  |  |  | 450 |  |  |  |
| GGC | TAC | AGC | GAG | GCG | GAA | GCG | CAC | CAT | GAC | GGC | ATC | AAA | ACT | GAT | AGT |
| Gly | Tyr | Ser | Glu | Ala | Glu | Ala | His | His | Asp | Gly | Ile | Lys | Thr | Asp | Ser |
|  | 455 |  |  |  | 460 |  |  |  |  | 465 |  |  |  |  |  |

TABLE 5-continued

MerApe 20 DNA and Amino Acid Sequences C(SEQ ID NO: 27-28)

| CGC | ACG | CTA | ACG | CTG | GAC | AAC | GTG | CCG | CGC | GCG | CTC | GCC | AAC | TTC | GAC |
|---|---|---|---|---|---|---|---|---|---|---|---|---|---|---|---|
| Arg | Thr | Leu | Thr | Leu | Asp | Asn | Val | Pro | Arg | Ala | Leu | Ala | Asn | Phe | Asp |
| 470 | | | | 475 | | | | | 480 | | | | | | 485 |
| ACG | CGC | GGC | TTC | ATC | AAA | CTG | GTG | GTT | GAA | GAA | GGG | AGC | GGA | CGA | CTG |
| Thr | Arg | Gly | Phe | Ile | Lys | Leu | Val | Val | Glu | Glu | Gly | Ser | Gly | Arg | Leu |
| | | | | 490 | | | | | 495 | | | | | 500 | |
| ATC | GGC | GTC | CAG | GCA | GTG | GCC | CCG | GAA | GCG | GGC | GAA | CTG | ATC | CAG | ACG |
| Ile | Gly | Val | Gln | Ala | Val | Ala | Pro | Glu | Ala | Gly | Glu | Leu | Ile | Gln | Thr |
| | | | 505 | | | | | 510 | | | | | 515 | | |
| GCC | GCA | CTG | GCG | ATT | CGC | AAC | CGG | ATG | ACG | GTG | CAG | GAA | CTG | GCC | GAC |
| Ala | Ala | Leu | Ala | Ile | Arg | Asn | Arg | Met | Thr | Val | Gln | Glu | Leu | Ala | Asp |
| | | 520 | | | | | 525 | | | | | 530 | | | |
| CAG | TTG | TTC | CCC | TAC | CTG | ACG | ATG | GTC | GAA | GGG | TTG | AAG | CTC | GCG | GCG |
| Gln | Leu | Phe | Pro | Tyr | Leu | Thr | Met | Val | Glu | Gly | Leu | Lys | Leu | Ala | Ala |
| | 535 | | | | | 540 | | | | | 545 | | | | |
| CAG | ACC | TTC | AAC | AAG | GAT | GTG | AAG | CAG | CTT | TCC | TGC | TGC | GCC | GGG | TGA |
| Gln | Thr | Phe | Asn | Lys | Asp | Val | Lys | Gln | Leu | Ser | Cys | Cys | Ala | Gly | * |
| 550 | | | | | 555 | | | | | 560 | | | | | 565 |
| GGCTGCAGGA | | ATTCGATA | | | | | | | | | | | | | |

TABLE 6

MerApe 29 DNA and Amino Acid Sequences (SEQ ID NO: 29-30)

| CTAGAACTAG | | TGGATCCCTA | | GATCTAAGAA | | GGAACCACA | | ATG | AGC | ACT | CTC | AAA |
|---|---|---|---|---|---|---|---|---|---|---|---|---|
| | | | | | | | | Met | Ser | Thr | Leu | Lys |
| ATC | ACC | GGC | ATG | ACT | TGC | GAC | TCG | TGC | GCA | GTG | CAT | GTC | AAG | GAC | GCC |
| Ile | Thr | Gly | Met | Thr | Cys | Asp | Ser | Cys | Ala | Val | His | Val | Lys | Asp | Ala |
| CTG | GAG | AAA | GTG | CCC | GGC | GTG | CAA | TCA | GCG | GAT | GTC | TCC | TAC | GCC | AAG |
| Leu | Glu | Lys | Val | Pro | Gly | Val | Gln | Ser | Ala | Asp | Val | Ser | Tyr | Ala | Lys |
| GGC | AGC | GCC | AAG | CTC | GCC | ATT | GAG | GTC | GGC | ACG | TCA | CCC | GAC | GCG | CTG |
| Gly | Ser | Ala | Lys | Leu | Ala | Ile | Glu | Val | Gly | Thr | Ser | Pro | Asp | Ala | Leu |
| ACG | GCC | GCT | GTA | GCT | GGA | CTC | GGT | TAT | CGG | GCC | ACG | CTG | GCC | GAT | GCC |
| Thr | Ala | Ala | Val | Ala | Gly | Leu | Gly | Tyr | Arg | Ala | Thr | Leu | Ala | Asp | Ala |
| CCC | TCA | GTT | TCG | ACG | CCG | GGC | GGA | TTG | CTC | GAC | AAG | ATG | CGC | GAT | CTG |
| Pro | Ser | Val | Ser | Thr | Pro | Gly | Gly | Leu | Leu | Asp | Lys | Met | Arg | Asp | Leu |
| CTG | GGC | AGA | AAC | GAC | AAG | ACG | GGT | AGC | AGC | GGC | GCA | TTG | CAT | ATC | GCC |
| Leu | Gly | Arg | Asn | Asp | Lys | Thr | Gly | Ser | Ser | Gly | Ala | Leu | His | Ile | Ala |
| GTC | ATC | GGC | AGC | GGC | GGG | GCC | GCG | ATG | GCA | GCG | GCG | CTG | AAG | GCC | GTC |
| Val | Ile | Gly | Ser | Gly | Gly | Ala | Ala | Met | Ala | Ala | Ala | Leu | Lys | Ala | Val |
| GAG | CAA | GGC | GCA | CCT | GTC | ACG | CTG | ATC | GAG | CGC | GGC | ACC | ATC | GGC | GGC |
| Glu | Gln | Gly | Ala | Pro | Val | Thr | Leu | Ile | Glu | Arg | Gly | Thr | Ile | Gly | Gly |
| ACC | TGC | GTC | AAT | GTC | GGT | TGT | GTG | CCG | TCC | AAG | ATC | ATG | ATC | CGC | GCC |
| Thr | Cys | Val | Asn | Val | Gly | Cys | Val | Pro | Ser | Lys | Ile | Met | Ile | Arg | Ala |
| GCC | CAT | ATC | GCC | CAT | CTG | CGC | CGG | GAA | AGC | CCG | TTC | GAT | GGC | GGC | ATC |
| Ala | His | Ile | Ala | His | Leu | Arg | Arg | Glu | Ser | Pro | Phe | Asp | Gly | Gly | Ile |
| GCC | GCT | ACC | ACG | CCG | ACC | ATC | CAG | CGC | ACG | GCG | CTG | CTG | GCC | CAG | CAG |
| Ala | Ala | Thr | Thr | Pro | Thr | Ile | Gln | Arg | Thr | Ala | Leu | Leu | Ala | Gln | Gln |
| CAG | GCC | CGC | GTC | GAT | GAA | CTG | CGT | CAT | GCA | AAG | TAT | GAA | GGT | ATT | CTA |
| Gln | Ala | Arg | Val | Asp | Glu | Leu | Arg | His | Ala | Lys | Tyr | Glu | Gly | Ile | Leu |
| GAA | GGT | AAC | CCA | GCC | ATC | ACT | GTG | CTT | CAT | GGC | TCT | GCA | CGT | TTC | AAG |
| Glu | Gly | Asn | Pro | Ala | Ile | Thr | Val | Leu | His | Gly | Ser | Ala | Arg | Phe | Lys |
| GAC | AAC | CGT | AAC | CTC | ATT | GTT | CAA | CTC | AAC | GAC | GGC | GGC | GAG | CGC | GTG |
| Asp | Asn | Arg | Asn | Leu | Ile | Val | Gln | Leu | Asn | Asp | Gly | Gly | Glu | Arg | Val |
| GTG | GCA | TTC | GAC | CGC | TGT | CTC | ATT | GCC | ACT | GGT | GCA | AGC | CCA | GCT | GTT |
| Val | Ala | Phe | Asp | Arg | Cys | Leu | Ile | Ala | Thr | Gly | Ala | Ser | Pro | Ala | Val |
| CCA | CCA | ATT | CCT | GGT | CTC | AAG | GAC | ACT | CCT | TAC | TGG | ACT | TCC | ACT | GAA |
| Pro | Pro | Ile | Pro | Gly | Leu | Lys | Asp | Thr | Pro | Tyr | Trp | Thr | Ser | Thr | Glu |
| GTG | TCT | GAG | ACC | ATT | CCA | AAG | CGT | CTT | GCA | GTC | ATT | GGC | TCC | | |
| Ala | Leu | Val | Ser | Glu | Thr | Ile | Pro | Lys | Arg | Leu | Ala | Val | Ile | Gly | Ser |
| TCT | GTG | GTG | GCT | CTT | GAA | CTT | GCC | CAG | GCC | TTT | GCA | CGT | CTT | GGT | GCT |
| Ser | Val | Val | Ala | Leu | Glu | Leu | Ala | Gln | Ala | Phe | Ala | Arg | Leu | Gly | Ala |
| AAA | GTG | ACC | ATT | CTT | GCA | CGC | TCC | ACT | CTC | TTC | TTT | CGT | GAA | GAC | CCA |
| Lys | Val | Thr | Ile | Leu | Ala | Arg | Ser | Thr | Leu | Phe | Phe | Arg | Glu | Asp | Pro |
| GCT | ATA | GGT | GAA | GCT | GTT | ACT | GCT | GCA | TTT | CGC | ATG | GAA | GGC | ATT | GAA |
| Ala | Ile | Gly | Glu | Ala | Val | Thr | Ala | Ala | Phe | Arg | Met | Glu | Gly | Ile | Glu |
| GTG | CGT | GAG | CAT | ACT | CAA | GCA | AGC | CAA | GTT | GCC | TAT | ATC | AAT | GGT | GAA |
| Val | Arg | Glu | His | Thr | Gln | Ala | Ser | Gln | Val | Ala | Tyr | Ile | Asn | Gly | Glu |
| GGG | GAC | GGC | GAA | TTC | GTG | CTC | ACC | ACG | GCG | CAC | GGC | GAA | CTG | CGC | GCC |
| Gly | Asp | Gly | Glu | Phe | Val | Leu | Thr | Thr | Ala | His | Gly | Glu | Leu | Arg | Ala |
| GAC | AAG | CTG | CTG | GTC | GCC | ACC | GGC | CGC | GCG | CCC | AAC | ACA | CGC | AAG | CTG |
| Asp | Lys | Leu | Leu | Val | Ala | Thr | Gly | Arg | Ala | Pro | Asn | Thr | Arg | Lys | Leu |
| GCA | CTG | GAT | GCG | ACG | GGC | GTC | ACG | CTC | ACC | CCC | CAA | GGC | GCT | ATC | GTC |
| Ala | Leu | Asp | Ala | Thr | Gly | Val | Thr | Leu | Thr | Pro | Gln | Gly | Ala | Ile | Val |

TABLE 6-continued

MerApe 29 DNA and Amino Acid Sequences (SEQ ID NO: 29–30)

| ATC | GAC | CCC | GGC | ATG | CGT | ACA | AGC | GTG | GAA | CAC | ATC | TAC | GCC | GCA | GGC |
|---|---|---|---|---|---|---|---|---|---|---|---|---|---|---|---|
| Ile | Asp | Pro | Gly | Met | Arg | Thr | Ser | Val | Glu | His | Ile | Tyr | Ala | Ala | Gly |
| GAC | TGC | ACC | GAC | CAG | CCG | CAG | TTC | GTC | TAT | GTG | GCG | GCA | GCG | GCC | GGC |
| Asp | Cys | Thr | Asp | Gln | Pro | Gln | Phe | Val | Tyr | Val | Ala | Ala | Ala | Ala | Gly |
| ACT | CGC | GCC | GCG | ATC | AAC | ATG | ACC | GGC | GGT | GAC | GCC | GCC | CTG | AAC | CTG |
| Thr | Arg | Ala | Ala | Ile | Asn | Met | Thr | Gly | Gly | Asp | Ala | Ala | Leu | Asn | Leu |
| ACC | GCG | ATG | CCG | GCC | GTG | GTG | TTC | ACC | GAC | CCG | CAA | GTG | GCG | ACC | GTA |
| Thr | Ala | Met | Pro | Ala | Val | Val | Phe | Thr | Asp | Pro | Gln | Val | Ala | Thr | Val |
| GGC | TAC | AGC | GAG | GCG | GAA | GCG | CAC | CAT | GAC | GGC | ATC | AAA | ACT | GAT | AGT |
| Gly | Tyr | Ser | Glu | Ala | Glu | Ala | His | His | Asp | Gly | Ile | Lys | Thr | Asp | Ser |
| CGC | ACG | CTA | ACG | CTG | GAC | AAC | GTG | CCG | CGC | GCG | CTC | GCC | AAC | TTC | GAC |
| Arg | Thr | Leu | Thr | Leu | Asp | Asn | Val | Pro | Arg | Ala | Leu | Ala | Asn | Phe | Asp |
| ACG | CGC | GGC | TTC | ATC | AAA | CTG | GTG | GTT | GAA | GAA | GGG | AGC | GGA | CGA | CTG |
| Thr | Arg | Gly | Phe | Ile | Lys | Leu | Val | Val | Glu | Glu | Gly | Ser | Gly | Arg | Leu |
| ATC | GGC | GTC | CAG | GCA | GTG | GCC | CCG | GAA | GCG | GGC | GAA | CTG | ATC | CAG | ACG |
| Ile | Gly | Val | Gln | Ala | Val | Ala | Pro | Glu | Ala | Gly | Glu | Leu | Ile | Gln | Thr |
| GCC | GCA | CTG | GCG | ATT | CGC | AAC | CGG | ATG | ACG | GTG | CAG | GAA | CTG | GCC | GAC |
| Ala | Ala | Leu | Ala | Ile | Arg | Asn | Arg | Met | Thr | Val | Gln | Glu | Leu | Ala | Asp |
| CAG | TTG | TTC | CCC | TAC | CTG | ACG | ATG | GTC | GAA | GGG | TTG | AAG | CTC | GCG | GCG |
| Gln | Leu | Phe | Pro | Tyr | Leu | Thr | Met | Val | Glu | Gly | Leu | Lys | Leu | Ala | Ala |
| CAG | ACC | TTC | AAC | AAG | GAT | GTC | AAG | CAG | CTT | TCC | TGC | TGC | GCC | GGG | TGA |
| Gln | Thr | Phe | Asn | Lys | Asp | Val | Lys | Gln | Leu | Ser | Cys | Cys | Ala | Gly | * |
| GGCTGCAGGA | ATTCGATA | | | | | | | | | | | | | | |

TABLE 7

MerApe 38 DNA and Amino Acid Sequences (SEQ ID NO: 13–14)

| CTAGAACTAG | | | TGGATCCCTA | | | GATCTAAGAA | | | GGAACCACA | | ATG | AGC | ACT | CTC | AAA |
|---|---|---|---|---|---|---|---|---|---|---|---|---|---|---|---|
| | | | | | | | | | | | Met | Ser | Thr | Leu | Lys |
| | | | | | | | | | | | | | | | 570 |
| ATC | ACC | GGC | ATG | ACT | TGC | GAC | TCG | TGC | GCA | GTG | CAT | GTC | AAG | GAC | GCC |
| Ile | Thr | Gly | Met | Thr | Cys | Asp | Ser | Cys | Ala | Val | His | Val | Lys | Asp | Ala |
| | | | | 575 | | | | | | 580 | | | | 585 | |
| CTG | GAG | AAA | GTG | CCC | GGC | GTG | CAA | TCA | GCG | GAT | GTC | TCC | TAC | GCC | AAG |
| Leu | Glu | Lys | Val | Pro | Gly | Val | Gln | Ser | Ala | Asp | Val | Ser | Tyr | Ala | Lys |
| | | | 590 | | | | | 595 | | | | | 600 | | |
| GGC | AGC | GCC | AAG | CTC | GCC | ATT | GAG | GTC | GGC | ACG | TCA | CCC | GAC | GCG | CTG |
| Gly | Ser | Ala | Lys | Leu | Ala | Ile | Glu | Val | Gly | Thr | Ser | Pro | Asp | Ala | Leu |
| | | 605 | | | | | 610 | | | | | 615 | | | |
| ACG | GCC | GCT | GTA | GCT | GGA | CTC | GGT | TAT | CGG | GCC | ACG | CTG | GCC | GAT | GCC |
| Thr | Ala | Ala | Val | Ala | Gly | Leu | Gly | Tyr | Arg | Ala | Thr | Leu | Ala | Asp | Ala |
| | 620 | | | | | 625 | | | | | 630 | | | | |
| CCC | TCA | GTT | TCG | ACG | CCG | GGC | GGA | TTG | CTC | GAC | AAG | ATG | CGC | GAT | CTG |
| Pro | Ser | Val | Ser | Thr | Pro | Gly | Gly | Leu | Leu | Asp | Lys | Met | Arg | Asp | Leu |
| 635 | | | | | 640 | | | | | 645 | | | | | 650 |
| CTG | GGC | AGA | AAC | GAC | AAG | ACG | GGT | AGC | AGC | GGC | GCA | TTG | CAT | ATC | GCC |
| Leu | Gly | Arg | Asn | Asp | Lys | Thr | Gly | Ser | Ser | Gly | Ala | Leu | His | Ile | Ala |
| | | | | 655 | | | | | 660 | | | | | 665 | |
| GTC | ATC | GGC | AGC | GGC | GGG | GCC | GCG | ATG | GCA | GCG | GCG | CTG | AAG | GCC | GTC |
| Val | Ile | Gly | Ser | Gly | Gly | Ala | Ala | Met | Ala | Ala | Ala | Leu | Lys | Ala | Val |
| | | | 670 | | | | | 675 | | | | | 680 | | |
| GAG | CAA | GGC | GCA | CCT | GTC | ACG | CTG | ATC | GAG | CGC | GGC | ACC | ATC | GGC | GGC |
| Glu | Gln | Gly | Ala | Pro | Val | Thr | Leu | Ile | Glu | Arg | Gly | Thr | Ile | Gly | Gly |
| | | 685 | | | | | 690 | | | | | 695 | | | |
| ACC | TGC | GTC | AAT | GTC | GGT | TGT | GTG | CCG | TCC | AAG | ATC | ATG | ATC | CGC | GCC |
| Thr | Cys | Val | Asn | Val | Gly | Cys | Val | Pro | Ser | Lys | Ile | Met | Ile | Arg | Ala |
| | 700 | | | | | 705 | | | | | 710 | | | | |
| GCC | CAT | ATC | GCC | CAT | CTG | CGC | CGG | GAA | AGC | CCG | TTC | GAT | GGC | GGC | ATC |
| Ala | His | Ile | Ala | His | Leu | Arg | Arg | Glu | Ser | Pro | Phe | Asp | Gly | Gly | Ile |
| 715 | | | | | 720 | | | | | 725 | | | | | 730 |
| GCC | GCT | ACC | ACG | CCG | ACC | ATC | CAG | CGC | ACG | GCG | CTG | CTG | GCC | CAG | CAG |
| Ala | Ala | Thr | Thr | Pro | Thr | Ile | Gln | Arg | Thr | Ala | Leu | Leu | Ala | Gln | Gln |
| | | | | 735 | | | | | 740 | | | | | 745 | |
| CAG | GCC | CGC | GTC | GAT | GAA | CTG | CGT | CAT | GCA | AAG | TAT | GAA | GGT | ATT | CTA |
| Gln | Ala | Arg | Val | Asp | Glu | Leu | Arg | His | Ala | Lys | Tyr | Glu | Gly | Ile | Leu |
| | | | 750 | | | | | 755 | | | | | 760 | | |
| GAA | GGT | AAC | CCA | GCC | ATC | ACT | GTG | CTT | CAT | GGC | TCT | GCA | CGT | TTC | AAG |
| Glu | Gly | Asn | Pro | Ala | Ile | Thr | Val | Leu | His | Gly | Ser | Ala | Arg | Phe | Lys |
| | | 765 | | | | | 770 | | | | | 775 | | | |
| GAC | AAC | CGT | AAC | CTC | ATT | GTT | CAA | CTC | AAC | GAC | GGC | GGC | GAG | CGC | GTG |
| Asp | Asn | Arg | Asn | Leu | Ile | Val | Gln | Leu | Asn | Asp | Gly | Gly | Glu | Arg | Val |
| | 780 | | | | | 785 | | | | | 790 | | | | |
| GTG | GCA | TTC | GAC | CGC | TGT | CTC | ATT | GCC | ACT | GGT | GCA | AGC | CCA | GCT | GTT |

TABLE 7-continued

MerApe 38 DNA and Amino Acid Sequences (SEQ ID NO: 13–14)

| Val 795 | Ala | Phe | Asp | Arg | Cys 800 | Leu | Ile | Ala | Thr | Gly 805 | Ala | Ser | Pro | Ala | Val 810 |
|---|---|---|---|---|---|---|---|---|---|---|---|---|---|---|---|
| CCA Pro | CCA Pro | ATT Ile | CCT Pro | GGT Gly 815 | CTC Leu | AAG Lys | GAC Asp | ACT Thr | CCT Pro 820 | TAC Tyr | TGG Trp | ACT Thr | TCC Ser | ACT Thr 825 | GAA Glu |
| GCA Ala | CTA Leu | GTG Val | TCT Ser 830 | GAG Glu | ACC Thr | ATT Ile | CCA Pro | AAG Lys 835 | CGT Arg | CTT Leu | GCA Ala | GTC Val | ATT Ile 840 | GGC Gly | TCC Ser |
| TCT Ser | GTG Val | GTG Val 845 | GCT Ala | CTT Leu | GAA Glu | CTT Leu | GCC Ala 850 | CAG Gln | GCC Ala | TTT Phe | GCA Ala | CGT Arg 855 | CTT Leu | GGT Gly | GCT Ala |
| AAA Lys | GTG Val 860 | ACC Thr | ATT Ile | CTT Leu | GCA Ala | CGC Arg 865 | TCC Ser | ACT Thr | CTC Leu | TTC Phe | TTT Phe 870 | CGT Arg | GAA Glu | GAC Asp | CCA Pro |
| GCT Ala 875 | ATA Ile | GGT Gly | GAA Glu | GCT Ala | GTT Val 880 | ACT Thr | GCT Ala | GCA Ala | TTT Phe | CGC Arg 885 | ATG Met | GAA Glu | GGC Gly | ATT Ile | GAA Glu 890 |
| GTG Val | CGT Arg | GAG Glu | CAT His | ACT Thr 895 | CAA Gln | GCA Ala | AGC Ser | CAA Gln | GTT Val 900 | GCC Ala | TAT Tyr | ATC Ile | AAT Asn | GGT Gly 905 | GAA Glu |
| GGT Gly | GAC Asp | GGT Gly | GAA Glu 910 | TTC Phe | GTC Val | CTA Leu | ACC Thr | ACT Thr 915 | GCT Ala | CAT His | GGT Gly | GAA Glu | CTT Leu 920 | CGT Arg | GCA Ala |
| GAC Asp | AAA Lys | CTC Leu 925 | CTT Leu | GTT Val | GCA Ala | ACT Thr | GGT Gly 930 | CGT Arg | GCA Ala | CCA Pro | AAC Asn | ACT Thr 935 | CGC Arg | AAA Lys | CTG Leu |
| GCA Ala | CTT Leu 940 | GAT Asp | GCA Ala | ACT Thr | GGT Gly 945 | GTG Val | ACC Thr | CTT Leu | ACT Thr | CCA Pro 950 | CAA Gln | GGT Gly | GCT Ala | ATT Ile | GTC Val |
| ATC Ile 955 | GAC Asp | CCC Pro | GGC Gly | ATG Met | CGT Arg 960 | ACA Thr | AGC Ser | GTG Val | GAA Glu | CAC His 965 | ATC Ile | TAC Tyr | GCC Ala | GCA Ala | GGC Gly 970 |
| GAC Asp | TGC Cys | ACC Thr | GAC Asp | CAG Gln 975 | CCG Pro | CAG Gln | TTC Phe | GTC Val | TAT Tyr 980 | GTG Val | GCG Ala | GCA Ala | GCG Ala | GCC Ala 985 | GGC Gly |
| ACT Thr | CGC Arg | GCC Ala | GCG Ala 990 | ATC Ile | AAC Asn | ATG Met | ACC Thr | GGC Gly 995 | GGT Gly | GAC Asp | GCC Ala | GCC Ala | CTG Leu 1000 | AAC Asn | CTG Leu |
| ACC Thr | GCG Ala | ATG Met 1005 | CCG Pro | GCC Ala | GTG Val | GTG Val | TTC Phe 1010 | ACC Thr | GAC Asp | CCG Pro | CAA Gln | GTG Val 1015 | GCG Ala | ACC Thr | GTA Val |
| GGC Gly | TAC Tyr 1020 | AGC Ser | GAG Glu | GCG Ala | GAA Glu | GCG Ala 1025 | CAC His | CAT His | GAC Asp | GGC Gly | ATC Ile 1030 | AAA Lys | ACT Thr | GAT Asp | AGT Ser |
| CGC Arg 1035 | ACG Thr | CTA Leu | ACG Thr | CTG Leu | GAC Asp 1040 | AAC Asn | GTG Val | CCG Pro | CGC Arg | GCG Ala 1045 | CTC Leu | GCC Ala | AAC Asn | TTC Phe | GAC Asp 1050 |
| ACG Thr | CGC Arg | GGC Gly | TTC Phe | ATC Ile 1055 | AAA Lys | CTG Leu | GTG Val | GTT Val | GAA Glu 1060 | GAA Glu | GGG Gly | AGC Ser | GGA Gly | CGA Arg 1065 | CTG Leu |
| ATC Ile | GGC Gly | GTC Val | CAG Gln 1070 | GCA Ala | GTG Val | GCC Ala | CCG Pro | GAA Glu 1075 | GCG Ala | GGC Gly | GAA Glu | CTG Leu | ATC Ile 1080 | CAG Gln | ACG Thr |
| GCC Ala | GCA Ala | CTG Leu 1085 | GCG Ala | ATT Ile | CGC Arg | AAC Asn | CGG Arg 1090 | ATG Met | ACG Thr | GTG Val | CAG Gln | GAA Glu 1095 | CTG Leu | GCC Ala | GAC Asp |
| CAG Gln | TTG Leu 1100 | TTC Phe | CCC Pro | TAC Tyr | CTG Leu | ACG Thr 1105 | ATG Met | GTC Val | GAA Glu | GGG Gly | TTG Leu 1110 | AAG Lys | CTC Leu | GCG Ala | GCG Ala |
| CAG Gln 1115 | ACC Thr | TTC Phe | AAC Asn | AAG Lys | GAT Asp 1120 | GTG Val | AAG Lys | CAG Gln | CTT Leu | TCC Ser 1125 | TGC Cys | TGC Cys | GCC Ala | GGG Gly | TGA * 1130 |
| GGCTGCAGGA | ATTCGATA | | | | | | | | | | | | | | |

TABLE 8

MerApe 47 DNA and Amino Acid Sequences (SEQ ID NO: 19–20)

| CTAGAACTAG | TGGATCCCTA | GATCTAAGAA | GGAACCACA | ATG Met | AGC Ser | ACT Thr | CTC Leu | AAA Lys 570 |
|---|---|---|---|---|---|---|---|---|
| ATC Ile | ACC Thr | GGC Gly | ATG Met | ACT Thr 575 | TGC Cys | GAC Asp | TCG Ser | TGC Cys | GCA Ala 580 | GTG Val | CAT His | GTC Val | AAG Lys | GAC Asp 585 | GCC Ala |

TABLE 8-continued

| MerApe 47 DNA and Amino Acid Sequences (SEQ ID NO: 19–20) | | | | | | | | | | | | | | | |
|---|---|---|---|---|---|---|---|---|---|---|---|---|---|---|---|
| CTG | GAG | AAA | GTG | CCC | GGC | GTG | CAA | TCA | GCG | GAT | GTC | TCC | TAC | GCC | AAG |
| Leu | Glu | Lys | Val 590 | Pro | Gly | Val | Gln | Ser 595 | Ala | Asp | Val | Ser | Tyr 600 | Ala | Lys |
| GGC | AGC | GCC | AAG | CTC | GCC | ATT | GAG | GTC | GGC | ACG | TCA | CCC | GAC | GCG | CTG |
| Gly | Ser | Ala 605 | Lys | Leu | Ala | Ile | Glu 610 | Val | Gly | Thr | Ser | Pro 615 | Asp | Ala | Leu |
| ACG | GCC | GCT | GTA | GCT | GGA | CTC | GGT | TAT | CGG | GCC | ACG | CTG | GCC | GAT | GCC |
| Thr | Ala 620 | Ala | Val | Ala | Gly | Leu 625 | Gly | Tyr | Arg | Ala | Thr 630 | Leu | Ala | Asp | Ala |
| CCC | TCA | GTT | TCG | ACG | CCG | GGC | GGA | TTG | CTC | GAC | AAG | ATG | CGC | GAT | CTG |
| Pro 635 | Ser | Val | Ser | Thr | Pro 640 | Gly | Gly | Leu | Leu | Asp 645 | Lys | Met | Arg | Asp | Leu 650 |
| CTG | GGC | AGA | AAC | GAC | AAG | ACG | GGT | AGC | AGC | GGC | GCA | TTG | CAT | ATC | GCC |
| Leu | Gly | Arg | Asn | Asp 655 | Lys | Thr | Gly | Ser | Ser 660 | Gly | Ala | Leu | His | Ile 665 | Ala |
| GTC | ATC | GGC | AGC | GGC | GGG | GCC | GCG | ATG | GCA | GCG | GCG | CTG | AAG | GCC | GTC |
| Val | Ile | Gly | Ser 670 | Gly | Gly | Ala | Ala | Met 675 | Ala | Ala | Ala | Leu | Lys 680 | Ala | Val |
| GAG | CAA | GGC | GCA | CCT | GTC | ACG | CTG | ATC | GAG | CGC | GGC | ACC | ATC | GGC | GGC |
| Glu | Gln | Gly 685 | Ala | Pro | Val | Thr | Leu 690 | Ile | Glu | Arg | Gly | Thr 695 | Ile | Gly | Gly |
| ACC | TGT | GTT | AAT | GTT | GGT | TGT | GTG | CCG | AGC | AAG | ATC | ATG | ATT | CGT | GCT |
| Thr | Cys 700 | Val | Asn | Val | Gly | Cys 705 | Val | Pro | Ser | Lys | Ile 710 | Met | Ile | Arg | Ala |
| GCT | CAC | ATT | GCT | CAT | CTT | CGT | GAA | TCT | CCA | TTT | GAT | GGT | GGC | ATT | |
| Ala 715 | His | Ile | Ala | His | Leu 720 | Arg | Arg | Glu | Ser | Pro 725 | Phe | Asp | Gly | Gly | Ile 730 |
| GCT | GCA | ACC | ACT | CCA | ACC | ATT | CAA | CGT | ACT | GCA | CTC | CTT | GCA | CAA | CAA |
| Ala | Ala | Thr | Thr | Pro 735 | Thr | Ile | Gln | Arg | Thr 740 | Ala | Leu | Leu | Ala | Gln 745 | Gln |
| CAA | GCA | CGT | GTT | GAT | GAA | CTT | CGT | CAT | GCA | AAG | TAT | GAA | GGT | ATT | CTA |
| Gln | Ala | Arg | Val 750 | Asp | Glu | Leu | Arg | His 755 | Ala | Lys | Tyr | Glu | Gly 760 | Ile | Leu |
| GAA | GGT | AAC | CCA | GCC | ATC | ACT | GTG | CTT | CAT | GGC | TCT | GCA | CGT | TTC | AAG |
| Glu | Gly | Asn 765 | Pro | Ala | Ile | Thr | Val 770 | Leu | His | Gly | Ser | Ala 775 | Arg | Phe | Lys |
| GAC | AAC | CGT | AAC | CTC | ATT | GTT | CAA | CTC | AAC | GAC | GGC | GGC | GAG | CGC | GTG |
| Asp | Asn | Arg 780 | Asn | Leu | Ile | Val | Gln 785 | Leu | Asn | Asp | Gly | Gly 790 | Glu | Arg | Val |
| GTG | GCA | TTC | GAC | CGC | TGT | CTC | ATT | GCC | ACT | GGT | GCA | AGC | CCA | GCT | GTT |
| Val 795 | Ala | Phe | Asp | Arg | Cys 800 | Leu | Ile | Ala | Thr | Gly 805 | Ala | Ser | Pro | Ala | Val 810 |
| CCA | CCA | ATT | CCT | GGT | CTC | AAG | GAC | ACT | CCT | TAC | TGG | ACT | TCC | ACT | GAA |
| Pro | Pro | Ile | Pro | Gly 815 | Leu | Lys | Asp | Thr | Pro 820 | Tyr | Trp | Thr | Ser | Thr 825 | Glu |
| GCA | CTA | GTG | TCT | GAG | ACC | ATT | CCA | AAG | CGT | CTT | GCA | GTC | ATT | GGC | TCC |
| Ala | Leu | Val | Ser 830 | Glu | Thr | Ile | Pro | Lys 835 | Arg | Leu | Ala | Val | Ile 840 | Gly | Ser |
| TCT | GTG | GTG | GCT | CTT | GAA | CTT | GCC | CAG | GCC | TTT | GCA | CGT | CTT | GGT | GCT |
| Ser | Val | Val 845 | Ala | Leu | Glu | Leu | Ala 850 | Gln | Ala | Phe | Ala | Arg 855 | Leu | Gly | Ala |
| AAA | GTG | ACC | ATT | CTT | GCA | CGC | TCC | ACT | CTC | TTC | TTT | CGT | GAA | GAC | CCA |
| Lys | Val | Thr 860 | Ile | Leu | Ala | Arg | Ser 865 | Thr | Leu | Phe | Arg 870 | Glu | Asp | Pro | |
| GCT | ATA | GGT | GAA | GCT | GTT | ACT | GCT | GCA | TTT | CGC | ATG | GAA | GGC | ATT | GAA |
| Ala 875 | Ile | Gly | Glu | Ala | Val 880 | Thr | Ala | Ala | Phe | Arg 885 | Met | Glu | Gly | Ile | Glu 890 |
| GTG | CGT | GAG | CAT | ACT | CAA | GCA | AGC | CAA | GTT | GCC | TAT | ATC | AAT | GGT | GAA |
| Val | Arg | Glu | His | Thr 895 | Gln | Ala | Ser | Gln | Val 900 | Ala | Tyr | Ile | Asn | Gly 905 | Glu |
| GGT | GAC | GGT | GAA | TTC | GTC | CTA | ACC | ACT | GCT | CAT | GGT | GAA | CTT | CGT | GCA |
| Gly | Asp | Gly | Glu 910 | Phe | Val | Leu | Thr | Thr 915 | Ala | His | Gly | Glu | Leu 920 | Arg | Ala |
| GAC | AAA | CTC | CTT | GTT | GCA | ACT | GGT | CGT | GCA | CCA | AAC | ACT | CGC | AAA | CTG |
| Asp | Lys | Leu 925 | Leu | Val | Ala | Thr | Gly 930 | Arg | Ala | Pro | Asn | Thr 935 | Arg | Lys | Leu |
| GCA | CTT | GAT | GCA | ACT | GGT | GTG | ACC | CTT | ACT | CCA | CAA | GGT | GCT | ATT | GTC |
| Ala | Leu | Asp 940 | Ala | Thr | Gly | Val 945 | Thr | Leu | Thr | Pro | Gln 950 | Gly | Ala | Ile | Val |
| ATC | GAC | CCC | GGC | ATG | CGT | ACA | AGC | GTG | GAA | CAC | ATC | TAC | GCC | GCA | GGC |
| Ile 955 | Asp | Pro | Gly | Met | Arg 960 | Thr | Ser | Val | Glu | His 965 | Ile | Tyr | Ala | Ala | Gly 970 |
| GAC | TGC | ACC | GAC | CAG | CCG | CAG | TTC | GTC | TAT | GTG | GCG | GCA | GCG | GCC | GGC |
| Asp | Cys | Thr | Asp | Gln | Pro 975 | Gln | Phe | Val | Tyr | Val 980 | Ala | Ala | Ala | Ala 985 | Gly |
| ACT | CGC | GCC | GCG | ATC | AAC | ATG | ACC | GGC | GGT | GAC | GCC | GCC | CTG | AAC | CTG |
| Thr | Arg | Ala | Ala | Ile | Asn | Met | Thr | Gly | Gly | Asp | Ala | Ala | Leu | Asn | Leu |

TABLE 8-continued

MerApe 47 DNA and Amino Acid Sequences (SEQ ID NO: 19–20)

|   |   |   | 990 |   |   |   |   | 995 |   |   |   |   | 1000 |   |   |   |
|---|---|---|---|---|---|---|---|---|---|---|---|---|---|---|---|---|
| ACC | GCG | ATG | CCG | GCC | GTG | GTG | TTC | ACC | GAC | CCG | CAA | GTG | GCG | ACC | GTA |   |
| Thr | Ala | Met | Pro | Ala | Val | Val | Phe | Thr | Asp | Pro | Gln | Val | Ala | Thr | Val |   |
|   |   | 1005 |   |   |   |   | 1010 |   |   |   |   | 1015 |   |   |   |   |
| GGC | TAC | AGC | GAG | GCG | GAA | GCG | CAC | CAT | GAC | GGC | ATC | AAA | ACT | GAT | AGT |   |
| Gly | Tyr | Ser | Glu | Ala | Glu | Ala | His | His | Asp | Gly | Ile | Lys | Thr | Asp | Ser |   |
|   | 1020 |   |   |   |   | 1025 |   |   |   |   | 1030 |   |   |   |   |   |
| CGC | ACG | CTA | ACG | CTG | GAC | AAC | GTG | CCG | CGC | GCG | CTC | GCC | AAC | TTC | GAC |   |
| Arg | Thr | Leu | Thr | Leu | Asp | Asn | Val | Pro | Arg | Ala | Leu | Ala | Asn | Phe | Asp |   |
| 1035 |   |   |   |   | 1040 |   |   |   |   | 1045 |   |   |   |   | 1050 |   |
| ACG | CGC | GGC | TTC | ATC | AAA | CTG | GTG | GTT | GAA | GAA | GGG | AGC | GGA | CGA | CTG |   |
| Thr | Arg | Gly | Phe | Ile | Lys | Leu | Val | Val | Glu | Glu | Gly | Ser | Gly | Arg | Leu |   |
|   |   |   |   | 1055 |   |   |   |   | 1060 |   |   |   |   | 1065 |   |   |
| ATC | GGC | GTC | CAG | GCA | GTG | GCC | CCG | GAA | GCG | GGC | GAA | CTG | ATC | CAG | ACG |   |
| Ile | Gly | Val | Gln | Ala | Val | Ala | Pro | Glu | Ala | Gly | Glu | Leu | Ile | Gln | Thr |   |
|   |   |   | 1070 |   |   |   |   | 1075 |   |   |   |   | 1080 |   |   |   |
| GCC | GCA | CTG | GCG | ATT | CGC | AAC | CGG | ATG | ACG | GTG | CAG | GAA | CTG | GCC | GAC |   |
| Ala | Ala | Leu | Ala | Ile | Arg | Asn | Arg | Met | Thr | Val | Gln | Glu | Leu | Ala | Asp |   |
|   |   | 1085 |   |   |   |   | 1090 |   |   |   |   | 1095 |   |   |   |   |
| CAG | TTG | TTC | CCC | TAC | CTG | ACG | ATG | GTC | GAA | GGG | TTG | AAG | CTC | GCG | GCG |   |
| Gln | Leu | Phe | Pro | Tyr | Leu | Thr | Met | Val | Glu | Gly | Leu | Lys | Leu | Ala | Ala |   |
|   | 1100 |   |   |   |   | 1105 |   |   |   |   | 1110 |   |   |   |   |   |
| CAG | ACC | TTC | AAC | AAG | GAT | GTG | AAG | CAG | CTT | TCC | TGC | TGC | GCC | GGG | TGA |   |
| Gln | Thr | Phe | Asn | Lys | Asp | Val | Lys | Gln | Leu | Ser | Cys | Cys | Ala | Gly | * |   |
| 1115 |   |   |   |   | 1120 |   |   |   |   | 1125 |   |   |   |   | 1130 |   |
| GGCTGCAGGA | | AITCGATA | | | | | | | | | | | | | | |

---

We claim:

1. A nucleic acid molecule comprising a sequence encoding a metal ion resistance gene, said gene having a sequence selected from the group of coding sequences consisting of merApe9, merApe20, merApe29, merApe38, and merApe47 (SEQ ID NOS: 15, 27, 29, 13, and 19, respectively).

2. The nucleic acid molecule of claim 1 wherein said coding sequence is that of merApe9 (SEQ ID NO:15).

3. The nucleic acid molecule of claim 1 wherein said coding sequence is that merApe20 (SEQ ID NO:27).

4. The nucleic acid molecule of claim 1 wherein said coding sequence is that of merApe29 (SEQ ID NO:29).

5. The nucleic acid molecule of claim 1 wherein said coding sequence is that merApe38 (SEQ ID NO:13).

6. The nucleic acid molecule of claim 1 wherein said coding sequence is that of merApe47 (SEQ ID NO:19).

7. The nucleic acid molecule of claim 1 wherein said coding sequence is operably linked downstream of and under the regulatory control of a plant-expressible transcription and translation regulatory sequence.

8. A method of using a DNA molecule comprising a plant-expressible nucleotide sequence encoding a metal resistance protein operably linked to and expressed under the regulatory control of transcription regulatory sequences to produce a transgenic plant, transgenic plant cell or transgenic plant tissue, said method comprising the steps of:

a) cloning a plant expressible sequence encoding a metal resistance protein of claim 1 operably linked to transcription regulatory sequences functional in a plant cell to produce a metal resistance expression construct;

b) cloning the metal resistance expression construct of step (a) into a plasmid vector adapted for use in a plant cell to produce a metal resistance expression vector;

c) stably transforming said metal resistance expression vector of step (b) into a plant cell or tissue to produce transgenic plant cell or tissue; and optionally d) regenerating said transgenic plant tissue to produce a transgenic plant, whereby said metal resistance protein is expressed in said transgenic plant, transgenic plant cell or transgenic plant tissue, thereby increasing the resistance of said plant to metal ions.

9. The method of claim 8 wherein said sequence encoding a metal resistance protein has a nucleotide sequence that is one of merApe9, merApe20, merApe29, merApe38, and merApe47 (SEQ ID NOS: 15, 27, 29, 13, and 19, respectively).

10. The method of claim 9 wherein said coding sequence is that of merApe9 (SEQ ID NO:15).

11. The method of claim 9 wherein said coding sequence is that of merApe20 (SEQ ID NO:27).

12. The method of claim 9 wherein said coding sequence is that of merApe29 (SEQ ID NO:29).

13. The method of claim 9 wherein said coding sequence is that of merApe38 (SEQ ID NO:13).

14. The method of claim 9 wherein said coding sequence is that of merApe47 (SEQ ID NO:19).

15. The method of claim 8, wherein said transgenic plant is a dicotyledonous plant.

16. The method of claim 15 wherein said transgenic plant is a member of the Solanaceae.

17. The method of claim 15 wherein said transgenic plant is Arabidopsis.

18. The method of claim 8 wherein said transgenic plant is a monocotyledonous plant.

19. The method of claim 8 wherein said transgenic plant is a gymnosperm.

20. The method of claim 19 wherein said transgenic plant is a member of the Coniferae.

21. A transgenic plant comprising a sequence encoding a metal resistance protein, said coding sequence being operably linked to transcriptional regulatory sequences functional in a plant, wherein said plant expresses said metal resistance coding sequence, said coding sequence being one of merApe9, merApe20, merApe29, merApe38, and merApe47 (SEQ ID NO: 15, 27, 29, 13, and 19, respectively).

22. The transgenic plant of claim 21 wherein said plant is a dicotyledonous plant.

23. The transgenic plant of claim 22 wherein said plant is a member of the Solanaceae.

24. The transgenic plant of claim 22 wherein said plant is yellow poplar.

25. The transgenic plant of claim 21 wherein said plant is a monocotyledonous plant.

26. The transgenic plant of claim 21 wherein said plant is a gymnosperm.

27. The transgenic plant of claim 26 wherein said plant is a member of the Coniferae.

28. A method of producing a transgenic plant, transgenic plant cell or transgenic plant tissue having greater resistance to metal ions than a corresponding parental plant, plant tissue or plant cell, said method comprising the steps of:

a) stably transforming the plant-expressible mercury resistance coding sequence of claim 1 into a plant cell to produce a transgenic plant cell;

b) optionally regenerating a transgenic plant from the transgenic plant cell of step (a); and c) growing the transgenic plant, transgenic plant cell or transgenic plant tissue under conditions which allow the expression of said construct, whereby the expression of said metal resistance protein has the result that resistance is expressed.

\* \* \* \* \*

UNITED STATES PATENT AND TRADEMARK OFFICE
CERTIFICATE OF CORRECTION

PATENT NO. : 5,668,294
DATED : September 16, 1997
INVENTOR(S) : Meagher et al.

It is certified that error appears in the above-identified patent and that said Letters Patent is hereby corrected as shown below:

<u>In the Abstract</u>: At line 4, delete "by" and replace with --but--.

At column 3, line 4, delete "are"; at line 28, delete "are"; at line 65 delete "fragment" and replace with --fragments--.

At column 4, line 7, delete "sequences" and replace with --sequence--.

At column 7, line 19, delete "this" and replace with --these--; at lines 46-47 delete "signi-ficatn" and replace with --significant--.

At column 9, line 5, delete "19)," and replace with --19,--; at line 11 delete "ecperiments" and replace with --experiments--.

At column 11, line 8, delete "changes" and replace with --changed--.

At colum 12, line 4, delete "met" and replace with --mer--; and delete "PDU202 carriers" and replace with --pDU292 carries--.

At column 14, line 5, delete "Physiol."

At column 15, line 9, delete "SKIT" and replace with --SKII--.

Signed and Sealed this

Twentieth Day of January, 1998

Attest:

BRUCE LEHMAN

Attesting Officer

Commissioner of Patents and Trademarks